United States Patent
Hovatta et al.

(10) Patent No.: US 12,195,757 B2
(45) Date of Patent: *Jan. 14, 2025

(54) METHODS OF PRODUCING RPE CELLS

(71) Applicant: BioLamina AB, Sundbyberg (SE)

(72) Inventors: Outi Hovatta, Esbo (FI); Karl Tryggvason, Singapore (SG)

(73) Assignee: BioLamina AB, Sundbyberg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,712

(22) Filed: Aug. 22, 2023

(65) Prior Publication Data

US 2024/0132838 A1 Apr. 25, 2024
US 2024/0228955 A9 Jul. 11, 2024

Related U.S. Application Data

(63) Continuation of application No. 17/138,327, filed on Dec. 30, 2020, now Pat. No. 11,767,509, which is a continuation of application No. 14/646,059, filed as application No. PCT/IB2013/003160 on Dec. 3, 2013, now Pat. No. 10,889,801.

(60) Provisional application No. 61/733,314, filed on Dec. 4, 2012, provisional application No. 61/732,764, filed on Dec. 3, 2012.

(51) Int. Cl.
*C12N 5/079* (2010.01)
*A61K 9/00* (2006.01)
*A61K 35/30* (2015.01)
*C12N 5/00* (2006.01)

(52) U.S. Cl.
CPC .......... *C12N 5/0621* (2013.01); *A61K 9/0019* (2013.01); *A61K 9/0048* (2013.01); *A61K 35/30* (2013.01); *C12N 5/0056* (2013.01); *C12N 2500/92* (2013.01); *C12N 2500/98* (2013.01); *C12N 2501/115* (2013.01); *C12N 2506/02* (2013.01); *C12N 2533/50* (2013.01); *C12N 2533/52* (2013.01)

(58) Field of Classification Search
None
See application file for complete search history.

(56) References Cited

U.S. PATENT DOCUMENTS 10,889,801 B2 * 1/2021 Hovatta ............... C12N 5/0621
11,767,509 B2 * 9/2023 Hovatta ............... A61K 9/0048
435/377

2010/0203635 A1 8/2010 Tryggvason et al.
2012/0156782 A1 6/2012 Tryggvason
2013/0196369 A1 8/2013 Hikita et al.

OTHER PUBLICATIONS

Reyes, Alvaro Plaza et al., Xeno-Free and Defined Human Embryonic Stem Cell-Derived Retinal Pigment Epithelial Cells Functionally Integrate in a Large-Eyed Preclinical Model, Stem Cell Reports, Jan. 12, 2016, pp. 9-17, vol. 6.
Klimanskaya; Retinal Pigment Epithelium; Methods of Enzymology, vol. 418; pp. 169-194; 2006.
Krohne et al.; Generation of Retinal Pigment Epithelial Cells from Small Molecules and OCT4 Reprogrammed Human Induced Pluripotent Stem Cells; Stem Cells Translation Medicine 2012:1, pp. 96-109; Feb. 6, 2012.
Rodin et al.; Long-term self-renewal of human pluripotent stem cells on human recombinant laminin-511; Nature Biotechnology, vol. 28, No. 6, pp. 611-617; Jun. 2010.
Rowland et al.; Differentiation of human pluripotent stem cells to retinal pigmented epithelium in defined conditions using purified extracellular matrix proteins; Journal of Tissue Engineering and Regenerative Medicine, pp. 642-653; Apr. 18, 2012.
Vaajasaari et al.; Toward the defined and xeno-free differentiation of functional human pluripotent stem cell-derived retinal pigment epithelial cells; Moluecular Vision 2011; 17; pp. 558-575; Feb. 22, 2011.
Zahabi et al.; A New Efficient Protocol for Directed Differentiation of Retinal Pigmented Epithelial Cells from Normal and Retinal Disease Induced Pluripotent Stem Cells; Stem Cells and Development, vol. 21, No. 12; pp. 2262-2272; 2012.
Reyes, Alvaro Plaza et al., Supplemental Information—Xeno-Free and Defined Human Embryonic Stem Cell-Derived Retinal Pigment Epithelial Cells Functionally Integrate in a Large-Eyed Preclinical Model, Stem Cell Reports, Jan. 12, 2016, pp. 9-17, vol. 6.

* cited by examiner

*Primary Examiner* — Blaine Lankford
(74) *Attorney, Agent, or Firm* — Lippes Mathias LLP

(57) ABSTRACT

The present disclosure relates to the use of laminin-521 in obtaining retinal pigment epithelium (RPE) cells. Pluripotent human embryonic stem cells are cultured on plates coated with recombinant laminin-521 (laminin-11), in totally defined and xeno-free conditions. A first cell culture medium contains a growth factor, and a second cell culture medium does not contain growth factor. The stem cells are first exposed to the first cell culture medium, then exposed to the second cell culture medium for a longer time period. After a number of weeks, clinical grade RPE cells are obtained from the stem cells.

14 Claims, 16 Drawing Sheets
Specification includes a Sequence Listing.

METHODS OF PRODUCING RPE CELLS

CROSS-REFERENCE TO RELATED APPLICATIONS

This application is a continuation of U.S. patent application Ser. No. 17/138,327, filed Dec. 30, 2020, now 11,767,509, which is a continuation of U.S. patent application Ser. No. 14/646,059, filed May 20, 2015, now U.S. Pat. No. 10,889,801, which is a 371 of PCT Application No. PCT/IB2013/003160, filed Dec. 3, 2013, which claims priority to U.S. Provisional Patent Application Ser. No. 61/732,764, filed Dec. 3, 2012, and to U.S. Provisional Patent Application Ser. No. 61/733,314, filed Dec. 4, 2012. The entireties of those provisional applications are fully incorporated by reference herein.

INCORPORATION BY REFERENCE STATEMENT

This application incorporates by reference a sequence listing submitted herewith as Icti200026us03.xml, created on Aug. 22, 2023, and having a file size of 39,970 bytes.

BACKGROUND

This application relates to cell biology, cell differentiation, cell therapy, molecular biology, proteins, recombinant human proteins, nucleic acids, and laminins.

Basal laminae (basement membranes) are sheet-like, cell-associated extracellular matrices that play a central role in cell growth, cellular differentiation, cell phenotype maintenance, tissue development, and tissue maintenance. They are present in virtually all tissues, and appear in the earliest stages of embryonic development.

Basal laminae are central to a variety of architectural and cell-interactive functions. For example:

1. They serve as architectural supports for tissues, providing adhesive substrata for cells.

2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.

3. Basal laminae create highly interactive surfaces that can promote cell migration and cell elongation during embryogenesis and wound repair. Following an injury, they provide a surface upon which cells regenerate to restore normal tissue function.

4. Basal laminae present information encoded in their structure to contacting cells that is important for cellular differentiation, prevention of apoptosis, and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. Additional components include proteoglycans such as agrin and perlecan and nidogens (entactins). To date, six type IV collagen polypeptide chains and at least twelve laminin subunit chains have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular behavior and function. Laminins are important in both maintaining cell/tissue phenotype, as well as in promoting cell growth and differentiation in tissue repair and development.

Laminins are large, multi-domain proteins, with a common structural organization. The laminin molecule integrates various matrix and cell interactive functions into one molecule.

A laminin protein molecule comprises one α-chain subunit, one β-chain subunit, and one γ-chain subunit, all joined together in a trimer through a coiled-coil domain. FIG. 1 depicts the resulting structure of the laminin molecule. The twelve known laminin subunit chains can form at least 15 trimeric laminin types in native tissues. Within the trimeric laminin structures are identifiable domains that possess binding activity towards other laminin and basal lamina molecules, and membrane-bound receptors. FIG. 2 shows the three laminin chain subunits separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

There exist five different alpha chains, three beta chains and three gamma chains that in human tissues have been found in at least fifteen different combinations. These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2p1γ3).

Human embryonic stem (hES) cells hold promise for the development of regenerative medicine for a variety of diseases, such as spinal cord and cardiac injuries, type I diabetes and neurodegenerative disorders like Parkinson's disease. A stem cell is an undifferentiated cell from which specialized cells are subsequently derived. Embryonic stem cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics.

One of the main problems with large-scale propagation of hES cells is that they poorly survive replating after dissociation into single cell suspension. This, in turn, makes passaging tedious and large-scale automated expansions impossible. However, hES cells released into single cell suspension using trypsin treatment in the presence of a rho-kinase (ROCK) inhibitor[10] or blebbistatin[11] can be plated and expanded from single clones, but the molecules are not components of the natural stem cell niche, and they affect the actin cytoskeleton and thus can cause cell damage. Therefore, the use of the ROCK inhibitor may not be a preferred solution for long-term expansion of hES cells aimed for cell therapy purposes.

For the purposes of regenerative medicine, there is a desire to develop methods that allow derivation and long-term cultures of pluripotent stem cells under chemically defined, xeno-free, pathogen-free, and stable batch-to-batch conditions. Moreover, such methods should allow fast and economically efficient scale-up to acquire large quantities of pluripotent hES/hiPS cells in a short period of time. Preferably, the methods should also allow clonal survival of human ES cells in media containing no synthetic inhibitor of apoptosis, that could facilitate scientific and clinical applications involving cell sorting or gene knock-out in the cells.

BRIEF DESCRIPTION

The present disclosure provides methods for culturing stem cells to obtain retinal pigment epethilum (RPE) cells.

Disclosed in various embodiments herein are methods of obtaining retinal pigment epithelium (RPE) cells, comprising: culturing one or more stem cells on a substrate comprising a laminin, wherein the laminin is an intact protein or a protein fragment; exposing the stem cells to a first cell culture medium that contains a growth factor, the first cell culture medium being completely chemically defined and xeno-free; after a first time period, removing the first cell culture medium and exposing the stem cells to a second cell culture medium that does not contain the growth factor, the second cell culture medium being completely chemically defined and xeno-free; and periodically changing the second cell culture medium to obtain the RPE cells.

The laminin can be laminin-521 or laminin-511. The laminin may be an effective recombinant laminin.

In some embodiments, the substrate further comprises a cadherin. The cadherin may be e-cadherin. The weight ratio of the laminin to the cadherin can be from about 5:1 to about 15:1. Sometimes, the laminin is laminin-521 and the cadherin is e-cadherin. The weight ratio of laminin-521 to e-cadherin may be from about 5:1 to about 15:1.

The first cell culture medium can be TeSR2 medium or Nutristem medium.

The first cell culture medium can contain FGF2 in an amount of greater than zero to 3.9 ng/ml.

The second cell culture medium can be TeSR2 medium or Nutristem medium, the second cell culture medium having no FGF2.

The substrate, the first cell culture medium, and the second cell culture medium do not contain any substances of animal origin.

The first time period may be about one week.

The periodic changing of the second cell culture medium may occur every week, with the RPE cells being obtained after a total of about eight weeks.

Also disclosed herein in different embodiments are methods of treating a patient having macular degeneration, comprising: injecting retinal pigment epithelium (RPE) cells into an eye of the patient; wherein the RPE cells have been obtained under completely chemically defined and xeno-free conditions. The RPE cells may be obtained according to the methods described above.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

In FIG. 4, the cells were cultured without ROCK inhibitor. In FIG. 5, the cells were cultured with ROCK inhibitor Y-27632.

DETAILED DESCRIPTION

Figure 1:
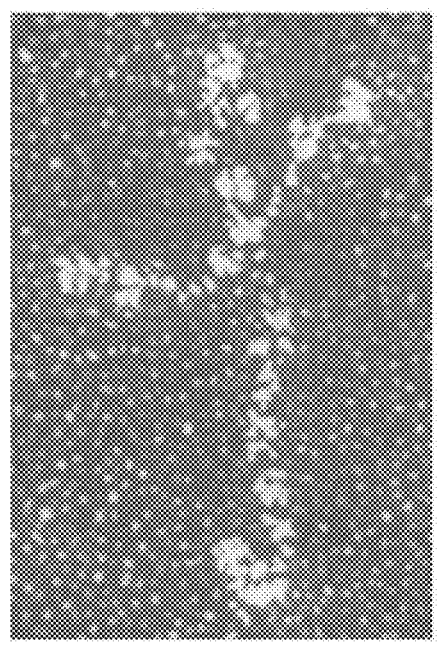
FIG. 1 is a rotary shadowing electron microscopy picture of a recombinant laminin molecule.
Figure 2:
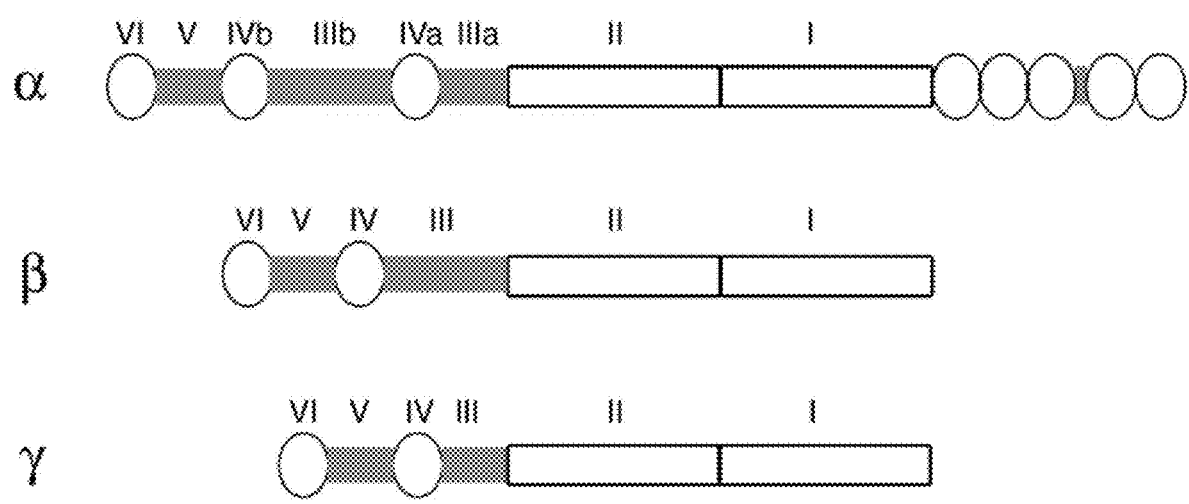
FIG. 2 shows the structural motifs of laminin α, β, and γ chains. The N-terminal, internal, and C-terminal globular domains are depicted as white ovals. The coiled-coil forming domains (I and II) are shown as white rectangles. The rod-like structures (domains V, IIIb, and IIIa) are depicted as grey rectangles.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

Unless otherwise stated, the techniques utilized in this application may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, Second Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), or the Ambion 1998 Catalog (Ambion, Austin, Tex.).

As used herein, the term "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). The "isolated" sequence may, however, be linked to other nucleotide sequences that do not naturally flank the recited sequence, such as a heterologous promoter sequence, or other vector sequences. It is not necessary for the isolated nucleic acid sequence to be free of other cellular material to be considered "isolated", as a nucleic acid sequence according to the disclosure may be part of an expression vector that is used to transfect host cells (see below).

The present disclosure provides recombinant expression vectors comprising a full length laminin β2 chain nucleic acid sequence (SEQ ID NO: 4) of the human laminin β2 chain. In some embodiments, the expression vectors comprise a nucleic acid encoded by SEQ ID NO: 4, operatively linked to a heterologous promoter (i.e. is not the naturally occurring promoter for the given β2 laminin chain). A promoter and a laminin β2 chain nucleic acid sequence are "operatively linked" when the promoter is capable of driving expression of the laminin β2 chain DNA into RNA.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In the present disclosure, the expression of the laminin polypeptide sequence is directed by the promoter sequences of the disclosure, by operatively linking the promoter sequences of the disclosure to the gene to be expressed. In general, expression vectors of utility in recombinant DNA techniques are often in the form of plasmids. In the present specification, "plasmid" and "vector" may be used interchangeably, as the plasmid is the most commonly used form of vector. However, the disclosure is intended to include other forms of expression vectors, such as viral vectors (e.g., replication defective retroviruses, adenoviruses and adeno-associated viruses), which serve equivalent functions.

The vector may also contain additional sequences, such as a polylinker for subcloning of additional nucleic acid sequences, or a polyadenylation signal to effect proper polyadenylation of the transcript. The nature of the polyadenylation signal is not believed to be crucial to the successful practice of the methods of the disclosure, and any such sequence may be employed, including but not limited to the SV40 and bovine growth hormone poly-A sites. Also contemplated as an element of the vector is a termination sequence, which can serve to enhance message levels and to minimize readthrough from the construct into other sequences. Additionally, expression vectors typically have selectable markers, often in the form of antibiotic resistance genes, that permit selection of cells that carry these vectors.

In further embodiments, the present disclosure provides host cells transfected with the laminin β2 chain-expressing recombinant expression vectors disclosed herein. As used herein, the term "host cell" is intended to refer to a cell into which a nucleic acid of the present disclosure, such as a recombinant expression vector, has been introduced. Such cells may be prokaryotic, which can be used, for example, to rapidly produce a large amount of the expression vectors of the disclosure, or may be eukaryotic, for functional studies.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the disclosure. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2.sup.nd Ed. (R. I. Freshney. 1987. Liss, Inc. New York, N.Y.).

In another aspect, the present disclosure provides an isolated full length human laminin β2 chain polypeptide consisting of the amino acid sequence of SEQ ID NO: 2.

As used herein, an "isolated polypeptide" refers to a polypeptide that is substantially free of other proteins, including other laminin chains, and gel agents, such as polyacrylamide and agarose. In preferred embodiments, the isolated laminin polypeptide is free of detectable contaminating laminin chains. Thus, the protein can either be isolated from natural sources, or recombinant protein can be isolated from the transfected host cells disclosed above.

In another aspect, the present disclosure provides isolated laminin-521. As used herein, the term "laminin-521" refers to the protein formed by joining α5, β2 and γ1 chains together. The term should be construed as encompassing both recombinant laminin-521 and heterotrimeric laminin-521 from naturally occurring sources. In preferred embodiments, the laminin-521 comprises recombinant laminin-521 (or "r-laminin-521"). The term "recombinant" indicates that the protein is artificially produced in cells that do not normally express such proteins.

As used herein, the term "r-laminin-521" refers to recombinant heterotrimeric laminin-521, expressed by a host cell that has been transfected with one or more expression vectors comprising at least one nucleic acid sequence encoding a laminin-521 chain selected from the α5, β2 and γ1 chains, or processed or secreted forms thereof. Such r-laminin-521 can thus comprise α5, β2, and γ1 sequences from a single organism, or from different organisms. Various laminin-521 chain DNA sequences are known in the art, and the use of any such sequence to prepare the r-laminin-521 of the disclosure is contemplated. (See, for example, Pouliot, N. et al., Experimental Cell Research 261(2):360-71, (2000); Kikkawa, Y. et al., Journal of Cell Science 113 (Pt 5):869-76, (2000); Church, H J. et al., Biochemical Journal 332 (Pt 2):491-8, (1998); Sorokin, L M. et al., Developmental Biology 189(2):285-300, (1997); Miner, J H. et al., Journal of Biological Chemistry 270(48):28523-6, (1995); Sorokin, L. et al., European Journal of Biochemistry 223(2):603-10, (1994)). In preferred embodiments, the r-laminin-521 is formed from recombinant human α5, β2, and γ1 polypeptide chains.

The disclosure encompasses those laminin molecules wherein only one or two chains that make up the recombinant heterotrimeric laminin-521 are encoded by endogenous laminin-521 chains. In preferred embodiments, each of the α5, β2, and γ1 polypeptide chains are expressed recombinantly.

The laminin-521 is an intact protein. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain.

Laminin-521 is a secreted protein, which is capable of being directed to the endoplasmic reticulum (ER), secretory vesicles, and the extracellular space as a result of a signal sequence. If the secreted protein is released into the extracellular space, the secreted protein can undergo extracellular processing to produce a "mature" protein. Such processing events can be variable, and thus may yield different versions of the final "mature protein". For example, the lengths of the α5, β2, and γ1 chains may vary between proteins. However, the final mature protein still has the same functionality, even though the chain lengths vary. The isolated laminin-521 of the present disclosure includes heterotrimers comprising both the full length polypeptide chains and any such naturally processed laminin-521 polypeptide chains.

As used herein, a laminin-521 polypeptide chain refers to a polypeptide chain according to one or more of the following:

(a) a polypeptide chain that comprises a polypeptide structure selected from the group consisting of: R1-R2-R3, R1-R2-R4, R3, R4, R1-R3, R1-R4, R2-R3, and R2-R4, wherein R1 is an amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from the group consisting of a α5 chain, a β2 chain, and a γ1 chain; and R4 is a secreted α5, β2, or γ1 laminin chain that further comprises an epitope tag (such as those described below), which can be placed at any position within the laminin chain amino acid sequence; or (b) a polypeptide chain that is encoded by a polynucleotide that hybridizes under high or low stringency conditions to the coding regions, or portions thereof, of one or more of the recombinant laminin-521 chain DNA sequences disclosed herein (SEQ ID NO: 4, SEQ ID NO: 5, SEQ ID NO: 6), or complementary sequences thereof; or (c) a polypeptide chain that has at least 70% identity to one or more of the disclosed laminin-521 polypeptide chain amino acid sequences (SEQ ID NO: 1, SEQ ID NO: 2, SEQ ID NO: 3), preferably at least 80% identity, and most preferably at least about 90% identity.

"Stringency of hybridization" is used herein to refer to washing conditions under which nucleic acid hybrids are stable. The disclosure also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of ordinary skill in the art, the stability of hybrids is reflected in the melting temperature ($T_M$) of the hybrids. $T_M$ decreases approximately 1-1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. As used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

Also contemplated are laminin-521-encoding nucleic acid sequences that hybridize to the polynucleotides of the present disclosure at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264.2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score 100, wordlength=12, to determine nucleotide sequences identity to the nucleic acid molecules of the disclosure. BLAST protein searches are performed with the XBLAST program, score=50, wordlength=3, to determine an amino acid sequence identity to a polypeptide of the disclosure. To obtain gapped alignments for comparison purposes, Gapped BLAST is utilized as described in Altschul et al. (Nucleic Acids. Res. 25:3389-3402, 1997). When utilizing BLAST and Gapped BLAST programs, the default parameters of the respective programs (e.g., XBLAST and NBLAST) are used.

Further embodiments of the present disclosure include polynucleotides encoding laminin-521 chain polypeptides having at least 70% identity, preferably at least 80% identity, and most preferably at least 90% identity to one or more of the polypeptide sequences contained in SEQ ID NO: 4, SEQ ID NO: 5, and SEQ ID NO: 6.

As used herein, "α5 polynucleotide" refers to polynucleotides encoding a laminin α5 chain. Such polynucleotides can be characterized by one or more of the following: (a) polynucleotides that encode polypeptides which share at least 70% identity, preferably 80% identity, and most preferably at least 90% identity with a sequence selected of SEQ ID NO: 5; (b) polynucleotides that hybridize under low or high stringency conditions to the coding sequence of SEQ ID NO: 5 or complementary sequences thereof; or (c) polynucleotides encoding a laminin α5 chain polypeptide with a general structure selected from the group consisting of R1-R2-R3, R1-R2-R4, R3, R4, R1-R3, R1-R4, R2-R3, and R2-R4, wherein R1 and R2 are as described above, R3 is a secreted α5 chain, and R4 is a secreted α5 chain that comprises an epitope tag.

As used herein, "β2 polynucleotides" refers to polynucleotides encoding a β2 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 4; (b) polynucleotides that hybridize under low or high stringency conditions to the coding sequences of SEQ ID NO: 4, or complementary sequences thereof; or (c) polynucleotides encoding a polypeptide with a general structure selected from R1-R2-R3, R1-R2-R4, R3, R4, R1-R3, R1-R4, R2-R3, and R2-R4, wherein R1 and R2 are as described above, R3 is a secreted β2 chain, and R4 is a secreted β2 chain that comprises an epitope tag.

As used herein, "γ1 polynucleotides" refers to polynucleotides encoding a γ1 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 6; (b) polynucleotides that hybridize under low or high stringency conditions to the coding sequence of SEQ ID NO: 6 or complementary sequences thereof; or (c) polynucleotides that encode a polypeptide with a general structure selected from R1-R2-R3, R1-R2-R4, R3, R4, R1-R3, R1-R4, R2-R3, and R2-R4, wherein R1 and R2 are as described above, R3 is a secreted γ1 chain, and R4 is a secreted γ1 chain that comprises an epitope tag.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

In preferred embodiments, cDNAs encoding the laminin α5, β2 and γ1 chains, or fragments thereof, are subcloned into an expression vector. Alternatively, laminin α5, β2 and/or γ1 gene sequences, including one or more introns, can be used for sub-cloning into an expression vector.

In other aspects, the present disclosure provides laminin-521 expressing-cells that have been transfected with an expression vector containing promoter sequences that are operatively linked to nucleic acid sequences encoding at least one polypeptide sequence comprising a sequence selected from the group consisting of the α5, β2 and γ1 chains of laminin-521, wherein the transfected cells secrete heterotrimeric containing the recombinant laminin chain. In preferred embodiments, the cells are systematically transfected with recombinant expression vectors containing promoter sequences that are operatively linked to nucleic acid sequences encoding polypeptide sequences comprising the α5, β2 and γ1 chains of laminin-521, which are even more preferably all human chains. After the multiple transfections, the cells express recombinant laminin-521 chains, which form the heterotrimeric r-laminin-521.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In preferred embodiments, the cells are stably transfected. Methods for stable transfection and selection of appropriate transfected cells are known in the art. In other preferred embodiments, a CMV promoter driven expression vector is used in a human kidney embryonic 293 cell line.

Any cell capable of expressing and secreting the r-laminin-521 can be used. Preferably, eukaryotic cells are used, and most preferably mammalian cells are used, including but not limited to kidney and epithelial cell lines. The promoter sequence used to drive expression of the individual chains or r-laminin-521 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). Carbohydrate and disulfide post-translational modifications are believed to be required for laminin-521 protein folding and function. This makes the use of eukaryotic cells preferable for producing functional r-laminin-521, although other systems are useful for obtaining, for example, antigens for antibody production. In most preferred embodiments, the mammalian cells do not express the laminin β2 chain endogenously. In other preferred embodiments, the cells do not express all of the laminin-521 chains endogenously.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

In some embodiments, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin-521, so long as the resulting r-laminin-521 remains functional.

In other embodiments, one of the r-laminin-521 chains is expressed as a fusion protein with a first epitope tag, and at least one other r-laminin chain is expressed as a fusion protein with a second different epitope tag. This permits multiple rounds of purification to be carried out. Alternatively, the same epitope tag can be used to create fusion proteins with more than one of the r-laminin chains.

In further embodiments, the epitope tag can be engineered to be cleavable from the r-laminin-521 chain(s). Alternatively, no epitope tag is fused to any of the r-Iaminin-521 chains, and the r-laminin-521 is isolated by standard techniques, including but not limited to affinity chromatography using laminin-521 specific antibodies or other laminin-521 binding molecules.

Media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin-521 secretion and/or activity, by any appropriate method, including Western blot analysis and cell binding assays.

In preferred embodiments, purification of r-laminin-521 is accomplished by passing media from the transfected cells through an antibody affinity column. In some embodiments, antibodies against a peptide epitope expressed on at least one of the recombinant chains are attached to an affinity column, and bind the r-laminin-521 that has been secreted into the media. The r-laminin-521 is removed from the column by passing excess peptide over the column. Eluted fractions are analyzed by any appropriate method, including gel electrophoresis and Western blot analysis. In further embodiments, the peptide epitope can be cleaved after purification. In other embodiments, two or three separate r-laminin chains are expressed as fusion proteins, each with a different epitope tag, permitting two or three rounds of purification and a doubly or triply isolated r-laminin-521. The epitope tag can be engineered so as to be cleavable from the r-laminin-521 chain(s) after purification. Alternatively, no epitope tag is fused to any of the r-laminin-521 chains, and the r-laminin-521 is isolated by standard techniques, including but not limited to affinity chromatography using laminin-521 specific antibodies or other laminin-521 binding molecules.

In other embodiments, purification of r-laminin-521 is accomplished by passing media from the transfected cells through a gel-filtration chromatography column. Eluted fractions are analyzed by any appropriate method, including gel electrophoresis and Western blot analysis. Fractions containing r-laminin-521 are collected and purity of the specimen is evaluated by any appropriate method, including gel electrophoresis and Western blot analysis. In some embodiments, the protein solution can be passed through a gel-filtration chromatography column again to gain higher purity of the protein. In some embodiments, to achieve higher purity of r-laminin-521 solution, the media or r-laminin-521 solution from the previous purification steps can be passed through an ion-exchange column. Eluted fractions are analyzed by any appropriate method, including gel electrophoresis and Western blot analysis. Fractions containing r-laminin-521 are collected and purity of the specimen is evaluated by any appropriate method, including mentioned above.

The laminin-521 polypeptide chains of the present disclosure also include (i) substitutions with one or more of the non-conserved amino acid residues, where the substituted amino acid residues may or may not be one encoded by the genetic code, or (ii) substitution with one or more amino acid residues having substituent groups, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

In particular embodiments, the isolated laminin-521 comprises three chains. The first chain comprises a polypeptide with at least 80% identity to a polypeptide sequence of SEQ ID NO: 1 (i.e. the α5 laminin chain). The second chain comprises a polypeptide with at least 70% identity to a polypeptide sequence of SEQ ID NO: 2 (i.e. the β2 laminin chain). The third chain comprises a polypeptide with at least 70% identity to a polypeptide sequence of SEQ ID NO: 3 (i.e. the γ1 laminin chain). These first, second, and third chains are assembled into recombinant laminin-521.

In more specific embodiments, the polypeptide of the first chain has at least 80% identity to the polypeptide sequence of SEQ ID NO: 1, the polypeptide of the second chain has at least 80% identity to the polypeptide sequence of SEQ ID NO: 2, and the polypeptide of the third chain has at least 80% identity to the polypeptide sequence of SEQ ID NO: 3.

In more specific embodiments, the polypeptide of the first chain has at least 90% identity to the polypeptide sequence of SEQ ID NO: 1, the polypeptide of the second chain has at least 90% identity to the polypeptide sequence of SEQ ID NO: 2, and the polypeptide of the third chain has at least 90% identity to the polypeptide sequence of SEQ ID NO: 3.

In particular embodiments, the first chain comprises the polypeptide sequence of SEQ ID NO: 1, the second chain comprises the polypeptide sequence of SEQ ID NO: 2, and the third chain comprises the polypeptide sequence of SEQ ID NO: 3.

In particular embodiments, the first chain is the polypeptide sequence of SEQ ID NO: 1, the second chain is the polypeptide sequence of SEQ ID NO: 2, and the third chain is the polypeptide sequence of SEQ ID NO: 3.

In other aspects, the present disclosure provides a new material, isolated laminin-521, which permits human embryonic stem cell survival after dissociation into single cell suspension. The stem cells were dissociated into single cell suspension by Trypsin-EDTA treatment, pelleted by centrifugation, resuspended into O3 medium, filtered through a 40 µm sieve, and plated at a density of 30 Kcells/cm$^2$ on cell culture dishes precoated by either isolated laminin-521, laminin-511, or Matrigel. After one day in culture, the cells plated on Matrigel died, as is known in the art. The human embryonic stem cells plated on laminin-521 and in most cases on laminin-511 survived and started to proliferate, forming small colonies of pluripotent cells.

In further aspects, the present disclosure provides a method to expand human embryonic stem cells in pluripotent state. It has been shown that human embryonic stem cells plated in single cell suspension on laminin-521 survived and proliferated at a higher rate than that of classical methods known in the art. After 3 passages (1 month) the cells passaged in a single cell suspension underwent the same number of cell divisions as that of cell cultures passaged in pieces on Matrigel after 20 passages (3 months). Therefore, the new method was advantageous in terms of time and labor, which may provide significant economical profits.

Laminin-521 is normally expressed and secreted by human pluripotent embryonic stem cells and can also be found in the kidneys, neuromuscular junctions, lungs, and placenta.

The availability of pure laminin-521 would enable studies of the effects of the protein on cellular differentiation and maintenance of cellular phenotypes. Thus, numerous research and therapeutic purposes including, but not limited to, treating injuries to tissues, promoting cell attachment, expansion and migration, ex vivo cell therapy, improving the biocompatibility of medical devices, and preparing improved cell culture devices and media, would be furthered if pure intact isolated laminin-521 were available. Also, the effects of pure laminin-521 on stem cells would be important to study as this protein is expressed in the early mammalian embryo.

Thus, there is a need in the art for isolated laminin-521 for research and therapeutic purposes, and methods for making isolated laminin-521. Laminin-521 can serve as a matrix for long-term self-renewal and fast multiplication of dissociated human ES and induced pluripotent stem (iPS) cells under completely chemically defined, feeder-free, and animal-protein-free (xeno-free) conditions. A LN-521 based system is easy to use and easy to automate, and allows fast scale-up of human ES/iPS cultures.

The present disclosure also relates to a cell culture medium that can be used to provide nutrition to cells, particularly stem cells. In this regard, stem cells typically require two things to be cultured: (1) a substrate or coating that provides a structural support for the stem cell; and (2) a cell culture medium to provide nutrition to the stem cell. The substrate or coating (1) is generally placed on, for example, a petri dish or some other container.

As used herein, the term "self-renewal" refers to the ability of the stem cell to go through numerous cycles of cell division and remain undifferentiated (i.e. pluripotent). Pluripotency itself refers to the ability of the stem cell to differentiate into any cell type. The term "proliferation" refers to the ability of the stem cell to divide. Survival refers to the ability of the stem cell to live, whether differentiated or undifferentiated, and does not require the stem cell to maintain its ability to divide or to differentiate.

The cell culture medium of the present disclosure is particularly suitable for being used with a substrate that contains laminin-521 and/or laminin-511. These laminins activate α6p1 integrins, which in turn leads to activation of the PI3K/Akt pathway. This increases the pluripotency, self-renewal, and/or proliferation of the stem cells. It is contemplated that the substrate may consist of laminin-521 or laminin-511, either intact, as separate chains, or as fragments thereof. Recombinant laminin-521 and recombinant laminin-511 are commercially available. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via α6p1 integrin, activating the PI3K/Akt pathway. The use of laminin-521 allows for single-cell suspension passaging without the addition of cell-detrimental rho-kinase (ROCK) inhibitor to increase cell survival after single-cell enzymatic dissociation. Previously, single-cell enzymatic passage of human ES cells without using artificial apoptosis inhibitors was impossible. The simplicity of the passaging procedure means the experimental variance is reduced and allows the process to be automated for high-throughput cell culture and results without the extensive training and costs of cell culture staff. In addition, human ES and iPS cells plated on laminin-521 or laminin-511 grow as a monolayer, which makes the culture homogeneous since cells are equally exposed to the matrix and the cell culture medium. Such human ES cell cultures, grown in a chemically defined, xeno-free environment on laminin-521, passaged as single cells in the absence of ROCK inhibitor expand continuously for months at an even better growth rate compared to cells grown on Matrigel passaged as clumps. These pluripotent long-term expanded cells homogeneously express Oct4 and remain karyotypically normal. Thus, one can obtain human ES and PS cells with sustained survival and proliferation capacity.

The average contact area and spreading homogeneity is much larger for cells cultured on laminin-511 compared to other available substrata. Human ES cells grown on laminin-511 over 3 months maintain pluripotency and can generate teratomas after engraftment into SCID mice. Laminin-511 also supports the self-renewal of mouse ES cells for over 5 months without the presence of LIF or feeder cells, when other known matrices are unable to do so for longer than a couple of weeks.

The cell culture substrate also comprises a cadherin. Cadherins are a class of type-1 transmembrane proteins that play important roles in cell adhesion, ensuring that cells within tissues are bound together. They are dependent on calcium ($Ca^{2+}$) ions to function. Cadherins are also known as desmogleins and desmocollins. Structurally, cadherins contain extracellular $Ca^{2+}$-binding domains. In particular embodiments, the cadherin used in the cell culture substrate is epithelial cadherin or e-cadherin.

The weight ratio of the laminin to the cadherin may be from about 5:1 to about 15:1, or from about 5:1 to about 10:1. In particular embodiments, the cell culture substrate consists of the laminin and the cadherin. In other specific embodiments, the laminin is laminin-521 and the cadherin is e-cadherin.

The stem cells to be grown with this cell culture medium can be induced pluripotent stem cells, embryonic stem cells, adult stem cells, fetal stem cells, amniotic stem cells, and generally any pluripotent stem cell.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Most generally, the cell culture medium of the present disclosure requires lower amounts of basic fibroblast growth factor (bFGF) than typically used. It is contemplated that the cell culture medium may comprise from greater than zero to 3.9 nanograms per milliliter (ng/mL) of bFGF. The bFGF is human bFGF so that the cell culture medium is totally human and defined. In some more specific embodiments, the cell culture medium may comprise 3.5 or lower ng/mL of bFGF. In other embodiments, the cell culture medium may comprise from 0.5 to 3.5 ng/mL of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E-01" should be interpreted as $4.1 \times 10^{-01}$.

TABLE 1

| Ingredient | molar mass (g/mol) | Min. Conc. (mM) | Max. Conc. (mM) | Min. Conc. (ng/mL) | Max. Conc. (ng/mL) |
|---|---|---|---|---|---|
| INORGANIC SALTS | | | | | |
| Calcium chloride (Anhydrous) | 110.98 | 4.1E−01 | 1.6E+00 | 4.6E+04 | 1.8E+05 |
| HEPES | 238.3 | 5.9E+00 | 1.8E+01 | 1.4E+06 | 4.2E+06 |
| Lithium Chloride (LiCl) | 42.39 | 4.9E−01 | 1.5E+00 | 2.1E+04 | 6.2E+04 |
| Magnesium chloride (Anhydrous) | 95.21 | 1.2E−01 | 3.6E−01 | 1.1E+04 | 3.4E+04 |
| Magnesium Sulfate (MgSO$_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate (NaHCO$_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate (NaH$_2$PO$_4$—H$_2$O) | 137.99 | 1.8E−01 | 5.3E−01 | 2.4E+04 | 7.3E+04 |
| TRACE MINERALS | | | | | |
| Ferric Nitrate (Fe(NO$_3$)$_3$—9H$_2$O) | 404 | 4.9E−05 | 1.9E−04 | 2.0E+01 | 7.5E+01 |
| Ferrous sulfate heptahydrate (FeSO$_4$—7H$_2$O) | 278.01 | 5.9E−04 | 1.8E−03 | 1.6E+02 | 4.9E+02 |
| Copper(II) sulfate pentahydrate (CuSO$_4$—5H$_2$O) | 249.69 | 2.0E−06 | 8.0E−06 | 5.1E−01 | 2.0E+00 |
| Zinc sulfate heptahydrate (ZnSO$_4$—7H$_2$O) | 287.56 | 5.9E−04 | 1.8E−03 | 1.7E+02 | 5.1E+02 |
| Ammonium Metavanadate NH$_4$VO$_3$ | 116.98 | 5.5E−06 | 1.6E−05 | 6.4E−01 | 1.9E+00 |
| Manganese Sulfate monohydrate (MnSO$_4$—H$_2$O) | 169.02 | 9.9E−07 | 3.0E−06 | 1.7E−01 | 5.0E−01 |
| NiSO$_4$—6H$_2$O | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate Na$_2$SiO$_3$—9H$_2$O | 284.2 | 4.8E−04 | 1.4E−03 | 1.4E+02 | 4.1E+02 |
| SnCl$_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| CdCl$_2$ | 183.32 | 6.1E−06 | 1.8E−05 | 1.1E+00 | 3.4E+00 |
| CrCl$_3$ | 158.36 | 9.9E−07 | 3.0E−06 | 1.6E−01 | 4.7E−01 |
| AgNO$_3$ | 169.87 | 4.9E−07 | 1.5E−06 | 8.3E−02 | 2.5E−01 |
| AlCl$_3$—6H$_2$O | 241.43 | 2.4E−06 | 7.3E−06 | 5.9E−01 | 1.8E+00 |
| Barium Acetate (Ba(C$_2$H$_3$O$_2$)$_2$) | 255.42 | 4.9E−06 | 1.5E−05 | 1.3E+00 | 3.8E+00 |
| CoCl$_2$—6H$_2$O | 237.93 | 4.9E−06 | 1.5E−05 | 1.2E+00 | 3.5E+00 |
| GeO$_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| ZrOCl$_2$—8H$_2$O | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-H$_2$O | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |

TABLE 1-continued

| Ingredient | molar mass (g/mol) | Min. Conc. (mM) | Max. Conc. (mM) | Min. Conc. (ng/mL) | Max. Conc. (ng/mL) |
|---|---|---|---|---|---|
| L-Cysteine-HCl—$H_2O$ | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |
| Glycine | 75.07 | 1.5E−01 | 4.4E−01 | 1.1E+04 | 3.3E+04 |
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| $B_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute.

In more specific embodiments, it is contemplated that the cell culture medium may not (1) contain albumin, (2) insulin or insulin substitute, (3) transferrin or transferrin substitute, or any combination of these three components.

It should be noted that other cell culture mediums may contain growth factors such as interleukin-1 beta (IL-1β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (µg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | µg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/mL) |
|---|---|
| Glycine | 7.50E+03 |
| L-Alanine | 8.90E+03 |
| L-Asparagine | 1.32E+04 |
| L-Aspartic acid | 1.33E+04 |
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/mL) |
|---|---|
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$—$5H_2O$) | 0.013 |
| Ferric Nitrate ($Fe(NO_3)_3$—$9H_2O$) | 0.5 |
| Ferric sulfate ($FeSO_4$—$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$—$H_2O$) | 625 |
| Zinc sulfate ($ZnSO_4$—$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

The combination of the laminin substrate with the cell culture medium of the present disclosure results in a cell culture system that can be cheaper, yet provides higher efficiency in maintaining pluripotent stem cells. In essence, all that is required is a laminin and a minimal amount of nutrition. It is particularly contemplated that the laminin used in combination with this cell culture medium is either LN-511 or LN-521.

The following examples are for purposes of further illustrating the present disclosure. The examples are merely illustrative and are not intended to limit devices made in accordance with the disclosure to the materials, conditions, or process parameters set forth therein.

EXAMPLES

Example 1

Cloning of the Human Laminin β2 cDNA

The 5.6 kb fragment of human laminin β2 cDNA was PCR-amplified from human liver cDNA library (BD Biosciences) using primers 5'-GTGGTACC-CACAGGCAGAGTTGAC-3' (SEQ ID NO: 7) and 5'-GCTCTAGAGCTCTTCAGTGCATAGGC-3' (SEQ ID NO: 8) thus introducing artificial XbaI and KpnI cutting sites on the ends of the fragment. To decrease the error rate during the PCR amplification, Phusion™ high-fidelity PCR Kit (Finnzymes) was used.

Subsequently, the fragment was digested with XbaI and KpnI and subcloned into pSK vector digested with the same restriction endonucleases (pSKHLAMB2 plasmid). To verify the integrity of the sequence, several clones of pSKHLAMB2 plasmid were sequenced. Sequencing was performed on an ABI PRISM™ 310 Genetic Analyzer (Perkin Elmer) using ABI PRISM® BigDye™ Terminator Cycle Sequencing kit (PE Applied Biosystems). Only complete matches with the NCBI database human laminin β2 sequence were selected for further cloning.

Expression Constructs

For expression of the human laminin β2 chain pSKHLAMB2 plasmid was digested with XbaI and KpnI and subcloned into XbaI-KpnI treated pcDNA 3.1(+) vector (Invitrogen).

The constructs used for expression of human laminin α5 (HLN5Full.pcDNA construct) and γ1 (HG1 construct) have been described previously (Doi, M. et al., J. Biol. Chem. 277(15), 12741-8 (2002)).

Antibodies

Anti-laminin β2 (MAB2066) monoclonal antibody (mAb) was purchased from R@D Systems. Anti-laminin α5 mAb (2F7) was purchased from Abnova. Anti-laminin β1 mAb (MAB1921) was purchased from Chemicon. Anti-laminin γ1 (H-190) rabbit polyclonal antibody was purchased from Santa Cruz Biotechnology, Inc.

Production and Purification of Recombinant Laminin-521 r-laminin-521 was produced in human embryonic kidney cells (HEK293, ATCC CRL-1573) cultured in DMEM, 10% FCS in humidified 5% $CO_2$ atmosphere at 37° C. Wild-type cells were transfected using the standard calcium-phosphate method with the HG1 construct and stable colonies were selected using 100 mg/ml hygromycin (Cayla). All further cell culture and clonal expansion was carried out in continuous presence of relevant selection antibiotics. A highly expressing clone was then transfected with the human laminin β2 construct and stable clones were selected using 500 mg/ml G418 (Life Technologies). A clone highly expressing both laminin γ1 and laminin β2 was finally transfected with the HLN5Full.pcDNA construct and stable colonies were selected using 200 mg/ml zeocin (Cayla). The clones showing the highest secretion were expanded further.

For production of r-laminin-521, confluent cells were cultured in DMEM for up to five days. r-laminin-521 was affinity purified using anti-FLAG M2 matrix (Sigma). The collected medium was incubated in batch mode with the matrix overnight at 4° C. with agitation. Bound r-laminin-521 was competitively eluted with 50 mg/ml FLAG peptide (Sigma) in TBS/E (50 mM Tris-Cl, pH 7.5, 150 mM NaCl, 1 mM EDTA) at room temperature. The elute was concentrated and the buffer was replaced by PBS using 30 kD cut-off ultrafiltration (Millipore). Finally the concentrated solution was passed through 0.2 mm filter to remove self-aggregated polymers.

Characterization of Recombinant Laminin-521

Figure 3:
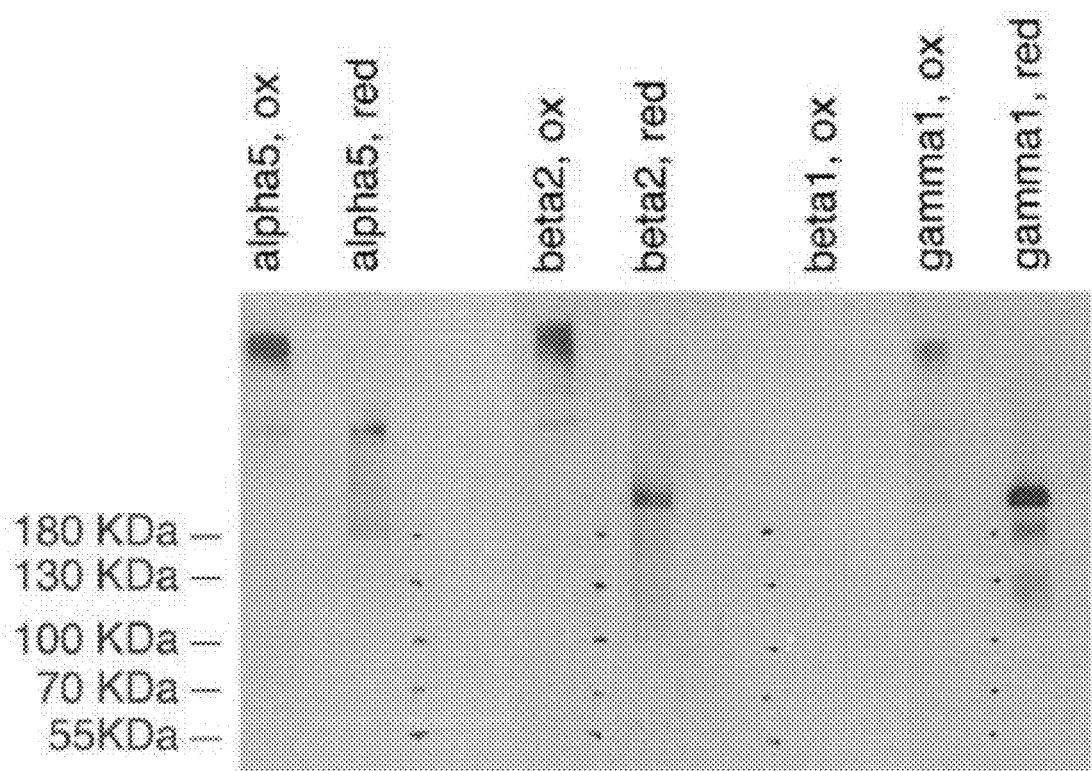
FIG. 3 shows the results of characterization of human recombinant laminin-521 using SDS-PAGE. An immunoblot of recombinant laminin-521 was made under non-reducing (labeled as ox) and reducing (labeled as red) conditions. Proteins on 3-8% gels were transferred onto PVDF membranes followed by staining with antibodies to laminin α5 (2F7), β2 (MAB2066), β1 (MAB1921) and γ1 (H-19).

Secreted laminin in medium and after purification was characterized using 3-8% gradient SDS-PAGE. Proteins were visualized using Sypro staining (Bio-Rad) or transferred onto PVDF (FIG. 3). The membranes were probed with antibodies described above. After washing, the membranes were incubated with HRP-conjugated goat antibodies. The immunoreactivity was detected by a chemiluminescent kit (Life Science Products) according to the manufacturer's instructions.

Methods

Human ES Cell Cultures.

Human ES cells were cultured on r-laminin-521-coated laboratory dishes in chemically defined O3 medium (described in Rodin et al., Nature Biotechnol., vol. 28, pp. 611-615 (2010)) at 37° C. in 5% $CO_2$. Cells were routinely passed once every 10-12 days by exposure to Trypsin-EDTA solution (GIBCO Invitrogen) for 5 minutes at 37° C. They were then gently pipetted to break into single-cell suspension and defined trypsin inhibitor (GIBCO Invitrogen) was added. The cell suspension was centrifuged at for 4 minutes, the supernatant discarded, the cell pellet resuspended in prewarmed O3 medium, and cells were then passed through a 40 μm sieve. After that cells were plated on new r-laminin-521-coated dishes at a concentration 30 Kcells/$cm^2$ (1:25-1:30 split ratio). Cells were fed once a day with fresh medium prewarmed in an incubator for 1 hour, except for the first day after a passage, when only a few drops of fresh medium were added. Control cells of the same line were cultured on Matrigel (BD Biosciences) in O3 medium as described in Rodin et al., Nature Biotechnol., vol. 28, pp. 611-615 (2010). Control cells were passaged in pieces.

Cell Culture Dish Coating.

Ninety-six-well tissue cell culture plates were coated overnight at 4° C. with sterile solutions of the ECM proteins mouse LN-111 (Invitrogen), human recombinant LN-511, and human recombinant LN-521, all at a concentration of 30 μg/ml (5 μg/$cm^2$). For control cells, BD Matrigel™ hESC qualified (BD Biosciences) was used according to the manufacturer's instructions.

Cell Adhesion Assay.

The assay was performed as described (Extracellular Matrix Protocols, 2000). Briefly, 96-well plates were coated by extracellular matrix proteins as described above and blocked by O3 medium containing bovine serum albumin. The ES cells were plated at a cell density of 600 cell/$mm^2$ upon extracellular matrix-coated plates and were left to adhere for either 1 hour or 1 day at the cell incubator. Non-adherent cells were washed away, and adherent cells were fixed for 20 min by 5% glutaraldehyde, stained by 0.1% Crystal Violet.

Real-Time PCR Quantification of mRNAs.

Total RNA was isolated and cDNA was synthesized as described in Rodin et al., Nature Biotechnol., vol. 28, pp. 611-615 (2010). Real-time quantitative RT-PCR Taqman assays were performed using the Applied Biosystems 7300 Real-Time PCR System. All reactions were done in quadruplicate with predeveloped gene expression assay mix (Applied Biosystems) containing primers and a probe for the mRNA of interest. Additional reactions for each experiment included predeveloped gene expression assay mix for GAPDH, used to normalize the RNA input. All data were analyzed with 7300 System SDS Software version 1.4.

Facs Analysis.

OCT4 expression was analyzed as described in Ludwig, T. E. et al. Derivation of human embryonic stem cells in defined conditions. Nat. Biotechnol. 24, 185-187 (2006). Cells were run on FACSCalibur Flow Cytometer (Becton Dickinson). Data were analyzed with CellQuest software (Becton Dickinson).

Results for Example 1

Figure 4:
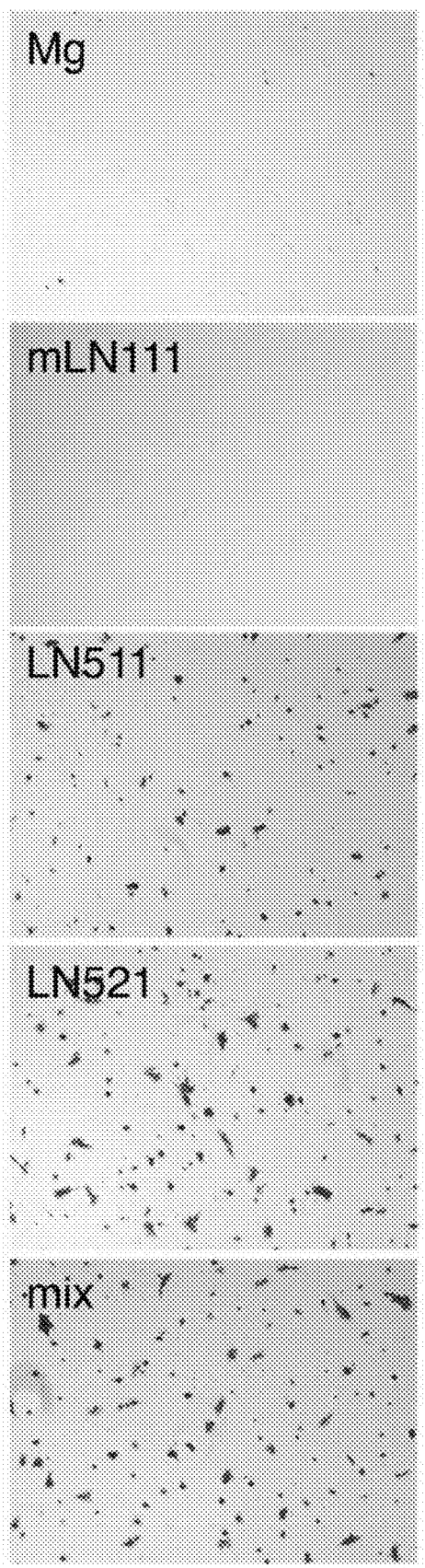
FIGS. 4 and 5 show the Crystal Violet staining of human ES cells adherent to dishes coated in Matrigel (Mg), mouse laminin-111 (mLN111), human recombinant-laminin-511 (r-laminin-511 or r-LN-511), human recombinant-laminin-521 (r-laminin-521 or r-LN-521), or a mixture of r-laminin-511 and r-laminin-521 (mix) after one day in culture. Both Figures are magnified 5×.

To find out how different cell culture coatings affect single cell survival of human ES cells in O3 medium without any additives, we completely dissociated HS181 cells and plated them on either Matrigel, mouse laminin-111, human r-laminin-511, human r-laminin-521, or a mixture of r-laminin-511 and r-laminin-521. The results are seen in FIG. 4. As expected, almost no cells remained attached to Matrigel or mouse laminin-111 by 24 hours after plating. In contrast, the cells on human r-laminin-521, the mixture, and at a less extent on human r-laminin-511 survived.

Figure 5:
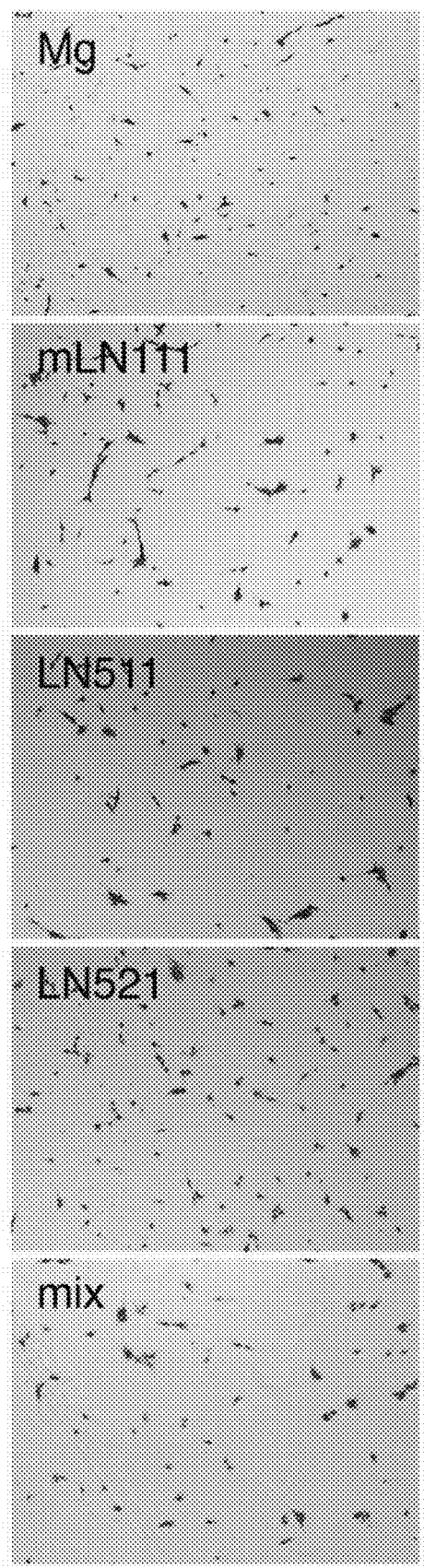

The experiment was repeated on human ES cells in O3 medium treated with ROCK inhibitor Y-27632. These results are seen in FIG. 5. The stem cells remained attached on all 5 coatings.

Figure 6:
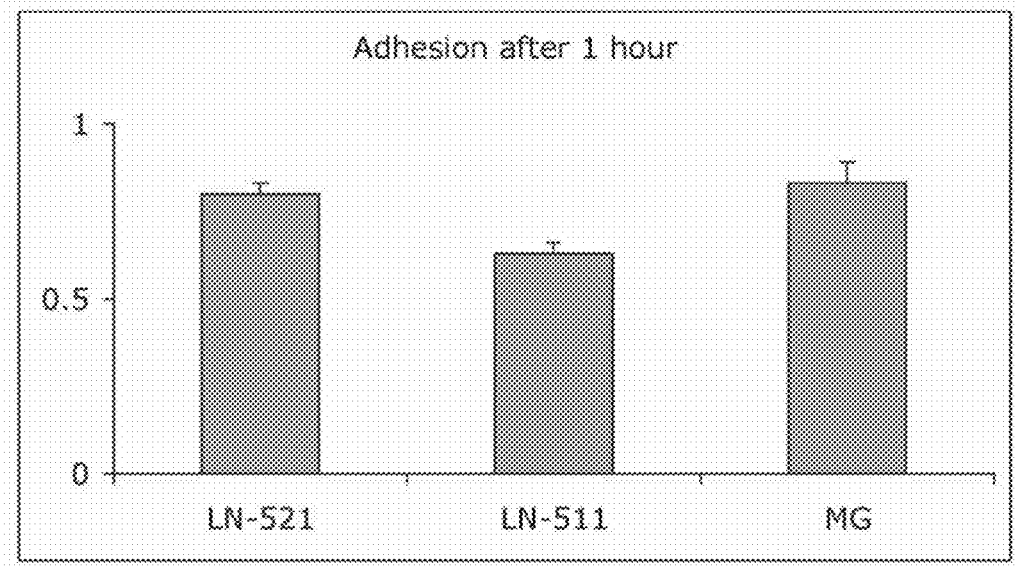
FIG. 6 is a graph showing the adhesion of human ES cells to human r-laminin-521 (labeled as LN521), human r-laminin-511 (LN511), and Matrigel (Mg) coated dishes after one hour in culture without ROCK inhibitor. Error bars show the standard error of measurement. (n=3).

To quantify this effect, we performed cell adhesion experiments on all of the above-mentioned coatings at 1 hour and 1 day after plating (i.e., each of the five coatings, with and without Y-27632). FIG. 6 shows the results for the 1-hour experiment for LN-521, LN-511, and Matrigel (MG) without Y-27632. The adhesion of human ES cells in O3 medium without any additives was roughly the same at this time point.

Figure 7:
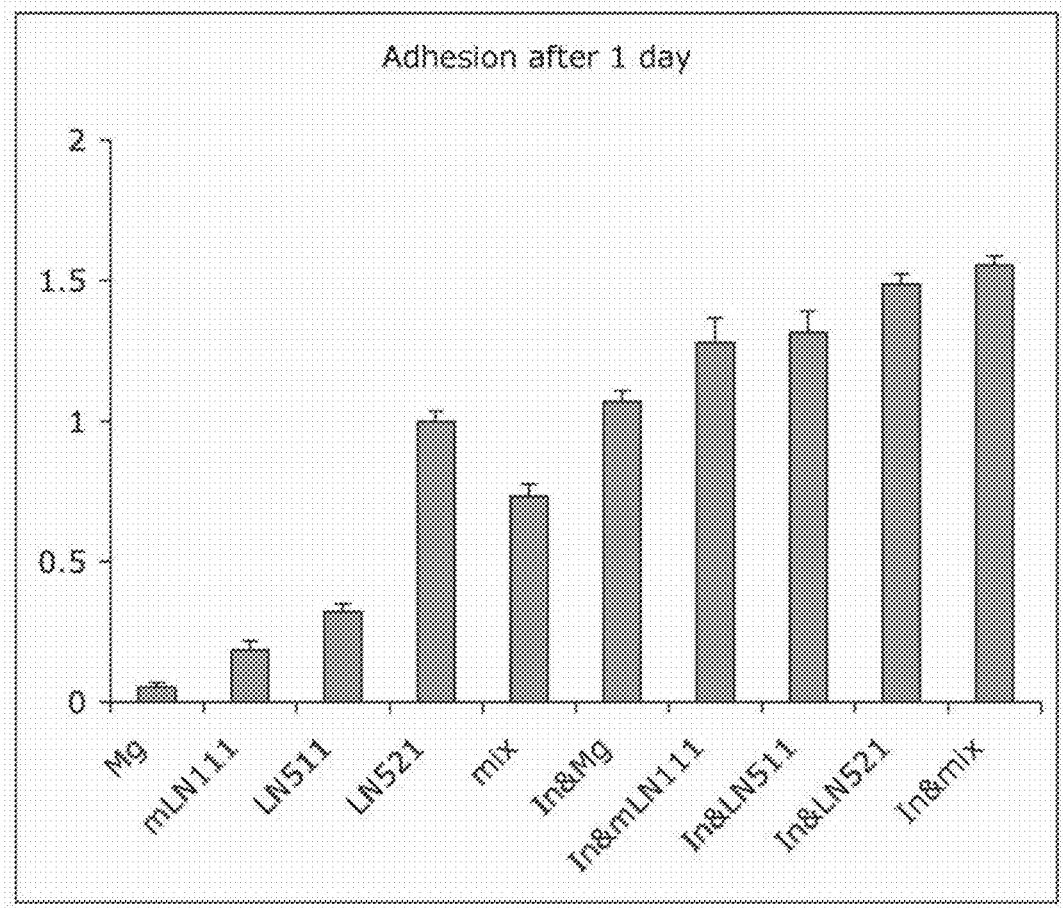
FIG. 7 is a graph showing the adhesion of human ES cells to dishes coated in either Matrigel (Mg), mouse laminin-111 (mLN111), human r-laminin-511 (LN511), human r-laminin-521 (LN521), or a mixture of r-laminin-511 and r-laminin-521 (mix), after one day in culture and without ROCK inhibitor. Also included are results for dishes with ROCK inhibitor and either Matrigel (In&Mg), mouse laminin-111 (In&mLN111), human r-laminin-511 (In&LN511), human r-laminin-521 (In&LN521), or a mixture of r-laminin-511 and r-laminin-521 (In&mix), also after one day in culture. The cells for both experiments were plated at the same density on the same cell culture dish. Error bars show standard error of measurement (n=3).

FIG. 7 shows the results for the 1-day experiment for all of the coatings. The plates containing the Y-27632 inhibitor are labeled as "In&" along with the coating. At 1 day after plating, the stem cells adhered to LN-521 without additives 20 times better than to Matrigel without additives. In addition, the results showed that the adhesion of cells to LN-521 without additives was similar to the adhesion of cells on all dishes including the ROCK inhibitor. In other words, no ROCK inhibitor is necessary with LN-532 coating to obtain results similar to coatings that do contain the ROCK inhibitor.

Figure 8:
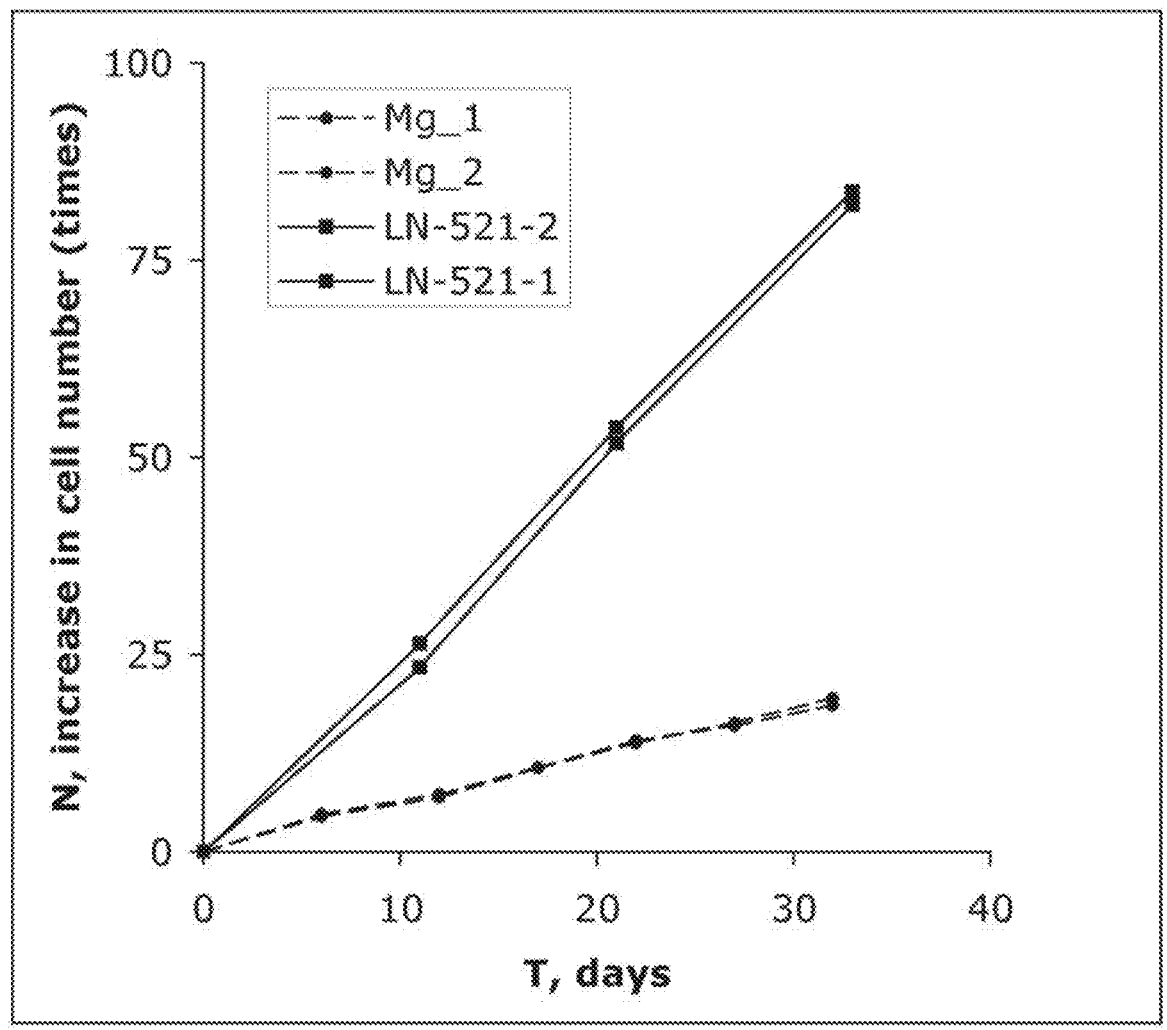
FIG. 8 shows the growth curves for human ES cells cultured on r-laminin-521 (LN-521_1 and LN-521_2) using single cell dissociation passaging and for human ES cells cultured on Matrigel (Mg_1 and Mg_2) using passaging in small clumps. The latter cells were passaged as described in Rodin et al., *Nature Biotechnol.*, vol. 28, pp. 611-615 (2010).

We cultured human ES cells on human r-laminin-521. passaging them after complete dissociation into single cell suspension every 10-12 days in 1:25 to 1:30 ratios. The cells proliferated robustly with a stable and high rate for at least 9 passages (3 months). Moreover, after 3 passages (1 month), they underwent the same number of cell doublings as stem cells after 20 passages (100 days) cultured using conventional methods. This is illustrated in FIG. 8, which shows the increase in the number of cells versus time. The cells on LN-521 increased at a much faster rate than on Matrigel. Thus, the new r-laminin-521 hES cell culture method was advantageous in terms of time and labor.

Figure 9:
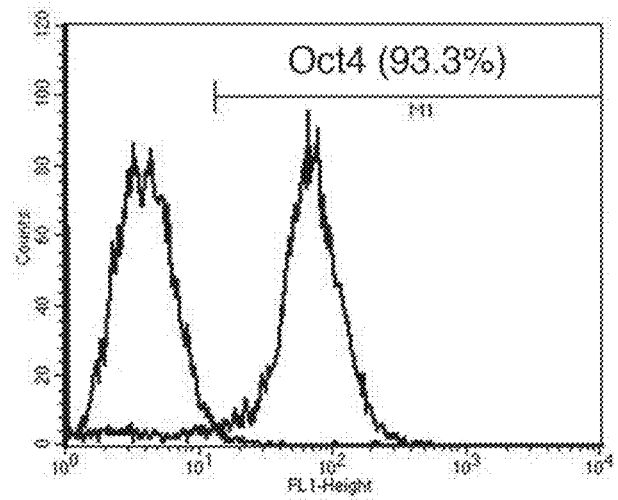
FIG. 9 is a FACS analysis of human ES cells after several single cell dissociation passages on r-laminin-521 for OCT4, a marker of pluripotency. The percentage of positive cells is listed in parentheses.
Figure 10:
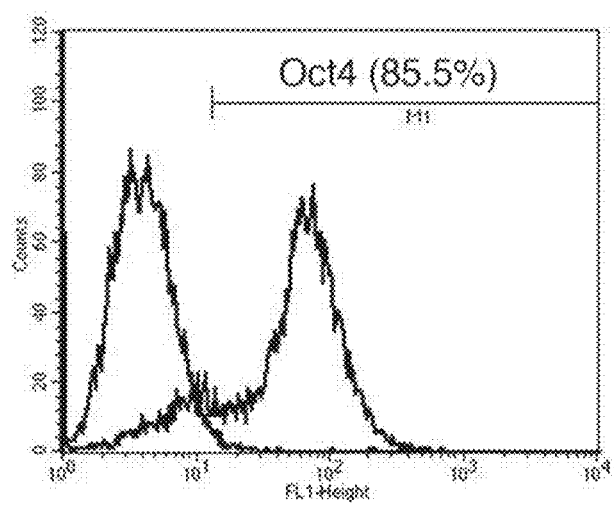
FIG. 10 is a FACS analysis of human ES cells after several passages on Matrigel using splitting in small clumps for OCT4. The percentage of positive cells is listed in parentheses.

To confirm the identity of hES cells after several single cell suspension passages on human r-laminin-521 in O3 medium without any additives, we performed FACS analysis for Oct4, a marker of pluripotency. FIG. 9 shows the results for cells grown on r-LN-521, while FIG. 10 shows the results for cells grown on Matrigel. The percentage of positive cells is listed in parentheses. R-LN-521 had a much higher percentage of pluripotent cells.

Figure 11:
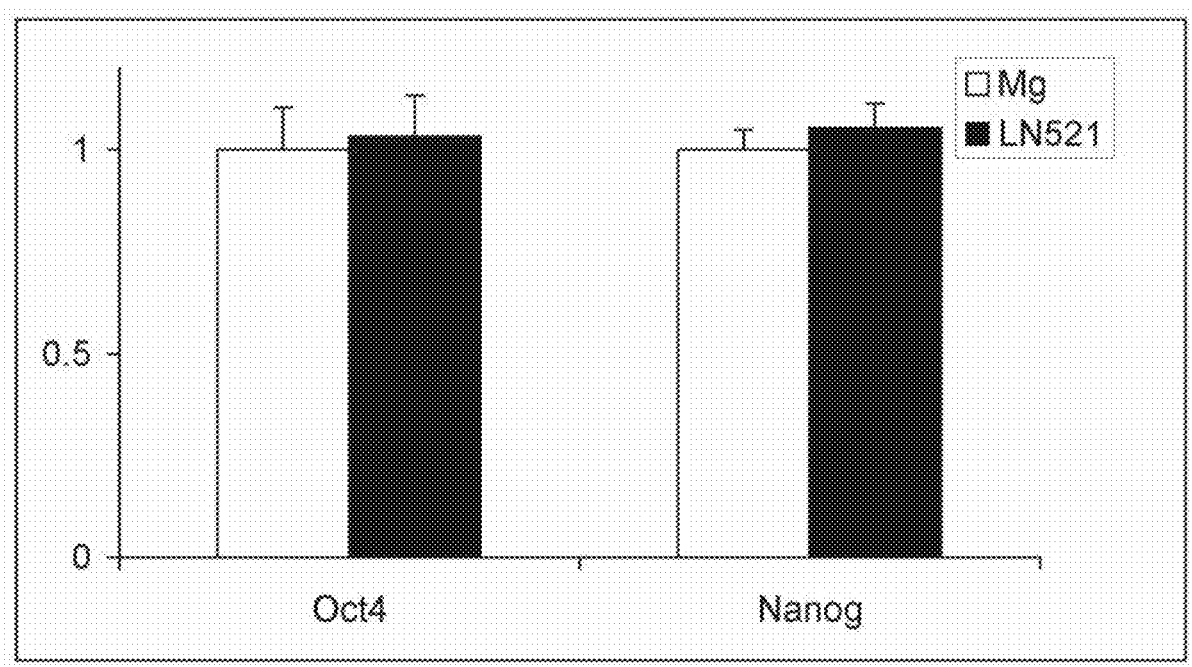
FIG. 11 shows the results of a real-time quantitative RT-PCR analysis which was used to compare numbers of mRNA transcripts of the pluripotency markers Oct4 and Nanog in human ES cells cultured on human r-laminin-521 (LN521) after several single cell dissociation passaging and in the cells cultured on Matrigel (Mg) after several passaging of the cells in clumps. Error bars show 95% confidence intervals.

In addition, the number of mRNA transcripts of the pluripotency markers Oct4 and Nanog was quantified. FIG. 11 shows these results. For both markers, the cells on LN-521 showed higher numbers of transcripts.

Both methods showed that the new methods provides hES cells of the same or better quality than the current method, which uses Matrigel as a cell culture dish coating material and passaging of the cells in small clumps.

Example 2

In this Example 2, expressed and purified recombinant LN-521 that was also expressed in pluripotent hES cells was studied for its effects on cultured hES and PS cells. The results showed that LN-521, alone, strongly supports self-renewal of pluripotent hES and PS cells, and, importantly, it allows survival of pluripotent stem cells following plating of trypsinized stem cells in single cell suspension on LN-521 at high dilutions. The effects of LN-521 were shown to be mediated by signaling via α6β1 integrin through induction of hES cell migration and PI3K/Akt pathway activation. The results may be applied for an effective and even automated expansion method for large-scale production of pluripotent hES and iPS cells, as well as for development of new medium formulations for self-renewal of pluripotent stem cells. The new hES/hiPS cell culture method described here closely resembles standard cell culture methods, e.g. that are used to culture fibroblasts, and, therefore, it does not demand special skills. It consumes significantly less cell coating material per one cell division and is time efficient, thus providing significant economical profits in comparison with the previous procedures for culturing hES/hiPS cells.

Human recombinant LN-521, which has previously not been available in pure form, was produced by cloning full-length laminin p32 cDNA and carrying out a triple-transfection of HEK293 cells with the human laminin α5, β2 and y1 chains. Human recombinant LN-111 and LN-121 were similarly generated following cloning of full-length α1 and β2 chain cDNAs and triple transfection of HEK293 cells with human α1, β1 and γ1 and α1, β32 and γ1 chain cDNAs, respectively. The purified LN-521, LN-111 and LN-121 proteins were shown to contain, respectively, pure α5, β2, and γ1 chains, α1, β1 and γ1 chains, as well as α1, β32 and γ1 chains, as shown by protein staining and Western blot analysis.

Methods

Human ES and iPS Cell Cultures.

Human ES cells of HS181 and HS401 were cultured on LN-521-coated culture dishes in O3 medium (described in Rodin et al., *Nature Biotechnol.*, vol. 28, pp. 611-615 (2010) with pH was adjusted to 7.35), mTeSR1 (STEMCELL Technologies) and chemically defined and xeno-free TeSR2 (STEMCELL Technologies) at 37° C., 5% $CO_2$. Initially, cells of the lines were transferred onto a LN-521 coating from a human feeder cell layer by careful scratching using a sterile knife with subsequent trypsinization, or the cells were trypsinized into single cell suspension from a LN-511 coating. The cells were provided once a day with fresh medium pre-warmed in an incubator for one hour, except for the first day after plating, when only a few drops of fresh medium were added. Cells were routinely passed once in 10-12 days by exposure to Trypsin/EDTA (GIBCO Invitrogen Corporation, Paisley, Scotland) for 5 minutes at 37° C., 5% $CO_2$. They were then gently pipetted to break into single-cell suspension and a Defined Trypsin Inhibitor (GIBCO Invitrogen) was added. The cell suspension was centrifuged at 25 rcf for 4 minutes, the supernatant was discarded, the cell pellet was resuspended in prewarmed O3 medium, and the cells were then passed through a 40 μm sieve. Subsequently, the cells were plated on new LN-521-coated dishes at a concentration of 30,000 cells/cm² in 1:25-1:30 split ratios. Control cells of the same line were cultured on Matrigel (STEMCELL Technologies) and LN-511 in O3 medium as described previously.[9]

For defined and xeno-free cultures, TeSR2 (STEMCELL Technologies) medium and defined free from any animal derived component TrypLE™Select (GIBCO Invitrogen Corporation, Paisley, Scotland) enzyme were used. The cells were passed every 10-14 days by exposure to TrypLE™Select for 4-5 minutes at 37° C., 5% $CO_2$. Then, the enzyme was carefully aspirated and prewarmed TeSR2 medium was added. After that, the cells were gently pipetted to break into single-cell suspension, centrifuged, the supernatant was discarded, and the cell pellet was resuspended in prewarmed TeSR2. The cells were then passed through a 40 μm sieve and plated on a fresh LN-521 coated dish.

Tissue cell culture plates were coated overnight at 4° C. with sterile solutions of the ECM proteins, such as human recombinant LN-521, all at a concentration of 30 μg/ml (5 μg/cm²). Control plates were coated with Matrigel according to the STEMCELL Technologies' instructions. Prior to use, dishes were pre-warmed in an incubator for one hour after which prewarmed O3 medium was added without additional washing of the dish. After applying a fresh LN-521 solution to a new dish, the remaining LN-521 solution could be used at least once more. All the adhesion, survival, and inhibition of survival experiments were carried out using fresh coating materials.

The human iPS cells, ChiPSW line, were derived from lentivirally transduced human foreskin fibroblasts (HFF) with OCT-4/SOX2/NANOG/LIN28 reprogramming genes. The ChiPSW line had normal male karyotype, 46,XY, in repeated testing at different passages. Prior to cell culture and passaging experiments, the cells were first characterized in vitro for expression of pluripotency markers. Immunofluorescence study with antibodies against Oct3/4 (SC-5279), Nanog (SC-33759), TRA-1-60 (SC-21705) and SSEA4 (sc-21704) showed that the cells expressed all those markers of pluripotency. RT-PCR analysis confirmed that the cells lacked expression of the viral transgenes. The pluripotency of ChiPSW cells was confirmed by in vitro (embryoid bodies formation and immunofluorescence study) and in vivo (injection subcutaneously into SCID beige mice) experiments. Cells of ChiSW line could be further differentiated into beating cardiomyocytes. They were also capable of undergoing hematopoietic differentiation.

Before taken to the present feeder free cultures, the iPS cells were maintained and expanded over irradiated human foreskin fibroblasts. Knock-out serum (KS, Invitrogen)-supplemented media was used for propagation, supplemented with 8 ng/ml of basic fibroblast growth factor (bFGF, R&D Systems). Cells were fed on a daily basis and weekly passaged using collagenase IV (1 mg/ml, Roche) or manual dissection when required.

Prior to these experiments, the CutB1.2 cells were shown to express pluripotency markers Oct4/Nanog/Sox2/TRA-1-60/TRA-1-81, to lack expression of the viral transgenes, and the pluripotency of the cells was confirmed both by in vivo and in vitro differentiation studies.

Laminin-521 and Other Coating Materials.

Human recombinant LN-521, available from BioLamina, AB, Stockholm (www.biolamina.com), was produced in human embryonic kidney cells (HEK293; ATCC CRL-1573) sequentially transfected with full-length laminin γ1, β2 and α5 constructs essentially as described previously. For protein production, the HEK293 cells were cultured in Dulbecco's modified Eagle's medium (DMEM) supplemented with GlutaMax I for up to six days. The LN-521 molecules were affinity-purified using anti-FLAG matrix (Sigma), and then characterized using 3-8% and 4-15% gradient SDS-PAGE under reducing and nonreducing conditions. The proteins were visualized using Sypro Ruby (Bio-Rad) protein staining and immunostaining of the chains on polyvinylidene difluoride membranes. To further characterize the protein, Western blot analysis with antibodies against the laminin α5, β2 and γ1 chains was performed. Human recombinant laminin-111 and laminin-121 were produced similarly to LN-521 and shown to contain the correct chains of predicted molecular sizes by Western and SDS-PAGE. If not otherwise stated, the corresponding mouse laminin-111 (Invitrogen) was indicated as LN-111.

Reagents and Antibodies.

InSolution™ LY 294002 (a specific Akt inhibitor), InSolution™ Wortmannin (a specific PI3K inhibitor), and InSolution™ 98059 (a specific MEK1/Erk inhibitor) were purchased from Calbiochem. Antibodies to phospho-Akt (#4060), total-Akt (#9272), phospho-Erk (#9101), and total-Erk (#9102) were obtained from Cell Signaling Technology. PathScan Phospho-Akt1 sandwich ELISA kit (#7160), PathScan total Akt1 sandwich ELISA kit (#7170), PathScan Phospho-Akt2 sandwich ELISA kit (#7048), and PathScan total Akt2 sandwich ELISA kit (#7046) were also purchased from Cell Signaling Technology. Antibodies to Calnexin (#ab10286) were obtained from Abcam. Function blocking antibodies to various integrin subunits, mouse isotype antibodies, and α-dystroglycan were purchased from Millipore. Since function blocking antibodies to αV (MAB1980) and α6 (MAB1378) were presented in a solution with sodium azide, before the inhibition of survival experiment all the antibodies to alpha integrin subunits were dialyzed thrice against O3 medium for 2 hours each time. Antibodies to Lutheran receptor and α-fetoprotein, as well as rat isotype control antibodies were obtained from R&D Systems. Antibodies to Oct4, Nanog, SSEA-4, smooth muscle actin and MAP-2 were purchased from Millipore.

Immunofluorescence.

For immunofluorescence studies, ES cells were cultured and fixed in 8-well slide chambers (BD Biosciences) or 96-well plate wells by 4% paraformaldehyde, permeabilized by 0.1% Triton-X and blocked by 10% bovine fetal serum (GIBCO Invitrogen Corporation) in phosphate-saline buffer (PBS) containing 0.1% Tween-20 (Sigma-Aldrich, St. Louis, http://www.sigmaaldrich.com) for one hour. Incubation with primary antibody was performed for 1.5 hours at room temperature. Incubation with secondary antibody and 4,6-diamidino-2-phenylindole (DAPI, Molecular Probes) was performed for 40 minutes. Between incubations, the specimens were washed with 0.1% Tween-20 in PBS buffer three to five times. Specimens were preserved in a fluorescence mounting medium (Dako, Glostrup, Denmark, http://www.dako.com), and observed under a fluorescence microscope (Leica, Heerbrugg, Switzerland, http://www.leica.com).

Real-Time PCR Quantification of Different mRNAs.

Total RNA was isolated using Absolutely RNA Microprep Kit (Stratagene, La Jolla CA, www.stratagene.com) according to the manufacturer's instructions. cDNA was synthesized using 0.2 μg of total RNA in 20 μl reaction mixture, containing oligo(dT)12-18 primers and Superscript II reverse transcriptase (GIBCO Invitrogen Corporation), according to the manufacturer's instructions. Real-time quantitative RT-PCR Taqman assays were performed using the Applied Biosystems 7300 Real-Time PCR System (Applied Biosystems, Foster City, CA). All reactions were done in quadruplicates with the use of a pre-developed gene expression assay mix (Applied Biosystems) containing primers and a probe for the mRNA of interest. Additional reactions for each experiment included pre-developed gene expression assay mix for GAPDH for normalizing the RNA input. All data was analyzed with 7300 System SDS Software v 1.4.

Facs Analysis.

Cells were removed from the culture dish with Trypsin/EDTA, dissociated into single cell suspension and resuspended in ice-cold FACS buffer (2% fetal bovine serum, 0.1% sodium azid in Hank's buffer). Incubation with primary antibodies against SSEA-4 (from Millipore, Billerica, MA, http://www.millipore.com) was performed for one hour on ice. Then, the cells were washed three times with ice-cold FACS buffer. Subsequently, the cells were probed in FACS buffer with 1:400 dilution of Alexa Fluor anti-mouse secondary antibodies (GIBCO Invitrogen Corporation) for 30 minutes in the dark, and washed four times. Control cells were incubated with mouse immunoglobulins and, subsequently, with the secondary antibody as described above. Cells were analyzed on FACSCalibur Flow Cytometer (Becton Dickinson, San Jose, CA). Data were analyzed with the CellQuest software (Becton Dickinson).

Karyotyping.

Karyotyping of the cell lines was carried out using standard Q-banding techniques. Samples of cells were treated with colcemid KaryoMAX (0.1 μg/ml; Gibco Invitrogen Corporation) for up to 4 hours, followed by dissociation with Trypsin/EDTA solution (Gibco Invitrogen Corporation). The cells were pelleted via centrifugation and re-suspended in pre-warmed 0.0375 M KCl hypotonic solution and incubated for 10 minutes. Following centrifugation, the cells were resuspended in fixative (3:1 methanol:acetic acid). Metaphase spreads were prepared on glass microscope slides and G-banded by brief exposure to trypsin and stained with 4:1 Gurr's/Leishmann's stain (Sigma-Aldrich Co.). A minimum of 10 metaphase spreads were analyzed and additional 20 were counted.

Teratoma Formation.

Teratoma formation experiments were performed by implantation of approximately $10^6$ cells beneath the testicular capsule of a young (7-week-old) severe combined immunodeficiency (SCID) mouse. Three animals per each cell line were used. Teratoma growth was observed by weekly palpation, and the mice were sacrificed eight weeks after the implantation. The teratomas were fixed, and sections were stained with hematoxylin and eosin (HE) or with hematoxylin, eosin and PAS (HE-PAS). The presence of tissue components of all three embryonic germ line layers was demonstrated, as analyzed from the stained sections. All animal experiments were performed at the infection-free animal facility of the Karolinska University Hospital in accordance with ethical committee approval.

Embryoid Body Formation.

ES cells from LN-521 coated cell culture dishes were exposed to TrypLE™Select for one minute at 37° C., 5% $CO_2$, washes two times with a medium, broken into large pieces and cultured in suspension in low adhesion plates. The medium used for this was Knockout DMEM (GIBCO Invitrogen Corporation) supplemented with 2 mM L-glutamine, 20% fetal calf serum (GIBCO Invitrogen Corporation), 0.1 mM β-mercaptoethanol (GIBCO Invitrogen Corporation) and 1% non-essential amino acids (GIBCO Invitrogen Corporation). After 1-2 weeks in suspension, the embryoid bodies were transferred onto gelatin coated tissue cell culture 96-well plates (Sarstedt), cultured for 1-2 weeks, then fixed, stained with antibodies against markers of all three embryonic germ line layers (smooth muscle actin, MAP-2 and α-fetoprotein) and analyzed as described above for immunofluorescence.

Cell Adhesion Assay.

Briefly, 96-well plates were coated by extracellular matrix proteins as described above and blocked by O3 medium containing bovine serum albumin. The ES cells were plated at cell density of 50,000 cells/cm$^2$ onto extracellular matrix-coated plates and left to adhere for 1 hour in a cell incubator. After that the plates were washed 3 times with the medium to remove the non-adherent cells, and then the adherent cells were fixed for 20 minutes by 5% glutaraldehyde, stained by 0.1% Crystal Violet. (Kebo Lab, Spanga, Sweden, http://www.kebolab.se). After one hour and 3 washes with water, Crystal Violet was extracted with 10% acetic acid and quantified by measuring optical density at 570 nm. All the experiments were performed in quadruplicate.

Cell Survival and Inhibition of Survival Assays.

The survival assay was performed as described for the cell adhesion assay above, except that the cells were left in the cell incubator for 24 hours. For inhibition of survival assay, the cells were kept in a medium with function blocking antibodies at the concentrations recommended by the manufacturer or pathway inhibitors at concentrations indicated in the text for 30 minutes, and then plated on the coated dishes. All the experiments were performed in quadruplicate.

Western Blotting and ELISA.

HS 181 cells were trypsinized into single cell suspension as described above. For inhibition experiments, the cells were kept in O3 medium with blocking antibodies or pathway inhibitors for 30 minutes and then 450K cells were plated on 35 mm dishes precoated with the appropriate matrix coating. For other experiments, same number of cells was plated directly after trypsinization. In all cases the cells were allowed to spread for 1 hour at 37° C., 5% $CO_2$. After two washings in ice-cold PBS, the plates with cells were snap frozen in liquid nitrogen and stored at −80° C. To prepare samples for western blots and ELISA, the plates were slowly thawed and kept on ice with 100-150 µl of lysis buffer (50 mM Tris-HCl, pH7.5, 150 mM NaCl, 0.5% deoxycholate, 0.5% SDS, 1% Triton X-100, 1% Igepal, Complete™ (Roche) and Phospho-Stop™ (Roche)) on top. Then, the cells were scraped, pipetted and sheared through a 27G 3/4" needle. After that, the cell pellets were clarified by centrifugation at 16,100 rcf for 15 minutes at 4° C. For western blots, 4-12% gradient gels were used for SDS electrophoresis and the proteins were transferred to PVDF membranes. The membrane was hybridized with the antibody of interest according to the manufacturer's instructions. Chemoluminescent HRP-substrate from Amersham Biosciences was used for visualization. For the densitometry analysis the films were scanned at 2,400 dpi and analyzed by the Chemilmager5500 program (1 D-Multi Line densitometry mode). For ELISA the samples were applied to the wells according to the manufacturer's instructions.

In Vivo Imaging and Migration Assay.

24-well plates were coated by extracellular matrix proteins and blocked by O3 medium containing bovine serum albumin. The ES cells were plated at cell density of 30,000-40,000 cells/cm$^2$ onto extracellular matrix-coated plates and left to adhere for half an hour in a cell incubator. After that, the plate was transferred into high content imaging system Operetta (PerkinElmer) equipped with environmental control unit, which allowed to keep 37° C., 5% $CO_2$. For two movies that were made, the brightfield images were taken once in 15 minutes during 24 hours after plating using Harmony software (PerkinElmer), exported, and analyzed using ImageJ software (NIH, the US). For migration assay the images were taken every seven minutes during 18 hours after plating. Images acquired between the fifth and seventh hours after plating were analyzed using MTrackJ plug-in (University Medical Center, Rotterdam, The Netherlands). 100 attached cells on each coating were traced and mean distances from the current to the previous point of the track were calculated. Error bars show standard error of the mean s.e.m. (n=100).

Statistics. Statistical significance was determined the by Student's two-tailed t-test for unequal variances.

Discussion of Results for Example 2

Pluripotent hES cells express α1, α5, β1, β2 and γ1 laminin chains. To compare the adhesion and clonal survival of hES cells plated from single cell suspension to different coating substrata, hES cells growing as monolayers on LN-511 or as clusters on a feeder layer were trypsinized into single cell suspension in O3 medium and plated on cell culture dishes coated with Matrigel, LN-111, LN-511, LN-521 or a mixture of LN-511 and LN-521, in the absence or presence of a ROCK inhibitor (Y-27632) and analyzed after 24 hours.

The cells did not survive on Matrigel or LN-111, but they did so as single cells on human recombinant LN-511 and LN-521, as well as on the mixture of the two. However, the survival of cells on LN-521 was significantly higher than on LN-511 (compared in numbers below). Cells plated on human recombinant LN-111 or LN-121 failed to survive after 24 hours (data not shown), which demonstrates that the presence of the β2 chain in a laminin trimer, as such, is not sufficient to support the effect. In the presence of ROCK inhibitor Y-27632, the hES cells survived on all surfaces.

There were, however, clear differences with regard to cell shapes between cells growing on LN-521 in the absence or presence of ROCK inhibitor 24 hours after plating. In the absence of ROCK inhibitor 24 hours after plating, cells growing on LN-521 were round, while the cells growing in the presence of ROCK inhibitor adopted spindle or crescent like shape possibly caused by rearrangement of the actin cytoskeleton.

To test if LN-521 could be used as a cell coating material for long-term self-renewal of human pluripotent cells, HS181, HS401, H1 cells and human PS ChiPSW and CutB1.2 cells were cultured on the protein in O3, mTeSR1 or TeSR2 media. Cells growing in O3 or TeSR1 media were passed in single cells suspension every 10-14 days at ratios of 1:20-1:30. Pluripotent hES cells proliferated at a stable rate similar or higher to that of cells grown on LN-511 or Matrigel when passed in small clumps. Thus, one passage on LN-521 yielded the same or higher number of cell divisions than that of control cells passed twice in clumps. HS181, HS401, and H1 cells proliferated for at least 24, 5 and 15 passages, respectively (9, 2 and 6 months) in an O3 medium. CutB1.2 iPS and ChiPSW cells have been cultured for 5 and 3 passages in mTeSR1, respectively. Interestingly, dissociated hES cells could be cultured on LN-521 under completely defined and xeno-free conditions, using TeSR2 medium and TrypLE Select enzyme. The plating efficacy after a passage was slightly lower than that of the cells in O3 or mTeSR1 media, and the dissociated cells were passed normally every 10-14 days in 1:15-1:20 ratios. H1 and HS401 cells have been cultured for 12 and 4 passages, respectively (5 and 1.5 months) in TeSR2.

The hES cells were usually plated in single cell suspension at 30,000 cells per 1 $cm^2$ of culture dish coated with LN-521, after which individual cells lacked any direct contacts with each other. Eight hours after plating, the hES cells could be observed as single cells expressing pluripotency markers Oct4, Nanog, and Sox2. Twenty four hours after plating, the cells formed small monolayer colonies that eventually combined into large islands of monolayers covering most of the well.

Cells grown on LN-521 showed stable expression levels of pluripotency markers Oct4, Nanog, and SSEA4, which were similar to those in cells plated on Matrigel and passed as small clumps. To compare the level of spontaneous differentiation in LN-521 and Matrigel cultures, the amount of mRNAs for differentiation markers PAX6, SOX17 and SOX7 expressed in Matrigel cultures and in LN-521 cultures were compared after one (10 days) and 10 passages (4 months). Quantitative RT-PCR revealed similar or less levels of expression of all three markers of differentiation in LN-521 cultures independently on the passage number.

Karyotypes were confirmed to be normal for hES cell lines HS181 and H1 after 12 and 10 passages, respectively, on LN-521 in the O3 medium; and for H1 after 7 passages in TeSR2 medium. Histological examination of teratomas formed in SCID mice after injection of HS181 and H1 cells cultured for 13 and 12 passages, respectively, on LN-521 in O3 medium, and H1 cells cultured for 7 passages on LN-521 in TeSR2 revealed development of tissues containing all three germ lineages of the human embryo. Differentiation in vitro also revealed, that the cells in all three cases retained the competence to form embryoid bodies expressing markers of mesoderm (smooth-muscle actin), ectoderm (MAP-2) and endoderm (α-fetoprotein).

To quantify the efficacy of the coating substrata, adhesion after one hour and survival after 24 hours of dissociated hES cells on Matrigel, LN-111, LN-511, LN-521, and an equal mixture of LN-511 and LN-521 were studied. Interestingly, after one hour about the same 75-80% of cells had adhered to all the coatings, although the spreading of the cells was clearly better on LN-521 and LN-511 than on Matrigel or LN-111 (not shown). After 24 hours, almost no cells had survived on Matrigel or LN-111, and very few on LN-511. In contrast, the survival of hES cells on LN-521 was approximately 20 times higher than on Matrigel, and three times higher than on LN-511.

To qualitatively compare the effects of LN-521 and ROCK inhibitor (Y-27632), we plated cells from the same single cell suspension at the same plating density (40,000 cells per 1 $cm^2$) in a medium containing 10 µM of Y-27632 and studied their survival on the different coatings. The untreated cells on LN-521 and Y-27632 treated cells on Matrigel showed similar survival rate 24 hours after plating. Interestingly, even Y-27632 treated human ES cells survived better on LN-521 than on Matrigel.

If exogenous bFGF was removed from the O3 medium, the cells still showed 20 times higher survival on LN-521 than on Matrigel. Moreover, hES cells survived on LN-521 24 hours after plating, even in a medium lacking all the growth factors of the TeSR1 formulation (bFGF, LiCl, γ-aminobutyric acid (GABA), pipecolic acid and TGFβ)[16], suggesting that the survival mechanism is independent of signaling induced by those factors.

An assay for inhibition of cell survival using function-blocking antibodies to potential receptors for LN-521 on the plasma membrane showed that antibodies to integrins α6, and to a slightly lesser extent to β1, inhibited survival of human ES cells on LN-521. Function-blocking antibodies to other tested integrin subunits, as well as to Lutheran receptor and α-dystroglycan, showed very little if any effects on human ES cell survival on LN-521.

Figure 12:
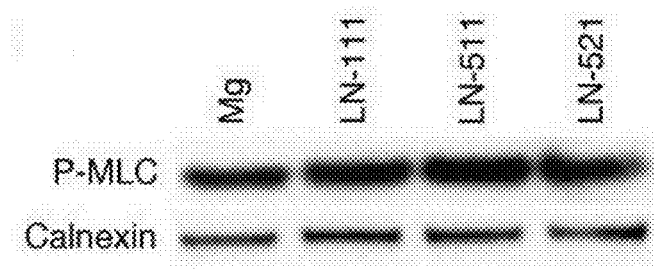
FIG. 12 is a Western blot comparing the levels of phosphorylated myosin light chain (P-MLC) in stem cells grown on Matrigel (Mg), LN-111, LN-511, and LN-521 one hour after plating.
Figure 13:
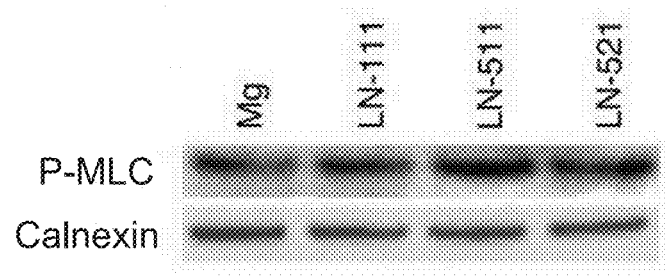
FIG. 13 is a Western blot comparing the levels of phosphorylated myosin light chain (P-MLC) in stem cells grown on Matrigel (Mg), LN-111, LN-511, and LN-521 six hours after plating.
Figure 14:
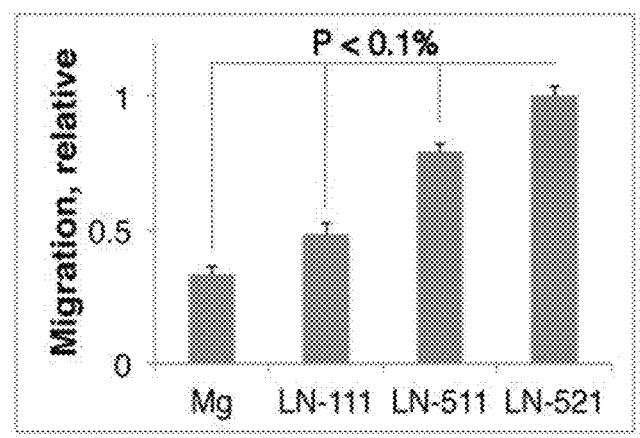
FIG. 14 is a graph comparing the relative migration of human embryonic stem cells grown on Matrigel (Mg), LN-111, LN-511, and LN-521 between five and seven hours after plating.
Figure 15:
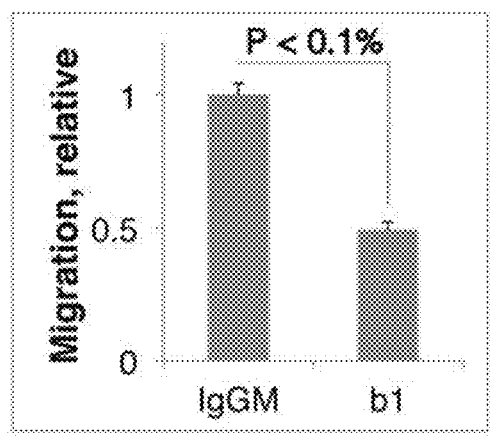
FIG. 15 is a graph comparing the relative migration of human embryonic stem cells grown on LN-521 with IgG and IgM blocking antibodies applied (IgGM) and with a function blocking antibody to integrin p1 (b1) applied. This shows that blocking the integrin significantly reduced motility.

Recently, it has been shown that ROCK inhibitors and blebbistatin act through abrogation of actin-myosin contractility, which is mediated by phosphorylation of the myosin light chain (MLC). To test if LN-521 had similar activity, levels of phosphorylated MLC were compared between the dissociated cells on Matrigel, LN-111, LN-511, and LN-521 one and six hours after plating (FIG. 12 and FIG. 13). Interestingly, western blot showed that phosphorylation of MLC was even higher in the cells on LN-511 and LN-521 than that in the cells on Matrigel and LN-111. Since actin-myosin rearrangements are essential not only for contractions, but also for cell motility, we surmised that the cell migration could be caused by interaction between LN-521 and its integrin receptor α6 µl. In vivo imaging of the cells on Matrigel and LN-521 revealed that the cells migrated much faster on the latter and survived by aggregation into small fast moving colonies. Migration of hES cells on the four coatings was also compared between the fifth and seventh hours after plating when the cells were still attached in all cases (FIG. 14). Motility of the hES cells on LN-521 was higher than that of the cells on other coatings and correlated with the ability to survive on them. Treatment with function blocking antibody to integrin β1 significantly reduced motility (FIG. 15) and adhesion (data not shown) of the cells on LN-521.

Figure 16:
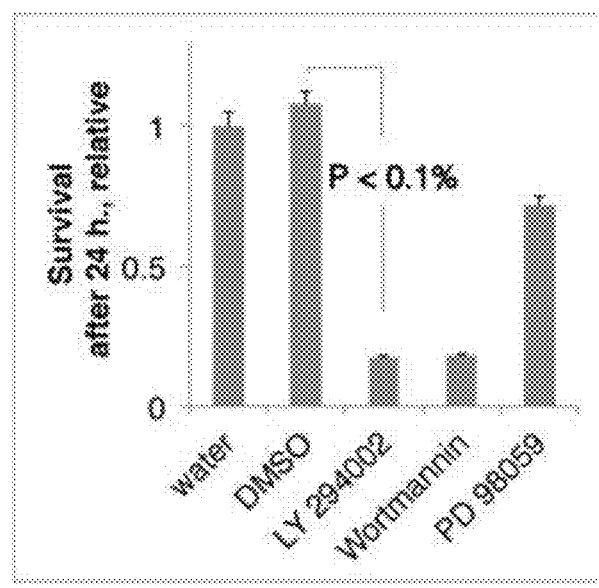
FIG. 16 is a graph comparing the relative survival of hES cells on LN-521 in the presence of water, DMSO, LY294002 (Akt inhibitor), wortmannin (PI3K/Akt inhibitor), and PD 98059 (MEK1 inhibitor). This showed that activation of PI3K/Akt was necessary for hES cell survival on LN-521. The medium contained bFGF.

An extensive body of data has shown that activation of the MEK1/Erk or PI3-kinase/Akt pathways by integrins can block anoikis. The effects of LY 294002 and PD 98059, specific inhibitors of Akt and MEK1, respectively, were examined to explore the potential role of these pathways in hES cell survival on LN-521. Blockade of Akt activation by LY 294002 was found to facilitate detachment and hES cell death, with no cells surviving 24 hours after plating on LN-521 (FIG. 16). In contrast, treatment with PD 98059 did not affect the survival that severely. hES cells treated with another PI3K/Akt specific inhibitor, Wortmannin, also failed to survive 24 hours after plating on LN-521, confirming that activation of PI3K/Akt was necessary for the cell survival on LN-521.

Figure 17:
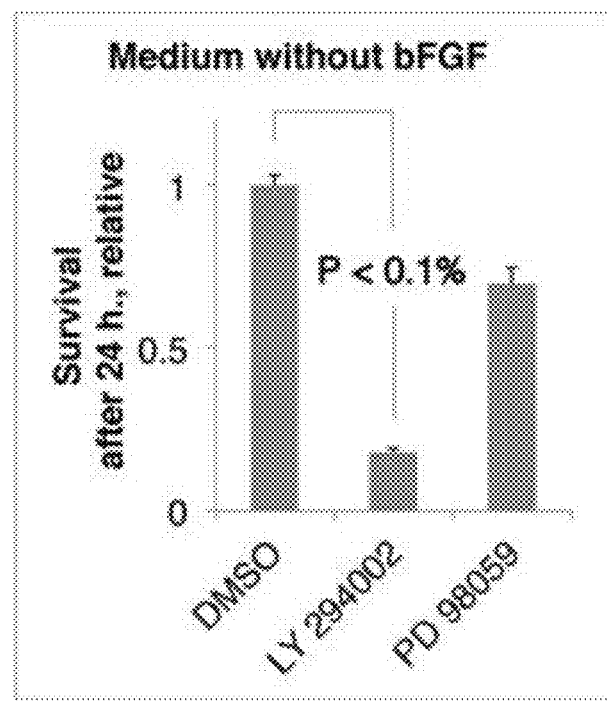
FIG. 17 is a graph comparing the relative survival of hES cells on LN-521 in the presence of DMSO, LY294002 (Akt inhibitor), and PD 98059 (MEK1 inhibitor). No exogenous bFGF was present.
Figure 18:
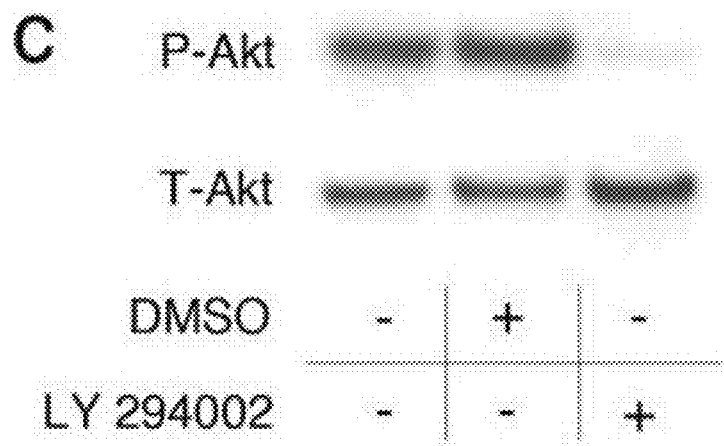
FIG. 18 is a Western blot comparing cells treated with LY 294002 against control cells (DMSO) and collected one hour after plating on LN-521.
Figure 19:
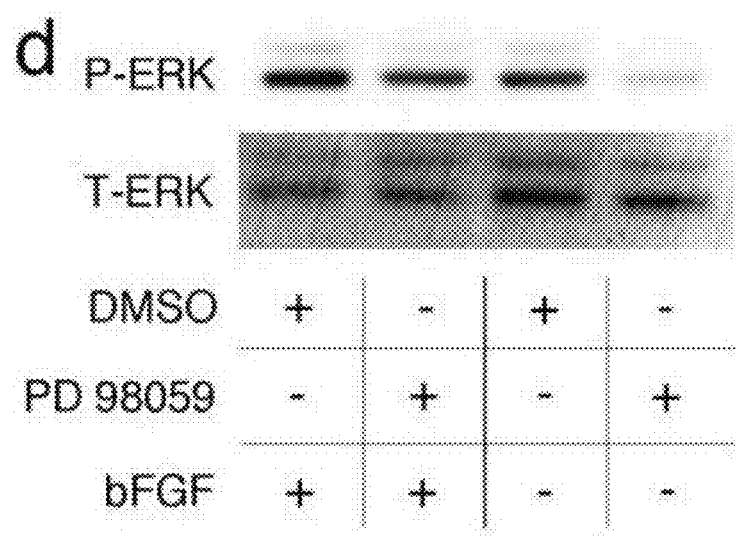
FIG. 19 is a Western blot comparing cells treated with PD98059 against control cells (DMSO) and collected one hour after plating on LN-521.

Since bFGF is known to be a potent activator of the MEK1/Erk pathway, the influence of which cannot be fully inhibited by PD 98059, we performed the same experiment in O3 medium without exogenous bFGF with the same result (FIG. 17). The efficacy of LY 294002 and PD 98059 treatment was confirmed by western blot analysis of the treated and control cells collected one hour after plating on LN-521 (FIG. 18 and FIG. 19).

Figure 20:
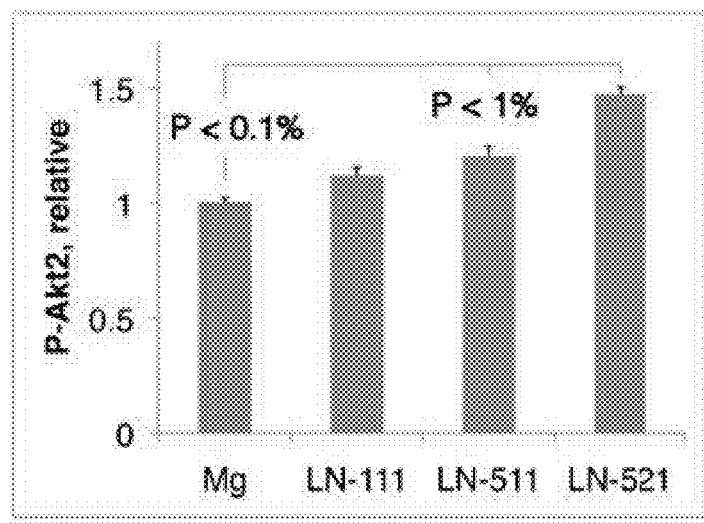
FIG. 20 is a graph showing the relative levels of Akt2 phosphorylation on cell lysates collected one hour after plating on Matrigel (Mg), LN-111, LN-511, or LN-521, obtained using ELISA.
Figure 21:
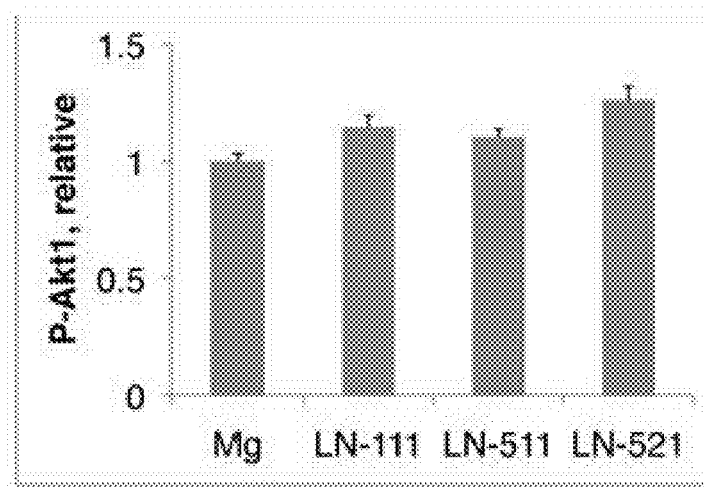
FIG. 21 is a graph showing the relative levels of Akt1 phosphorylation on cell lysates collected one hour after plating on Matrigel (Mg), LN-111, LN-511, or LN-521, obtained using ELISA.

Western blot analysis of extracts of cells growing on Matrigel and LN-521 with antibodies to phospho-Akt showed that the PI3K/Akt pathway was active in both cases (data not shown). To determine the levels of Akt activation in the cells on different coating, ELISA was performed on cell lysates collected one hour after plating on Matrigel, LN-111, LN-511 and LN-521 when the cells still did not have direct contacts with each other (FIG. 20 and FIG. 21). The level of Akt2 phosphorylation in the cells on different coatings correlated with survivability on them.

It has been demonstrated that α6 and β1 integrins are the most abundantly expressed integrin isoforms in human ES cells among alpha and beta subunits respectively. Integrin α6β1 shows a broad spectrum of specificity towards different laminins, but the binding affinity for LN-521 or LN-511 is higher than that for LN-111. Recently, it has been established that β2 laminins have higher affinity for integrins than the β1 laminins. Therefore, having the highest affinity for the integrin, LN-521 can provide the best anchorage for migration and can convey the highest dose of signal via α6β1 integrin resulting in the best survivability of dissociated pluripotent hES cells, although e.g. LN-511 also can do it at a lesser extent.

The results of this work may facilitate culturing and expansion of pluripotent human stem cells in general, and even make automated expansion of such cells possible including cell aimed for clinical applications. The survival of dissociated hES cells on LN-521 appears to be dependent on migration and the cells can therefore not survive after plating at ultralow densities. The new hES cell culture method described here utilizes only a naturally occurring LN-521 adhesion protein that does not damage the cytoskeleton as ROCK inhibitor or blebbistatin treatment do. Thus, LN-521 most probably favors survival of the cells only with the correct integrin profile on the cell surface. The present results also showed that hES cells plated on LN-521 at relatively low densities of 20,000-30,000 cells per 1 $cm^2$ could survive and multiply at least as efficiently as in the other hES culture systems. The new method closely resembles standard cell culture procedures, e.g. culturing of fibroblasts, and, therefore, hES cell cultures on LN-521 do not demand specially trained personnel, which has been a major problem before since culturing of hES cells has been a technological challenge.

The widely used TeSR1 formulation for human pluripotent stem cell self-renewal was initially developed for use with Matrigel and it contains high doses of bFGF that mostly targets the MEK1/Erk pathway, which is not widely considered to have a beneficial effect for pluripotent hES cells. The present results can lead to development of new medium formulations utilizing benefits of LN-521 as coating material and specifically targeting pathways, which are important for human ES cell self-renewal.

In summary, the present work has demonstrated that LN-521, normally secreted by pluripotent hES, can as a sole coating material support self-renewal of human pluripotent stem cells in culture, similar to LN-511. Both laminins facilitated growth of the cells as homogenous monolayers in vitro. However, an important difference between the two laminins is that hES/hiPS cells could be trypsinized into single cell suspension, and plated and effectively expanded from single cells on LN-521, as opposed to manual splitting of cell clusters, as is currently required for expansion of hES/iPS cells grown on Matrigel or feeder cells. The results of this work may facilitate culturing of pluripotent human stem cells and facilitate automated expansion of such cells.

Example 3

Human embryonic stem cells were cultured upon a laminin-521 substrate in two different cell culture mediums. The two cell culture mediums differed in the amount of bFGF, 3.9 ng/ml and 100 ng/ml.

Figure 22:
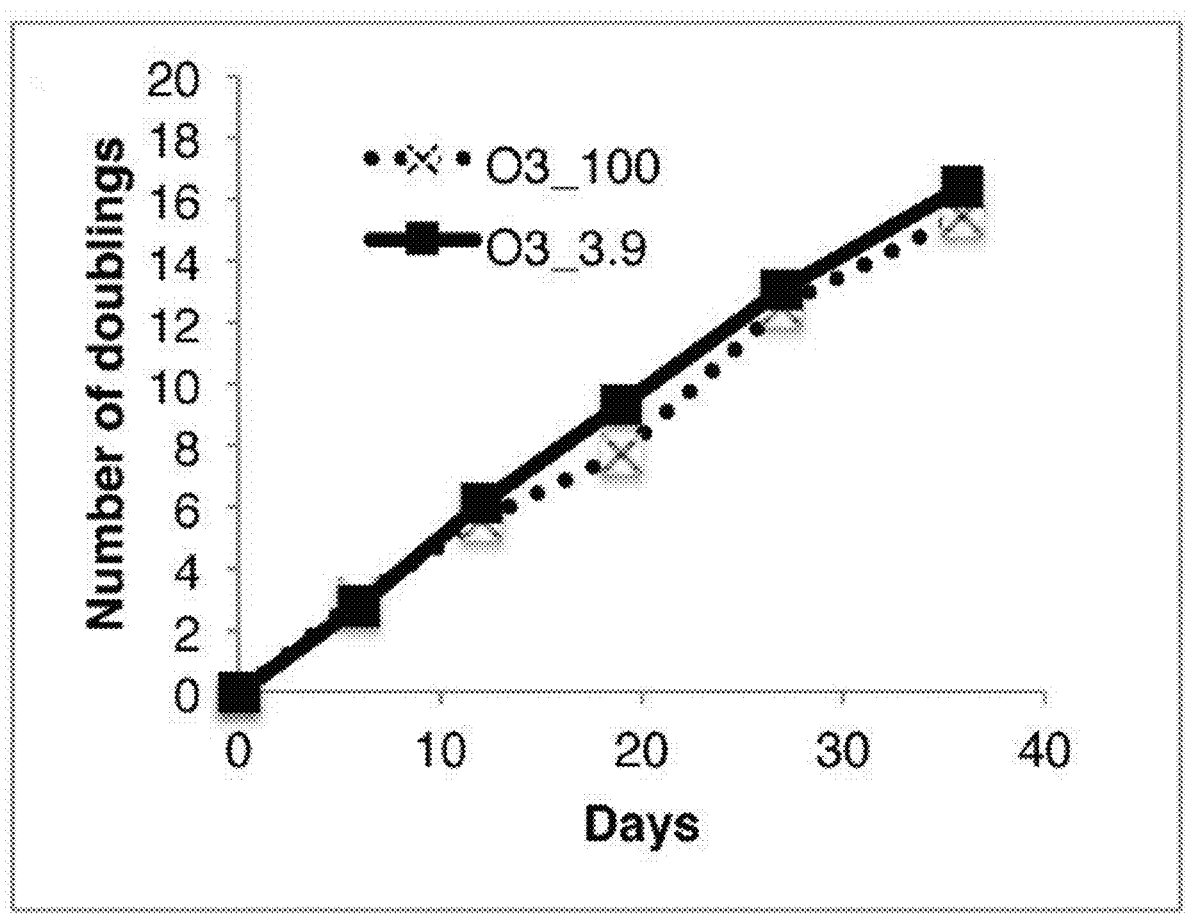
FIG. 22 is a graph showing the growth curve of HS181 hES cells cultured in a low bFGF medium (O3_3.9) compared to a higher bFGF medium (O3_100).

FIG. 22 shows the growth curve of HS181 hES cells cultured in an O3 medium comprising 3.9 ng/mL of bFGF with a laminin-521 substrate after 5 passages (40 days) in solid black. The O3 medium was a variant of the commercially available chemically defined mTeSR1 medium with bovine serum albumin as the only animal derived component. The growth curve of HS181 hES cells cultured in an O3 medium comprising 100 ng/mL of bFGF with a laminin-521 substrate is shown in dashes. The cells were dissociated into single cell suspension for passaging. As seen here, the growth curve for the lower amount of bFGF was as good as or better than the higher amount of bFGF.

Figure 23:
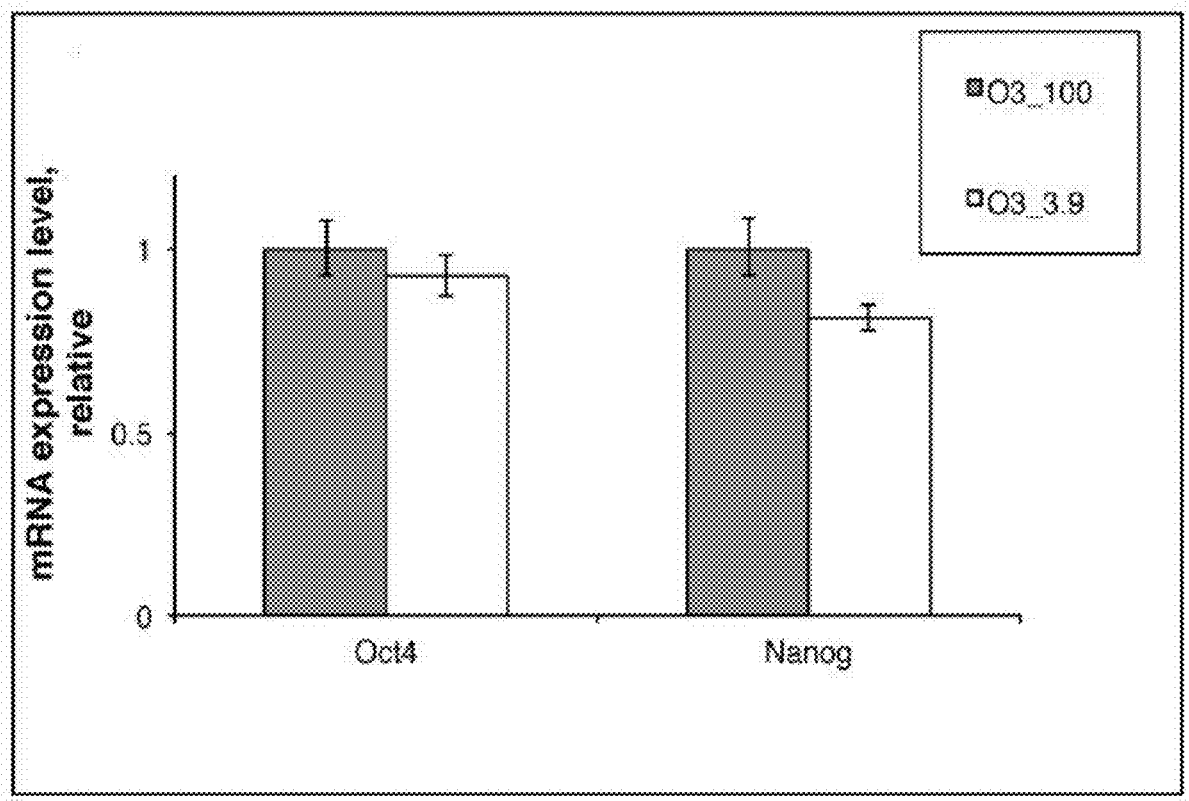
FIG. 23 is a graph showing the relative mRNA expression level for two pluripotency markers (Oct4 and Nanog) in HS181 hES cells cultured in a low bFGF medium (O3_3.9) compared to a higher bFGF medium (O3_100).

FIG. 23 shows the relative amount of mRNA transcripts for pluripotency markers Oct4 and Nanog after 5 passages (40 days) for both media, which was obtained using real-time quantitative reverse transcription polymerase chain reaction (RT-PCR) analysis. Again, similar amounts were obtained in both cell culture mediums, indicating that the stem cells in the lower amount of bFGF maintained pluripotency. Thus, a lower amount of bFGF can be used and still obtain good results, particularly in combination with the laminin-521 substrate.

Example 4

In Examples 1 and 2, the dissociated stem cells survived mostly through active motility on LN-521 and association into small effectively growing and migrating monolayer islands. The cells plated at very low, cloning densities died through anoikis, a specialized from of programmed cell death. Normally, integrin-related signaling from extracellular matrix molecules, e.g. laminins, and cadherin-related cell-cell signaling, can prevent anoikis. The most abundant cadherin isoform on the human ES cell surface is epithelial-cadherin (E-Cadherin). The experiments in Examples 3 were performed to find out if a combination of LN-521 and E-Cadherin could protect human ES cells from anoikis and allow clonal survival of the cells.

hES cells were plated in mTeSR1 medium on different coatings at a density of 250 cells per $cm^2$ and monitored after 5 days in culture using an alkaline phosphatase staining kit. Neither laminin-521 nor E-Cadherin alone permitted efficient clonal survival of individualized hES cells.

Next, combinations of laminin-521 and E-Cadherin were tested to determine whether the combinations could sustain clonal survival of the cells. Fixed amounts of laminin-521 were used for the cell culture dish coating in combination with titrated E-Cadherin. Clonal survival of cells was achieved at different ratios of E-Cadherin to laminin-521 including from about 1:10 w/w to about 1:5 w/w.

Additional tests were performed to test the effects of various modifications to the mTeSR1 medium. A mixture of E-Cadherin to laminin-521 in a ratio of about 1:10 w/w was used to coat the plates. Unexpectedly, it was discovered that a 2× increase in albumin concentration significantly improved clonal survival of hES cells on the laminin-521/E-Cadherin matrix. The rate of individualized hES cell survival under these conditions was from 10 to 15% and was at least one order of magnitude higher than that of the cells on Matrigel, laminin-521, or E-Cadherin alone in both mTeSR1 medium and mTeSR1 medium with additional albumin. Time-lapse photography of the cells confirmed that laminin-521/E-Cadherin coatings facilitated cell survival through proliferation of the single cells, not through the aggregation of different cells. Laminin-521/E-Cadherin similarly sustained clonal survival of cells in completely chemically defined and xeno-free TeSR2 medium with the addition of recombinant human serum albumin (rHSA).

In additional testing, hES cell lines were derived. Twenty-four well tissue cell culture dish plates were washed twice with Dulbecco's Phosphate Buffered Saline. Next, the dish plates were coated for 2 hours at 37° C. with sterile solution containing: 48 µL of 100 µg/mL laminin-521 (BioLamina AB, Stockholm); 6 µL of 82 µg/mL E-Cadherin (R@DSystems); and 300 µL of DPBS with calcium and magnesium (GIBCO) to produce a laminin-521/E-Cadherin matrix.

The donated embryos used to derive the hES cell lines were obtained from an accredited in vitro fertilization clinic after the consent of both partners and ethics approval were obtained. Only fresh or frozen embryos, which could not be used for infertility treatment, were used in the derivation procedures. One or two cells were isolated from an 8-cell stage embryo using a micropipette after making a small opening to the zona pellucida with a laser apparatus designed for this purpose. The cells were placed on the laminin-521/E-Cadherin matrix in TeSR2 medium with additional rHSA. The cells successfully attached and started to proliferate. The parental embryos were allowed to grow to a blastocyst stage and frozen. The embryo culture was carried out using xeno-free standardized in vitro fertilization culture media in drops under oil at 37° C. and 5% $O_2$/10% $CO_2$. After removal of the zona pellucida, the inner cell masses of five human blastocysts were mechanically isolated and plated in 4-well culture plates (Nunc) onto the laminin-521/E-Cadherin matrix. Following an initial 48 hours of culture, the culture medium was replaced on a daily basis. After 10 to 14 days, the outgrowths were mechanically isolated and replated onto laminin-521/E-Cadherin matrix. Mechanical passaging was used for the subsequent 2 to 3 passages after which colonies were passaged using TrypLE Select (GIBCO).

Figure 24:
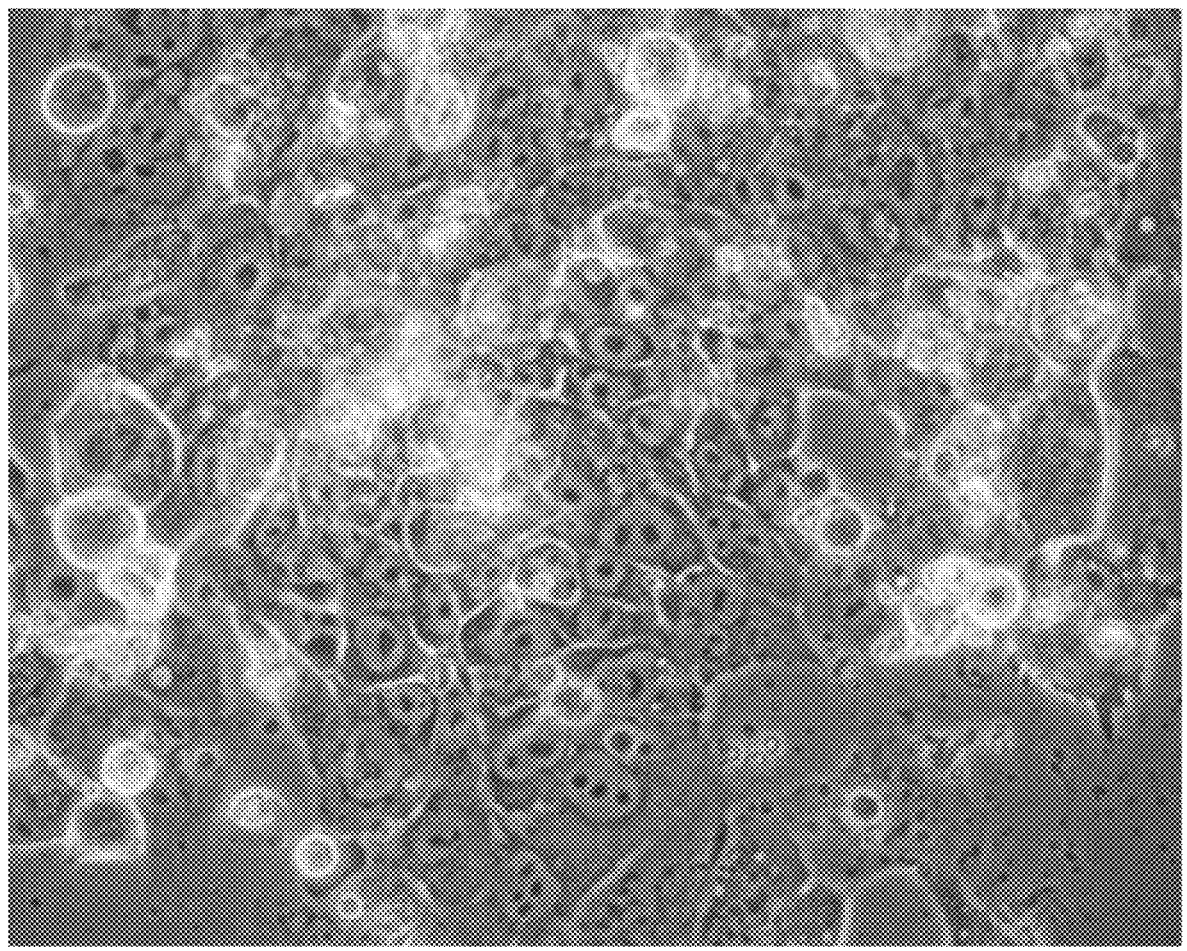
FIG. 24 is a picture showing an early stage derivation of a new human embryonic stem HS841 cell line on laminin-521/E-Cadherin matrix.

Using the laminin-521/E-Cadherin matrix described above with the mTeSR1 medium including additional bovine albumin, three new hES cell lines were derived from six cultured blastocysts. Four days after plating, the inner cell masses gave stem cell-like outgrowths. FIG. 24 shows an early stage derivation of a new human embryonic stem HS841 cell line on laminin-521/E-Cadherin matrix. Morphologically typical human embryonic stem cells growing out from the inner cell mass of a day six blastocyst four days after mechanical isolation of the inner cell mass and plating on laminin-521/E-Cadherin matrix are shown.

Unexpectedly, the cell culture system and method gave stable, hES cell lines in 3 out of 6 embryos (50%), a derivation rate higher than that of standard methods.

The use of a laminin-521/E-Cadherin matrix and TeSR2 medium with additional rHSA, a completely chemically defined and xeno-free environment, yielded similar results in the derivation of new hES cell lines.

Table 5 below provides the formulation for the mTeSR1 medium used in this Example. The amounts of each ingredient can vary by up to 20%.

In particular embodiments, the amount of human serum albumin (HSA) can be varied from a concentration of 0.195 mM to 1 mM including from 0.3 mM to 1 mM or from 0.3 mM to about 0.4 mM. The amount of bFGF can also be varied from 0 to about 105 ng/mL, or from 0 to 3.9 ng/mL, or from 0.5 ng/mL to 3.5 ng/mL. These two variations in the amount of HSA and bFGF may occur independently or together.

TABLE 5 mTeSR1 formulation.

| mTeSR1 Ingredient | molar mass (g/mol) | Concentration (ng/mL) | Concentration (mM) |
|---|---|---|---|
| INORGANIC SALTS | | | |
| Calcium chloride (Anhydrous) | 110.98 | 9.14E+04 | 8.24E−01 |
| HEPES | 238.3 | 2.81E+06 | 1.18E+01 |
| Lithium Chloride (LiCl) | 42.39 | 4.15E+04 | 9.80E−01 |
| Magnesium chloride (Anhydrous) | 95.21 | 2.26E+04 | 2.37E−01 |
| Magnesium Sulfate ($MgSO_4$) | 120.37 | 3.84E+04 | 3.19E−01 |
| Potassium chloride (KCl) | 74.55 | 2.43E+05 | 3.26E+00 |
| Sodium bicarbonate ($NaHCO_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E−01 |
| Sodium phosphate, monobasic monohydrate ($NaH_2PO_4$—$H_2O$) | 137.99 | 4.90E+04 | 3.55E−01 |
| TRACE MINERALS | | | |
| Ferric Nitrate ($Fe(NO_3)_3$—$9H_2O$) | 404 | 3.92E+01 | 9.71E−05 |
| Ferrous sulfate heptahydrate ($FeSO_4$—$7H_2O$) | 278.01 | 3.28E+02 | 1.18E−03 |
| Copper(II) sulfate pentahydrate ($CuSO_4$—$5H_2O$) | 249.69 | 1.02E+00 | 4.08E−06 |
| Zinc sulfate heptahydrate ($ZnSO_4$—$7H_2O$) | 287.56 | 3.39E+02 | 1.18E−03 |
| Ammonium Metavanadate $NH_4VO_3$ | 116.98 | 1.28E+00 | 1.09E−05 |
| Manganese Sulfate monohydrate ($MnSO_4$—$H_2O$) | 169.02 | 3.33E−01 | 1.97E−06 |
| $NiSO_4$—$6H_2O$ | 262.85 | 2.55E−01 | 9.70E−07 |
| Selenium | 78.96 | 1.40E+01 | 1.77E−04 |
| Sodium Meta Silicate $Na_2SiO_3$ $9H_2O$ | 284.2 | 2.75E+02 | 9.66E−04 |
| $SnCl_2$ | 189.62 | 2.35E−01 | 1.24E−06 |
| Molybdic Acid, Ammonium salt | 1235.86 | 2.43E+00 | 1.97E−06 |
| $CdCl_2$ | 183.32 | 2.24E+00 | 1.22E−05 |
| $CrCl_3$ | 158.36 | 3.14E−01 | 1.98E−06 |
| $AgNO_3$ | 169.87 | 1.67E−01 | 9.81E−07 |
| $AlCl_3$ $6H_2O$ | 241.43 | 1.18E+00 | 4.87E−06 |
| Barium Acetate ($Ba(C_2H_3O_2)_2$) | 255.42 | 2.50E+00 | 9.79E−06 |
| $CoCl_2$ $6H_2O$ | 237.93 | 2.33E+00 | 9.81E−06 |
| $GeO_2$ | 104.64 | 5.20E−01 | 4.97E−06 |
| KBr | 119 | 1.18E−01 | 9.89E−07 |
| KI | 166 | 1.66E−01 | 1.00E−06 |
| NaF | 41.99 | 4.13E+00 | 9.83E−05 |
| RbCl | 120.92 | 1.19E+00 | 9.81E−06 |
| $ZrOCl_2$ $8H_2O$ | 178.13 | 1.75E+00 | 9.80E−06 |
| ENERGY SUBSTRATES | | | |
| D-Glucose | 180.16 | 2.47E+06 | 1.37E+01 |
| Sodium Pyruvate | 110.04 | 4.31E+04 | 3.92E−01 |
| LIPIDS | | | |
| Linoleic Acid | 280.45 | 5.27E+01 | 1.88E−04 |
| Lipoic Acid | 206.33 | 8.25E+01 | 4.00E−04 |
| Arachidonic Acid | 304.47 | 3.93E+00 | 1.29E−05 |
| Cholesterol | 386.65 | 4.33E+02 | 1.12E−03 |
| DL-alpha tocopherol-acetate | 472.74 | 1.37E+02 | 2.90E−04 |
| Linolenic Acid | 278.43 | 1.95E+01 | 6.99E−05 |
| Myristic Acid | 228.37 | 1.96E+01 | 8.59E−05 |
| Oleic Acid | 282.46 | 1.96E+01 | 6.94E−05 |
| Palmitic Acid | 256.42 | 1.96E+01 | 7.65E−05 |
| Palmitoleic acid | 254.408 | 1.96E+01 | 7.71E−05 |
| Stearic Acid | 284.48 | 1.96E+01 | 6.89E−05 |
| AMINO ACIDS | | | |
| L-Alanine | 89.09 | 1.22E+04 | 1.37E−01 |
| L-Arginine hydrochloride | 147.2 | 8.07E+04 | 5.48E−01 |
| L-Asparagine-$H_2O$ | 150.13 | 2.06E+04 | 1.37E−01 |
| L-Aspartic acid | 133.1 | 1.82E+04 | 1.37E−01 |
| L-Cysteine-HCl—$H_2O$ | 175.63 | 1.38E+04 | 7.83E−02 |
| L-Cystine dihydrochloride | 313.22 | 2.45E+04 | 7.83E−02 |
| L-Glutamic acid | 147.13 | 2.02E+04 | 1.37E−01 |

TABLE 5-continued mTeSR1 formulation.

| mTeSR1 Ingredient | molar mass (g/mol) | Concentration (ng/mL) | Concentration (mM) |
|---|---|---|---|
| L-Glutamine | 146.15 | 4.30E+05 | 2.94E+00 |
| Glycine | 75.07 | 2.21E+04 | 2.94E−01 |
| L-Histidine monohydrochloride monohydrate | 209.63 | 2.47E+04 | 1.18E−01 |
| L-Isoleucine | 131.17 | 4.28E+04 | 3.26E−01 |
| L-Leucine | 131.17 | 4.64E+04 | 3.54E−01 |
| L-Lysine hydrochloride | 182.65 | 7.14E+04 | 3.91E−01 |
| L-Methionine | 149.21 | 1.35E+04 | 9.06E−02 |
| L-Phenylalanine | 165.19 | 2.79E+04 | 1.69E−01 |
| L-Proline | 115.13 | 2.49E+04 | 2.16E−01 |
| L-Serine | 105.09 | 3.09E+04 | 2.94E−01 |
| L-Threonine | 119.12 | 4.19E+04 | 3.52E−01 |
| L-Tryptophan | 204.23 | 7.07E+03 | 3.46E−02 |
| L-Tyrosine disodium salt hydrate | 225.15 | 3.78E+04 | 1.68E−01 |
| L-Valine | 117.15 | 4.16E+04 | 3.55E−01 |
| VITAMINS | | | |
| Ascorbic acid | 176.12 | 4.46E+04 | 2.53E−01 |
| Biotin | 244.31 | 2.74E+00 | 1.12E−05 |
| B12 | 1355.37 | 5.34E+02 | 3.94E−04 |
| Choline chloride | 139.62 | 7.02E+03 | 5.03E−02 |
| D-Calcium pantothenate | 238.27 | 8.79E+02 | 3.69E−03 |
| Folic acid | 441.4 | 2.08E+03 | 4.71E−03 |
| i-Inositol | 180.16 | 9.89E+03 | 5.49E−02 |
| Niacinamide | 122.12 | 1.59E+03 | 1.30E−02 |
| Pyridoxine hydrochloride | 205.64 | 1.57E+03 | 7.62E−03 |
| Riboflavin | 376.36 | 1.72E+02 | 4.56E−04 |
| Thiamine hydrochloride | 337.27 | 8.16E+03 | 2.42E−02 |
| GROWTH FACTORS/PROTEINS | | | |
| GABA | 103.12 | 1.01E+05 | 9.79E−01 |
| Pipecolic Acid | 129 | 1.27E+02 | 9.84E−04 |
| bFGF | 18000 | 1.04E+02 | 5.77E−06 |
| TGF beta 1 | 25000 | 5.88E−01 | 2.35E−08 |
| Human Insulin | 5808 | 2.28E+04 | 3.92E−03 |
| Human Holo-Transferrin | 78500 | 1.08E+04 | 1.37E−04 |
| Human Serum Albumin | 67000 | 1.31E+07 | 1.95E−01 |
| Glutathione (reduced) | 307.32 | 1.96E+03 | 6.38E−03 |
| OTHER COMPONENTS | | | |
| Hypoxanthine Na | 136.11 | 1.61E+03 | 1.18E−02 |
| Phenol red | 354.38 | 5.99E+03 | 1.69E−02 |
| Putrescine-2HCl | 161.07 | 6.36E+01 | 3.95E−04 |
| Thymidine | 242.229 | 2.86E+02 | 1.18E−03 |
| 2-mercaptoethanol | 78.13 | 7.66E+03 | 9.80E−02 |
| Pluronic F-68 | 8400 | 1.96E+05 | 2.33E−02 |
| Tween 80 | 1310 | 4.31E+02 | 3.29E−04 |

The systems containing a LN-521/e-cadherin substrate and mTeSR1 medium with additional albumin work extremely well for maintaining and proliferating undifferentiated stem cells (e.g. embryonic and induced pluripotent stem cells) in a completely chemically defined environment and xeno-free conditions without feeders or any inhibitors of apoptosis.

In this context, LN-521 and LN-511 can be used in a substrate combined with e-cadherin. The LN-521/LN-511 may be present as an intact protein or as a protein fragment. Again, a "fragment" contains one, two, or three functional domains that possesses binding activity to another molecule or receptor. Generally, any effective laminin may be used, wherein the effectiveness is determined by whether stem cells can proliferate upon the substrate. The laminins are usually recombinant as well.

Additionally, systems containing a laminin substrate and cell culture medium can be used to make new retinal pigment epithelium (RPE) cells. In this regard, impairment of vision is a major reason for severe morbidity. Age-related macular degeneration (AMD) is a medical condition which results in a loss of vision in the center of the visual field (the macula) because of damage to the retina. Age-related macular degeneration begins with characteristic yellow deposits (drusen) in the macula, between the retinal pigment epithelium and the underlying choroid. In the "dry" form of advanced AMD the retinal pigment epithelial layer below the retina atrophies, which causes vision loss through loss of photoreceptors (rods and cones) in the central part of the eye.

AMD is the most common cause of severe vision loss in the Western world with an economic burden on the health care system exceeding that of stroke. In Europe and North America alone, more than 5 million people suffer from end-stage AMD (i.e. neovascular or geographic atrophy) with an incidence of almost 500,000 individuals per year. The prevalence is further expected to increase by 75% in 2040. Moreover, impaired vision is associated with several significant co-morbidites such as fragility fractures in the aging population, causing an enormous burden on health and society resources.

The RPE is the pigmented cell layer just outside the neurosensory retina that nourishes retinal visual cells, and is firmly attached to the underlying choroid and overlying retinal visual cells. This single RPE cell layer is essential for normal neuroretinal and choroidal function. For example, the RPE phagocytoses (digests) the photoreceptor outer segments, thus maintaining normal cell turnover. The RPE also synthesize the structural proteins of Bruch's membrane that in turn constitutes the outer blood-retinal barrier. In early AMD, an accumulation of undigested intracellular debris occurs in the RPE and the sub-RPE space that progressively decreases RPE function. In advanced AMD, the RPE dysfunction will lead to an ingrowth of choroidal vessels through breaks in Bruch's membrane (ie. neovascular AMD) and/or geographic atrophy.

In geographic atrophy (GA), the degeneration primarily affects the RPE and photoreceptors and restoration by cell transplantation seems logical. Several different methods for obtaining RPE cells through differentiation of human embryonic stem cells (hESC) have been published, many of them successful even though requiring long times. One problem in all of the published differentiation programmes is that they either contain animal-derived or non-defined components (e.g. feeder cells, human serum), making them more difficult for clinical use.

In the present disclosure, RPE cells can be derived from stem cells using feeder-free, totally chemically defined, and xeno-free methods. The term "chemically defined" means that all of the components in the medium are known chemical substances which are not isolated from any biological tissues. The term "xeno-free" means that no substances of animal origin are used in the methods. Human embryonic stem cells can be cultured on a laminin substrate, which may contain a cadherin, and differentiated into RPE cells in completely chemically defined conditions without any substances of animal origin (i.e. clinical grade RPE cells).

Initially, the stem cells are cultured using a first cell culture medium that contains a growth factor such as basic fibroblast growth factor, i.e. bFGF or FGF2, such as a TeSR2 medium or the Nutristem medium (available from Stemgent). The amount of growth factor (i.e. FGF2) in the cell culture medium is 3.9 ng/ml or less. Once the cells are almost confluent, the cells are cultured in a second cell culture medium that does not contain growth factor (i.e. FGF2), such as the TeSR2 medium described above and suitably modified. This confluence may occur after one week. After the first time period of being exposed to the first cell culture medium (containing FGF2), the cells are removed from exposure to the first cell culture medium. This can be done by draining the first cell culture medium from the laminin substrate, or alternatively the stem cells can be replated to a second laminin substrate. The stem cells are then exposed to the second cell culture medium, i.e. cultured in the second cell culture medium. The second cell culture medium is periodically changed or refreshed, for example every week. After eight weeks, the stem cells have differentiated into RPE cells. The presence of FGF2 is typically needed to maintain the stem cells in a pluripotent state, so removing its presence causes differentiation of the stem cells into RPE cells. In this example, the stem cells were exposed to the first cell culture medium (containing growth factor) for one week, and then cultured in the second cell culture medium (no growth factor) for seven weeks. In principle, 100% of the stem cells can become clinical grade RPE cells which can then be used to treat patients with AMD by subretinal injection or other transplantation processes.

Example 5

Xeno-Free Feeder-Free Differentiation of Clinical Grade Human Retinal Pigment Epithelium on Human Recombinant Laminin 521 for Treatment of Macular Degeneration Human embryonic stem cells were used that had been established in xeno-free feeder-free conditions onto the surface of a laminin-521 substrate. Human embryonic stem cells (line HS980) were pipetted onto a LN-521 substrate. The stem cells were then cultured in one of two different chemically defined xeno-free culture media (TeSR2, Stem Cell Technologies, or Nutristem, Stemgent). Both media contain FGF2, and no additional growth factors were added to these media.

Figure 25:
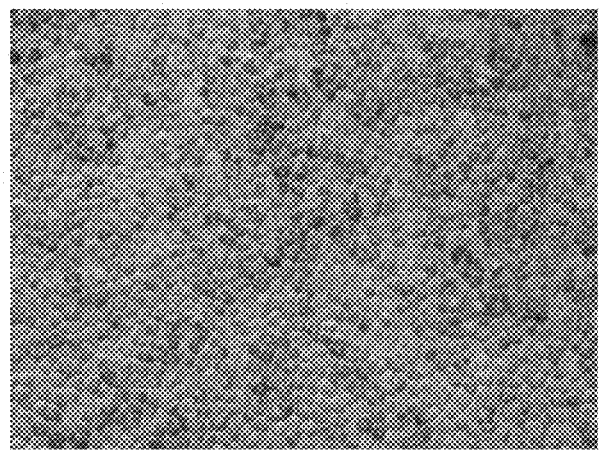
FIG. 25 is a picture of RPE cells at eight weeks, showing a cobblestone form.
Figure 26:
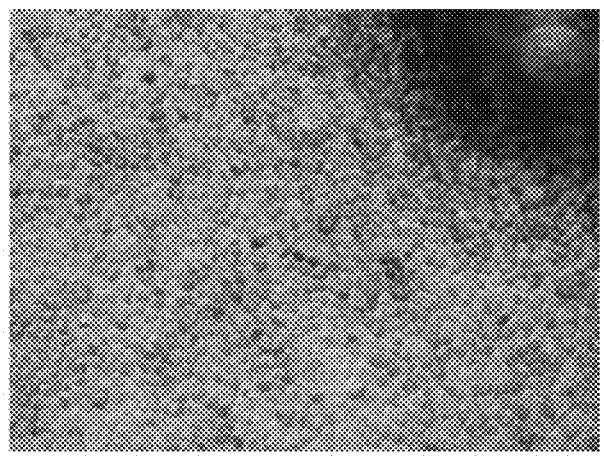
FIG. 26 is a second picture of RPE cells at eight weeks, showing a cobblestone form.

After one week, the stem cells were re-plated onto the surface of another LN-521 substrate. Next, the stem cells were exposed to a Nutristem XF medium which had been made without FGF2. The cells were maintained in those conditions, and eventually formed a monolayer with sometimes small pigmented aggregate. After six more weeks with weekly media changes of the Nutristem XF medium, the cells had differentiated to the cobblestone form typical of RPE, and there were more and more pigment in cells. After eight weeks, they have become typical RPE cells. FIG. 25 and FIG. 26 are photomicrographs showing the cobblestone form of RPE cells after eight weeks.

The RPE cells are chemically defined, and animal substance free without added chemicals or growth factors. The RPE cells grow as a monolayer instead of miscellaneous clumps or embryoid bodies that are not evenly differentiated populations. The clinical grade RPE cells can then be used to treat patients with AMD, such as by subretinal injection or other like treatments or processes.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method of obtaining retinal pigment epithelium (RPE) cells, comprising:
   culturing one or more stem cells on a substrate comprising a laminin, wherein the laminin is an intact protein or a protein fragment, and wherein the laminin is laminin-521 or laminin-511;
   exposing the stem cells to a first cell culture medium that contains a growth factor;
   after a first time period, removing the first cell culture medium and exposing the stem cells to a second cell culture medium that does not contain the growth factor; and
   periodically changing the second cell culture medium to obtain the RPE cells.

2. The method of claim 1, wherein the laminin is an effective recombinant laminin.

3. The method of claim 1, wherein the substrate further comprises a cadherin.

4. The method of claim 3, wherein the cadherin is e-cadherin.

5. The method of claim 3, wherein the weight ratio of the laminin to the cadherin is from about 5:1 to about 15:1.

6. The method of claim 3, wherein the weight ratio of laminin-521 to e-cadherin is from about 5:1 to about 15:1.

7. The method of claim 1, wherein the first cell culture medium contains FGF2 in an amount of greater than zero to 3.9 ng/ml.

8. The method of claim 1, wherein the second cell culture medium has no FGF2.

9. The method of claim 1, wherein the substrate, the first cell culture medium, and the second cell culture medium do not contain any substances of animal origin.

10. The method of claim 1, wherein the first time period is about one week.

11. The method of claim 1, wherein periodic changing of the second cell culture medium occurs every week, and the RPE cells are obtained after a total of about eight weeks.

12. The method of claim 1, wherein the stem cells are exposed to the first cell culture medium for about one week, and are exposed to the second cell culture medium for about seven weeks, to obtain the RPE cells.

13. The method of claim 1, wherein the first and the second medium are xeno-free.

14. The method of claim 1, wherein the first and the second medium are chemically defined.

* * * * *

SEQUENCE LISTING

```
Sequence total quantity: 8
SEQ ID NO: 1              moltype = AA  length = 3695
FEATURE                   Location/Qualifiers
source                    1..3695
                          mol_type = protein
                          organism = Homo sapiens
SEQUENCE: 1
MAKRLCAGSA LCVRGPRGPA PLLLVGLALL GAARAREEAG GGFSLHPPYF NLAEGARIAA   60
SATCGEEAPA RGSPRPTEDL YCKLVGGPVA GGDPNQTIRG QYCDICTAAN SNKAHPASNA  120
IDGTERWWQS PPLSRGLEYN EVNVTLDLGQ VFHVAYVLIK FANSPRPDLW VLERSMDFGR  180
TYQPWQFFAS SKRDCLERFG PQTLERITRD DAAICTTEYS RIVPLENGEI VVSLVNGRPG  240
AMNFSYSPLL REFTKATNVR LRFLRTNTLL GHLMGKALRD PTVTRRYYYS IKDISIGGRC  300
VCHGHADACD AKDPTDPFRL QCTCQHNTCG GTCDRCCPGF NQQPWKPATA NSANECQSCN  360
CYGHATDCYY DPEVDRRRAS QSLDGTYQGG GVCIDCQHHT TGVNCERCLP GFYRSPNHPL  420
DSPHVCRRCN CESDFTDGTC EDLTGRCYCR PNFSGERCDV CAEGFTGFPS CYPTPSSSND  480
TREQVLPAGQ IVNCDCSAAG TQGNACRKDP RVGRCLCKPN FQGTHCELCA PGFYGPGCQP  540
CQCSSPGVAD DRCDPDTGQC RCRVGFEGAT CDRCAPGYFH FPLCQLCGCS PAGTLPEGCD  600
EAGRCLCQPE FAGPHCDRCR PGYHGFPNCQ ACTCDPRGAL DQLCGAGGLC RCRPGYTGTA  660
CQECSPGFHG FPSCVPCHCS AEGSLHAACD PRSGQCSCRP RVTGLRCDTC VPGAYNFPYC  720
EAGSCHPAGL APVDPALPEA QVPCMCRAHV EGPSCDRCKP GFWGLSPSNP EGCTRCSCDL  780
RGTLGGVAEC QPGTGQCFCK PHVCGQACAS CKDGFFGLDQ ADYFGCRSCR CDIGGALGQS  840
CEPRTGVCRC RPNTQGPTCS EPARDHYLPD LHHLRLELEE AATPEGHAVR FGFNPLEFEN  900
FSWRGYAQMA PVQPRIVARL NLTSPDLFWL VFRYVNRGAM SVSGRVSVRE EGRSATCANC  960
TAQSQPVAFP PSTEPAFITV PQRGFGEPFV LNPGTWALRV EAEGVLLDYV VLLPSAYYEA 1020
ALLQLRVTEA CTYRPSAQQS GDNCLLYTHL PLDGFPSAAG LEALCRQDNS LPRPCPTEQL 1080
SPSHPPLITC TGSDVDVQLQ VAVPQPGRYA LVVEYANEDA RQEVGVAVHT PQRAPQQGLL 1140
SLHPCLYSTL CRGTARDTQD HLAVFHLDSE ASVRLTAEQA RFFLHGVTLV PIEEFSPEFV 1200
EPRVSCISSH GAFGPNSAAC LPSRFPKPPQ PIILRDCQVI PLPPGLPLTH AQDLTPAMSP 1260
AGPRPRPPTA VDPDAEPTLL REPQATVVFT THVPTLGRYA FLLHGYQPAH PTFPVEVLIN 1320
AGRVWQGHAN ASFCPHGYGC RTLVVCEGQA LLDVTHSELT VTVRVPKGRW LWLDYVLVVP 1380
ENVYSFGYLR EEPLDKSYDF ISHCAAQGYH ISPSSSSLFC RNAAASLSLF YNNGARPCGC 1440
HEVGATGPTC EPFGGQCPCH AHVIGRDCSR CATGYWGPPN CRPCDCGARL CDELTGQCIC 1500
PPRTIPPDCL LCQPQTFGCH PLVGCEECNC SGPGIQELTD PTCDTDSGQC KCRPNVTGRR 1560
CDTCSPGFHG YPRCRPCDCH EAGTAPGVCD PLTGQCYCKE NVQGPKCDQC SLGTFSLDAA 1620
NPKGCTRCFC FGATERCRSS SYTRQEFVDM EGWVLLSTDR QVVPHERQPG TEMLRADLRH 1680
VPEAVPEAFP ELYWQAPPSY LGDRVSSYGG TLRYELHSET QRGDVFVPME SRPDVVLQGN 1740
QMSITFLEPA YPTPGHVHRG QLQLVEGNFR HTETRNTVSR EELMMVLASL EQLQIRALFS 1800
QISSAVFLRR VALEVASPAG QGALASNVEL CLCPASYRGD SCQECAPGFY RDVKGLFLGR 1860
```

```
CVPCQCHGHS DRCLPGSGVC VDCQHNTEGA HCERCQAGFV SSRDDPSAPC VSCPCPLSVP   1920
SNNFAEGCVL RGGRTQCLCK PGYAGASCER CAPGFFGNPL VLGSSCQPCD CSGNGDPNLL   1980
FSDCDPLTGA CRGCLRHTTG PRCEICAPGF YGNALLPGNC TRCDCTPCGT EACDPHSGHC   2040
LCKAGVTGRR CDRCQEGHFG FDGCGGCRPC ACGPAAEGSE CHPQSGQCHC RPGTMGPQCR   2100
ECAPGYWGLP EQGCRRCQCP GGRCDPHTGR CNCPPGLSSE RCDTCSQQHQ VPVPGGPVGH   2160
SIHCEVCDHC VVLLLDDLER AGALLPAIHE QLRGINASSM AWARLHRLNA SIADLQSQLR   2220
SPLGPRHETA QQLEVLEQQS TSLGQDARRL GGQAVGTRDQ ASQLLAGTEA TLGHAKTLLA   2280
AIRAVDRTLS ELMSQTGHLG LANASAPSGE QLLRTLAEVE RLLWEMRARD LGAPQAAAEA   2340
ELAAAQRLLA RVQEQLSSLW EENQALATQT RDRLAQHEAG LMDLREALNR AVDATREAQE   2400
LNSRNQERLE EALQRKQELS RDNATLQATL HAARDTLASV FRLLHSLDQA KEELERLAAS   2460
LDGARTPLLQ RMQTFSPAGS KLRLVEAAEA HAQQLGQLAL NLSSIILDVN QDRLTQRAIE   2520
ASNAYSRILQ AVQAAEDAAG QALQQADHTW ATVVRQGLVD RAQQLLANST ALEEAMLQEQ   2580
QRLGLVWAAL QGARTQLRDV RAKKDQLEAH IQAAQAMLAM DTDETSKKIA HAKAVAAEAQ   2640
DTATRVQSQL QAMQENVERW QGQYEGLRGQ DLGQAVLDAG HSVSTLEKTL PQLLAKLSIL   2700
ENRGVHNASL ALSASIGRVR ELIAQARGAA SKVKVPMKFN GRSGVQLRTP RDLADLAAYT   2760
ALKFYLQGPE PEPGQGTEDR FVMYMGSRQA TGDYMGVSLR DKKVHWVYQL GEAGPAVLSI   2820
DEDIGEQFAA VSLDRTLQFG HMSVTVERQM IQETKGDTVA PGAEGLLNLR PDDFVFYVGG   2880
YPSTFTPPPL LRFPGYRGCI EMDTLNEEVV SLYNFERTFQ LDTAVDRPCA RSKSTGDPWL   2940
TDGSYLDGTG FARISFDSQI STTKRFEQEL RLVSYSGVLF FLKQQSQFLC LAVQEGSLVL   3000
LYDFGAGLKK AVPLQPPPPL TSASKAIQVF LLGGSRKRVL VRVERATVYS VEQDNDLELA   3060
DAYYLGGVPP DQLPPSLRRL FPTGGSVRGC VKGIKALGKY VDLKRLNTTG VSAGCTADLL   3120
VGRAMTFHGH GFLRLALSNV APLTGNVYSG FGFHSAQDSA LLYYRASPDG LCQVSLQQGR   3180
VSLQLLRTEV KTQAGFADGA PHYVAFYSNA TGVWLYVDDQ LQQMKPHRGP PPELQPQPEG   3240
PPRLLLGGLP ESGTIYNFSG CISNVFVQRL LGPQRVFDLQ QNLGSVNVST GCAPALQAQT   3300
PGLGPRGLQA TARKASRRSR QPARHPACML PPHLRTTRDS YQFGGSLSSH LEFVGILARH   3360
RNWPSLSMHV LPRSSRGLLL FTARLRPGSP SLALFLSNGH FVAQMEGLGT RLRAQSRQRS   3420
RPGRWHKVSV RWEKNRILLV TDGARAWSQE GPHRQHQGAE HPQPHTLFVG GLPASSHSSK   3480
LPVTVGFSGC VKRLRLHGRP LGAPTRMAGV TPCILGPLEA GLFFPGSGGV ITLDLPGATL   3540
PDVGLELEVR PLAVTGLIFH LGQARTPPYL QLQVTEKQVL LRADDGAGEF STSVTRPSVL   3600
CDGQWHRLAV MKSGNVLRLE VDAQSNHTVG PLLAAAAGAP APLYLGGLPE PMAVQPWPPA   3660
YCGCMRRLAV NRSPVAMTRS VEVHGAVGAS GCPAA                              3695

SEQ ID NO: 2            moltype = AA  length = 1811
FEATURE                 Location/Qualifiers
source                  1..1811
                        mol_type = protein
                        organism = Homo sapiens
SEQUENCE: 2
MELTSRERGR GQPLPWELRL GLLLSVLAAT LAQAPAPDVP GCSRGSCYPA TGDLLVGRAD     60
RLTASSTCGL NGPQPYCIVS HLQDEKKCFL CDSRRPFSAR DNPHSHRIQN VVTSFAPQRR    120
AAWWQSENGI PAVTIQLDLE AEFHFTHLIM TFKTFRPAAM LVERSADFGR TWHVYRYFSY    180
DCGADFPGVP LAPPRHWDDV VCESRYSEIE PSTEGEVIYR VLDPAIPIPD PYSSRIQNLL    240
KITNLRVNLT RLHTLGDNLL DPRREIREKY YYALYELVVR GNCFCYGHAS ECAPAPGAPA    300
HAEGMVHGAC ICKHNTRGLN CEQCQDFYRD LPWRPAEDGH SHACRKCECH GHTHSCHFDM    360
AVYLASGNVS GGVCDGCQHN TAGRHCELCR PFFYRDPTKD LRDPAVCRSC DCDPMGSQDG    420
GRCDSHDDPA LGLVSGQCRC KEHVVGTRCQ QCRDGFFGLS ISDRLGCRRC QCNARGTVPG    480
STPCDPNSGS CYCKRLVTGR GCDRCLPGHW GLSHDLLPCD PCDCDVGGAL DPQCDEGTGQ    540
CHCRQHMVGR RCEQVQPGYF RPFLDHLIWE AEDTRGQVLD VVERLVTPGE TPSWTGSGFV    600
RLQEGQTLEF LVASVPKAMD YDLLLRLEPQ VPEQWAELEL IVQRPGPVPA HSLCGHLVPK    660
DDRIQGTLQP HARYLIFPNP VCLEPGISYK LHLKLVRTGG SAQPETPYSG PGLLIDSLVL    720
LPRVLVEMPF SGGDAAALER QATFERYQCH EEGLVYPSKTS PSEACAPLLI SLSTLIYNGA    780
LPCQCNPQGS LSSECNPHGG QCLCKPGVVG RRCDLCAPGY YGFGPTGCQA CQCSHEGALS    840
SLCEKTSGQC LCRTGAFGLR CDRCQRGQWG FPSCRPCVCN GHADECNTHT GACLGCRDHT    900
GGEHCERCIA GFHGDPRLPY GGQCRPCPCP EGPGSQRHFA TSCHQDEYSQ QIVCHCRAGY    960
TGLRCEACAP GHFGDPSRPG GRCQLRCECS NIDPMDPDCN DPHTGQCLRC LHHTEGPHCA   1020
HCKPGFHGQA ARQSCHRCTC NLLGTNPQQC PSPDQHCDP SSGQCPCLPN VQGPSCDRCA   1080
PNFWNLTSGH GCQPCACHPS RARGPTCNEF TGQCHCRAGF GGRTCSECQE LHWGDPGLQC   1140
HACDCDSRGI DTPQCHRFTG HCSCRPGVSG VRCDQCARGF SGIFPACHPC HACFGDWDRV   1200
VQDLAARTQR LEQRAQELQQ TGVLGAFESS FWHMQEKLGI VQGIVGARNT SAASTAQLVE   1260
ATEELRREIG EATEHLTQLE ADLTDVQDEN FNANHALSGL ERDRLALNLT LRQLDQHLDL   1320
LKHSNFLGAY DSIRHAHSQS AEAERRNANTS ALAVPSPVSN SASARHRTEA LMDAQKEDFN   1380
SKHMANQRAL GKLSAHTHTL SLTDINELVC GAPGDAPCAT SPCGGAGCRD EDGQPRCGGL   1440
SCNGAAATAD LALGRARHTQ AELQRALAEG GSILSRVAET RRQASEAQQR AQAALDKANA   1500
SRGQVEQANQ ELQELIQSVK DFLNQEGADP DSIEMVATRV LELSIPASAE QIQHLAGAIA   1560
ERVRSLADVD AILARTVGDV RRAEQLLQDA RRARSWAEDE KQKAETVQAA LEEAQRAQGI   1620
AQGAIRGAVA DTRDTEQTLY QVQERMAGAE RALSSAGERA RQLDALLEAL KLKRAGNSLA   1680
ASTAEETAGS AQGRAQEAEQ LLRGPLGDQY QTVKALAERK AQGVLAAQAR AEQLRDEARD   1740
LLQAAQDKLQ RLQELEGTYE ENERALESKA AQLDGLEARM RSVLQAINLQ VQIYNTCQKS   1800
SWPGRAPNKP V                                                       1811

SEQ ID NO: 3            moltype = AA  length = 1609
FEATURE                 Location/Qualifiers
source                  1..1609
                        mol_type = protein
                        organism = Homo sapiens
SEQUENCE: 3
MRGSHRAAPA LRPRGRLWPV LAVLAAAAAA GCAQAAMDEC TDEGGRPQRC MPEFVNAAFN     60
VTVVATNTCG TPPEEYCVQT GVTGVTKSCH LCDAGQPHLQ HGAAFLTDYN NQADTTWWQS    120
QTMLAGVQYP SSINLTLHLG KAFDITYVRL KFHTSRPESF AIYKRTREDG PWIPYQYYSG    180
```

```
SCENTYSKAN RGFIRTGGDE QQALCTDEFS DISPLTGGNV AFSTLEGRPS AYNFDNSPVL   240
QEWVTATDIR VTLNRLNTFG DEVFNDPKVL KSYYYAISDF AVGGRCKCNG HASECMKNEF   300
DKLVCNCKHN TYGVDCEKCL PFFNDRPWRR ATAESASECL PCDCNGRSQE CYFDPELYRS   360
TGHGGHCTNC QDNTDGAHCE RCRENFFRLG NNEACSSCHC SPVGSLSTQC DSYGRCSCKP   420
GVMGDKCDRC QPGFHSLTEA GCRPCSCDPS GSIDECNIET GRCVCKDNVE GFNCERCKPG   480
FFNLESSNPR GCTPCFCFGH SSVCTNAVGY SVYSISSTFQ IDEDGWRAEQ RDGSEASLEW   540
SSERQDIAVI SDSYFPRYFI APAKFLGKQV LSYGQNLSFS FRVDRRDTRL SAEDLVLEGA   600
GLRVSVPLIA QGNSYPSETT VKYVFRLHEA TDYPWRPALT PFEFQKLLNN LTSIKIRGTY   660
SERSAGYLDD VTLASARPGP GVPATWVESC TCPVGYGGQF CEMCLSGYRR ETPNLGPYSP   720
CVLCACNGHS ETCDPETGVC NCRDNTAGPH CEKCSDGYYG DSTAGTSSDC QPCPCPGGSS   780
CAVVPKTKEV VCTNCPTGTT GKRCELCDDG YFGDPLGRNG PVRLCRLQCS SDNIDPNAVG   840
NCNRLTGECL KCIYNTAGFY CDRCKDGFFG NPLAPNPADK CKACNCNLYG TMKQQSSCNP   900
VTGQCECLPH VTGQDCGACD PGFYNLQSGQ GCERCDCHAL GSTNGQCDIR TGQCECQPGI   960
TGQHCERCEV NHFGFGPEGC KPCDCHPEGS LSLQCKDDGR CECREGFVGN RCDQCEENYF  1020
YNRSWPGCQE CPACYRLVKD KVADHRVKLQ ELESLIANLG TGDEMVTDQA FEDRLKEAER  1080
EVMDLLREAQ DVKDVDQNLM DRLQRVNNTL SSQISRLQNI RNTIEETGNL AEQARAHVEN  1140
TERLIEIASR ELEKAKVAAA NVSVTQPEST GDPNNMTLLA EEARKLAERH KQEADDIVRV  1200
AKTANDTSTE AYNLLLRTLA GENQTAFEIE ELNRKYEQAK NISQDLEKQA ARVHEEAKRA  1260
GDKAVEIYAS VAQLSPLDSE TLENEANNIK MEAENLEQLI DQKLKDYEDL REDMRGKELE  1320
VKNLLEKGKT EQQTADQLLA RADAAKALAE EAAKKGRDTL QEANDILNNL KDFDRRVNDN  1380
KTAAEEALRK IPAINQTITE ANEKTREAQQ ALGSAAADAT EAKNKAHEAE RIASAVQKNA  1440
TSTKAEAERT FAEVTDLDNE VNNMLKQLQE AEKELKRKQD DADQDMMMAG MASQAAQEAE  1500
INARKAKNSV TSLLSIINDL LEQLGQLDTV DLNKLNEIEG TLNKAKDEMK VSDLDRKVSD  1560
LENEAKKQEA AIMDYNRDIE EIMKDIRNLE DIRKTLPSGC FNTPSIEKP             1609

SEQ ID NO: 4              moltype = DNA   length = 5518
FEATURE                   Location/Qualifiers
source                    1..5518
                          mol_type = other DNA
                          organism = Homo sapiens
SEQUENCE: 4
atggagctga cctcaaggga aagagggagg ggacagcctc tgccctggga acttcgactg    60
ggcctactgc taagcgtgct ggctgccaca ctggcacagg ccctgcccc ggatgtgcct    120
ggctgttcca ggggaagctg ctaccccgcc acgggcgacc tgctggtggg ccgagctgac    180
agactgactg cctcatccac ttgtgcgctg aatggcccc agccctactg catcgtcagt    240
cacctgcagg acgaaaagaa gtgcttcctt tgtgactccc ggcgcccctt ctctgctaga    300
gacaacccac acagccatcg catccagaat gtagtcacca gctttgcacc acagcggcgg    360
gcagcctggt ggcagtcaga gaatggtatc cctgcggtca ccatccagct ggacctggag    420
gctgagtttc atttcacaca cctcattatg accttcaaga catttcgcc tgctgccatg    480
ctggtgaaac gctcagcaga ctttggccgc acctggcatg tgtaccgata tttctcctat    540
gactgtgggg ctgacttccc aggagtccca ctagcacccc cacggcactg ggatgatgta    600
gtctgtgagt cccgctactc agagattgag ccatccactg aaggcgaggt catctatcgt    660
gtgctggacc ctgccatccc tatcccagac ccctacagct cacggattca gaacctgttg    720
aagatcacca acctacgggt gaacctgact cgtctacaca cgttgggaga caacctactc    780
gacccacgga gggagatccg agagaagtac tactatgccc tctatgagct ggttgtacgt    840
ggcaactgct tctgctacgg cacacgcctca gagtgtgcac ccgccccagg gcaccagcc    900
catgctgagg catggtgca cggagcttgc atctgcaaac acaacacagc tggcctcaac    960
tgcgagcagt gtcaggattt ctatcgtgac ctgcccggc gtccggctga ggacggcat   1020
agtcatgcct gtaggaagtg tgagtgccat gggcacaccc acagctgcca cttcgacatg   1080
gccgtatacc tggcatctgg caatgtgagt ggaggtgtgt gtgatggatg tcagcataac   1140
acagctgggc gccactgtga gctctgtcgc ccttcttct accgtgaccc aaccaaggac   1200
ctgcgggatc cggctgtgtg ccgctcctgt gattgtgacc ccatgggttc tcaagacggt   1260
ggtcgctgtg attcccatga tgaccctgca ctgggactgg tctccggcca gtgtcgctgc   1320
aaagaacatg tggtgggcac tcgctgccag caatgccgtg atggcttctt gggctcagc   1380
atcagtgacc gtctgggctg ccggcgatgt caatgtaatg cacggggcac agtgcctggg   1440
agcactcctt gtgaccccaa cagtggatcc tgttactgca aacgtctagt gactggacgt   1500
ggatgtgacc gctgcctgcc tggccactgg ggctgagcc acgacctgct cggctgccgc   1560
ccctgtgact gcgacgtggg tggtgctttg gatcccagt gtgatgaggg cacaggtcaa   1620
tgccactgcc gccagcacat ggttgggcga cgctgtgagc aggtgcaacc tggctacttc   1680
cggcccttcc tggaccacct aatttgggag gctgaggaca cccgagggca ggtgctcgat   1740
gtggtggagc gcctggtgac cccgggaa actccatcct ggactggctc aggcttcgtg   1800
cggctacagg aagtcagac cctggagttc ctggtggcct ctgtgccgaa ggctatggac   1860
tatgacctgc tgctgcgctt agagcccag tccctgagc aatgggcaga gttggaactg   1920
attgtgcagc gtcagggcc tgtgcctgcc cacagcctgt gtgggcattt ggtgcccaag   1980
gatgatcgca tccaagggac tctgcaacca catgccaggt acttgatatt tcctaatcct   2040
gtctgccttg agcctggtat tcctacaag ctgcatctga agctggtacg dacaggggga   2100
agtgcccagc ctgagactcc ctactctgga cctggcctgc tcattgactc gctggtgctg   2160
ctgccccgtg tcctggtgct agagatgttt agtggggggtg atgctgctgc cctggagcgc   2220
caggccacct ttgaacgcta ccaatgccat gaggagggtc tggtgcccag caagacttcc   2280
ccctctgagg cctgcgcacc cctcctcatc agcctgtcca ccctcatcta caatggtgcc   2340
ctgccatgtc agtgcaaccc tcaaggttca ctgagttctg agtgcaaccc tcatggtggt   2400
cagtgcctgt gcaagcctgg agtggttggg cgccgctgtg acctctgtgc ccctggctac   2460
tatggctttg gccccacagg ctgtcaagcc tgccagtgca gccacgaggg ggcactcagc   2520
agtctctgga aaaagaccag tgggcaatgt gtctgtcgaa ctgtgctggt tggcttgtgc   2580
tgtgaccgtg gccagcctgg ccagtgggaa ttccctagct gccggccatg tgtctgcaat   2640
gggcatgcag atgagtgcaa cacccacaca ggcgcttgcc tggctgccgc tgatcacaca   2700
gggggtgagc actgtgaaag gtgcattgct ggtttccacg ggacccacg ctgccatat   2760
ggggccagt gccggccctg tcctgtcct gaaggccctg ggagccaacg gcactttgct   2820
acttcttgcc accaggatga atattcccag cagattgtgt gccactgccg ggcaggctat   2880
```

```
acggggctgc gatgtgaagc ttgtgccccct gggcactttg gggacccatc aaggccaggt    2940
ggccggtgcc aactgtgtga gtgcagtggg aacattgacc caatggatcc tgatgcctgt    3000
gacccccaca cggggcaatg cctgcgctgt ttacaccaca cagagggtcc acactgctgcc   3060
cactgcaagc ctggcttcca tgggcaggct gcccgacaga gctgtcaccg ctgcacatgc    3120
aacctgctgg gcacaaatcc gcagcagtgc ccatctcctg accagtgcca ctgtgatcca    3180
agcagtgggc agtgcccatg cctccccaat gtccagggcc ctagctgtga ccgctgtgcc    3240
cccaacttct ggaacctcac cagtggccat ggttgccagc cttgtgcctg ccacccaagc    3300
cgggccagag gccccacctg caacgagttc acagggcagt gccactgccg tgccggcttt    3360
ggagggcgga cttgttctga gtgccaagag ctccactggg gagacctgg gttgcagtgc     3420
catgcctgtg attgtgactc tcgtggaata gatacacctc agtgtcaccg cttcacaggt    3480
cactgcagct gccgcccagg ggtgtctggt gtgcgctgtg accagtgtgc ccgtggcttc    3540
tcaggaatcc ttcctgcctg ccatccctgc catgcatgct tcggggattg ggaccgagtg    3600
gtgcaggact tggcagcccg tacacagcgc ctagagcagc gggcgcagga gttgcaacag    3660
acgggtgtgc tgggtgcctt tgagagcagc ttctgcaca tgcaggagaa gctgggcatt     3720
gtgcagggca tcgtaggtgc ccgcaacacc tcagccgcct ccactgcaca gcttgtggaa    3780
gccacagagg agctgcggcg tgaaattggg gaggccactg agcacctgac tcagctcgag    3840
gcagacctga cagatgtgca agatgagaac ttcaatgcca accatgcact aagtggtctg    3900
gagcgagata ggcttgcact taatctcaca ctgcggcagc tcgaccagca tcttgacttg    3960
ctcaaacatt caaacttcct gggtgcctat gacagcatcc ggcatgccca tagccagtct    4020
gcagaggcag aacgtcgtgc caatacctca gccctggcag tacctagccc tgtgagcaac    4080
tcggcaagtg ctcggcatcg gacagaggca ctgatggatg tcagaagga ggacttcaac      4140
agcaaacaca tggccaacca gcgggcactt ggcaagctct ctgcccatac ccacacccctg   4200
agcctgacag acataaatga gctggtctgt ggggccaccag gggatgcacc ctgtgctaca    4260
agcccttgtg ggggtgccgg ctgtcgagat gaggatgggc agccgcgctg tggggggcctc  4320
agctgcaatg gggcagcggc tacagcagac ctagcactgg gccgggcccg gcacacacag    4380
gcagagctgc agcgggcact ggcagaaggt ggtagcatcc tcagcagagt cctgagact     4440
cgtcggcagg caagcgaggc acagcagcgg gcccaggcag ccctggacaa ggctaatgct    4500
tccaggggac aggtggaaca ggccaaccag gaacttcaag aacttatcca gagtgtgaag    4560
gacttcctca accaggaggg ggctgatcct gatagcattg aaatggtggc cacacgggtg    4620
ctagagctct ccatcccagc ttcagctgag cagatccgag acctggccgg tgcgattgca    4680
gagcgagtcc ggagcctggc agatgtggat gcgatcctgg cacgtactgt aggagatgtg    4740
cgtcgtgccg agcagctact gcaggatgca cggcgggcaa ggagctgggc tgaggatgag    4800
aaacagaagg cagagacagt acaggcagca ctggaggagg cccagcgggc acagggtatt    4860
gcccagggtg ccatccgggg ggcagtggct gacacacggg acacagagca gaccctgtac    4920
caggtacagg agaggatggc aggtgcagag cgggcactga gctctgcagg tgaaagggct    4980
cggcagttgg atgctctcct ggaggctctg aaattgaaac gggcaggaaa tagtctggca    5040
gcctctacag cagaagaaac ggcaggcagt gcccagggtc gtgcccagga ggctgagcag    5100
ctgctacgcg gtcctctggg tgatcagtac cagacgtgta aggcccctagc tgagcgcaag   5160
gcccaaggtg tgctggctgc acaggcaagg gcagaacaac tgcgggatga ggctcgggac    5220
ctgttgcaag ccgctcagga caagctgcag cggctacagg aattggaagg cacctatgag    5280
gaaaatgagc gggcactgga gagtaaggca gcccagttgg acgggttgga ggccaggatg    5340
cgcagcgtgc ttcaagccat caacttcag gtgcagatct acaacacctg ccagtgaccc     5400
ctgccaaagg cctaccccag ttcctagcac tgcccccacat gcatgcctgc ctatgcactg    5460
aagagctctt ggcccggcag ggcccccaat aaaccagtgt gaaccccccaa aaaaaaaa     5518

SEQ ID NO: 5          moltype = DNA  length = 11426
FEATURE               Location/Qualifiers
source                1..11426
                      mol_type = other DNA
                      organism = Homo sapiens
SEQUENCE: 5
agacccgccg ggctcccgcc gcgcgcgctg tccctggagc tcgggacgc ggccccggagc     60
cgggaagatg gcgaagcggc tctgcgcggg gagcgcactg tgtgttcgcg gccccccgggg   120
ccccgcgccg ctgctgctgg tcgggctggc gctgctgggc gcggcgcggg cgcgggagga    180
ggcgggcggc ggcttcagcc tgcacccgcc ctacttcaac ctggccgagg gcgcccgcat    240
cgccgcctcc gcgacctgcg gagaggaggc cccggcgcgg ggctcccgc gccccaccga    300
ggacctttac tgcaagctgg taggggcccc cgtggccggc ggcgacccca accagaccat    360
ccggggccag tactgtgaca tctgcacggc tgccaacagc aacaaggcac accccgcgag    420
caatgccatc gatggcacgg agcgctggtg gcagagtcca gcctgtcccc gcggcctgga    480
gtacaacgag gtcaacgtca ccctggacct gggccaggtc ttccacgtgg cctacgtcct    540
catcaagttt gccaactcac cccggccgga cctctggtgt ctggagcggt ccatggactt    600
cggccgcacc taccagccct ggcagttctt tgcctcctcc aagagggact gtctggagcg    660
gttcgggcca cagacgctgg agcgcatcac acgggacgac gcggccatct gcaccaccga    720
gtactcacgc atcgtgcccc tggagaacgg agagatcgtg gtgtccctgg tgaacggacg    780
tccgggcgcc atgaatttct cctactcgcc gctgctacgc gagttcacca aggccaccaa    840
cgtccgcctg cgcttcctgc gtaccaacac gctgctgggc catctcatgg ggaaggcgct    900
gcgggacccc acgtcacccc gcggtgtatta ttacagcatc aaggatatca gcatcggagg    960
ccgctgtgtc tgcacacggcc acgcggatgc tgcgatgcaa aaagaccca cggacccgtt   1020
caggctgcag tgcacctgcc agcacaacac ctgcgggggc acctgcgacc gctgctgccc    1080
cggcttcaat cagcagccgt ggaagcctgc gactgccaac agtgccaacg agtgccagtc    1140
ctgtaactgc tacggccatg ccaccgactg ttactacgac cctgaggtgg accggcgccg    1200
cgccagccag agcctggatg caccatca gggtgggggt gtctgtatcg actgccagca     1260
ccacaccacc ggcgtcaact gtgagcgctg cctgccccgg ttctaccgct cccccaacca    1320
ccctcctgac tcgccccacg tctgccgccg tgcaactgc gagtccgact tcaacggtgc     1380
cacctgcgag gacctgacgg gtcgatgcta ctgccggccc aacttctctg gggagcggtg    1440
tgacgtgtgt gccgagggct tcacgggctt cccaagctgc taccgacgc cctcgtcctc    1500
caatgacacc agggagcagg tgctgccagc cggccagatt tgaattgtg actgcagcgc    1560
ggcagggacc cagggcaacg cctgccggaa ggacccaagg gtgggacgct gtctgtgcaa    1620
acccaacttc caaggcaccc attgtgagct ctgcgcgcca gggttctacg gccccggctg    1680
```

-continued

```
ccagccctgc cagtgttcca gccctggagt ggccgatgac cgctgtgacc ctgacacagg 1740
ccagtgcagg tgccgagtgg gcttcgaggg ggccacatgt gatcgctgtg ccccccggcta 1800
cttcacttc cctctctgcc agttgtgtgg ctgcagccct gcaggaacct tgcccgaggg 1860
ctgcgatgag gccggccgct gcctatgcca gcctgagttt gctggacctc attgtgaccg 1920
gtgccgccct ggctaccatg gtttcccaa ctgccaagca tgcacctgcg accctcgggg 1980
agccctggac cagctctgtg gggcgggagg tttgtgccgc tgccgccccg gctacacagg 2040
cactgcctgc caggaatgca gccccggctt tcacggcttc cccagctgtg tccctgcca 2100
ctgctctgct gaaggctccc tgcacgcagc ctgtgacccc cggagtgggc agtgcagctg 2160
ccggcccgt gtgacggggc tgcggtgtga cacatgtgtg cccggtgcct acaacttccc 2220
ctactgcgaa gctggctctt gccaccctgc cggtctgcc ccagtggatc ctgcccttcc 2280
tgaggcacag gttccctgta tgtgccgggc tcacgtggag gggccgagct gtgaccgctg 2340
caaacctggg ttctggggac tgagcccag caacccgag ggctgtaccc gctgcagctg 2400
cgacctcagg ggcacactgg gtggagttgc tgagtgccag ccgggcaccg gccagtgctt 2460
ctgcaagccc cacgtgtgcg gccaggcctg cgcgtcctgc aaggatggct tcttttggact 2520
ggatcaggct gactatttg gctgccgcag ctgccggtgt gacattggcg gtgcactggg 2580
ccagagctgt gaaccgagga cgggcgtctg ccggtgccgc cccaacaccc agggcccac 2640
ctgcagcgag cctgcgaggg accactacct cccggacctg caccacctgc gcctggagct 2700
ggaggaggcct gccacacctg agggtcacgc cgtgcgcttt ggcttcaacc ccctcgagtt 2760
cgagaacttc agctggaggg gctacgcgca gatggcaccct gtccagccca ggatcgtggc 2820
caggctgaac ctgacctccc ctgaccttt ctggctcgtc ttccgatacg tcaaccgggg 2880
ggccatgagt gtgagcgggc gggtctctgt gcgagaggag ggcaggtcgg ccacctgcgc 2940
caactgcaca gcacagagtc agcccgtggc cttcccaccc acggggactc ctgccttcat 3000
caccgtgccc cagaggggct tcggagagcc cttttgtgctg aaccctggca cctgggcct 3060
gcgtgtggag gccgaagggg tgctcctgga ctacgtggtt ctgctgccta gcgcatacta 3120
cgaggcgcg ctcctgcagc tgcgggtgac tgaggcctgc atataccgtc cctctgccca 3180
gcagtctggc gacaactgcc tcctctacac acacctcccc ctggatggct tcccctacag 3240
cgccgggctg gaggccctgt gtcgccagga caacagcctg cccccggccct gccccacgga 3300
gcagctcagc ccgtcgcacc cgccactgat cacctgcacg ggcagtgatg tggacgtcca 3360
gcttcaagtg gcagtgccac agccaggccg ctatgcccta gtggtggagt acgccaatga 3420
ggatgcccgc caggaggtgg gcgtggccgt gcacacccca cagccgggcc cccagcaggg 3480
gctgctctcc ctgcacccct gcctgtacag caccctgtgc cggggcactg cccgggatac 3540
ccaggaccac ctggctgtct tccacctgga ctcggaggcc agcgtgaggc tcacagccga 3600
acaggcacgc ttcttcctgc acgggtcac tctggtgccc attgaggagt tcagcccgga 3660
gttcgtggag cccccgggtca gctgcatcag cagccacggc gcctttggcc ccaacagtgc 3720
cgcctgtctg ccctcgcgct tcccaaagcc gccccactcca gggactgcca 3780
ggtgatcccg ctgccgccg gcctcccgct gacccacgcg caggatctca ctccagccat 3840
gtccccagct ggaccccgac ctcggccccc caccgctgtg gacctgatg cagagccac 3900
cctgctgcgt gagcccagg ccaccgtggt cttcaccacc catgtgccca cgctgggccg 3960
ctatgccttc ctgctgcacg gctaccagcc agccaccct accctccccg tggaagtcat 4020
catcaacgcc ggccgcgtgt ggcagggcca cgccaaccgc agcttctgtc cacatgcta 4080
cggctgccgc accctggtgg tgtgtgaggg ccaggccctg ctggacgtga cccacagcga 4140
gctcactgtg accgtgcgtg tgcccaaggg ccggtggctc tggctggatt atgtactcgt 4200
ggtccctgag aacgtctaca gctttgcta cctccgggag gagcccctgg ataaatccta 4260
tgacttcatc agccactgcg cagcccaggg ctaccacatc agcccagca gctcatcct 4320
gttctgccga aacgctgctg cttcctctc cctcttctat aacaacgag cccgtccatg 4380
tggctgccac gaagtaggtg ctacaggccc cacgtgtgag cccttcgggg gccagtgtcc 4440
ctgccatgcc catgtcattg gccgtgactg ctcccgctgt ggccaccggat actggggctt 4500
ccccaactgc aggccctgtg actgcgggtgc ccgcctctgt gacgagctca cgggccagtg 4560
catctgcccg ccacgcacca tcccgcccga ctgcctgctg tgccagcccc agactttgg 4620
ctgccacccc ctggtcggct gtgaggagtg taactgctca gggcccggca tccaggagct 4680
cacagaccct acctgtgaca cagacagcgg ccagtgcaag tgcagaccca acgtgactgg 4740
gcgccgctgt gatacctgct ctccgggctt ccatggctac cccgctgcc gccctgtga 4800
ctgtcacgag gcgggcactg cgcctggcgt gtgtgacccc ctcacagggc agtgctactg 4860
taaggagaac gtgcagggcc ccaaatgtga ccagtgcagc cttgggacct tctcactgga 4920
tgctgccaac cccaaaggtt gcaccgctg cttctgcttt ggggccacgg agcgctgccg 4980
gagctcgtcc tacacccgcc aggagttcgt ggatatggag ggatgggtgc tgctgagcac 5040
tgaccggcag gtggtgcccc acgagcggca gccaggacg gagatgctcc gtgcagacct 5100
gcggcacgtg cctgaggctg tgcccgagge tttccccgag ctgtactggc aggccccacc 5160
ctcctacctg ggggaccggg tgtcatccta cggtgggacc ctccgttatg aactgcactc 5220
agagacccag cggggagatg tcttttgtccc catggagagc aggccggatg tggtgctcga 5280
gggcaaccag atgagcatca cattcctgga gccggcatac cccacgcctg ccacgttca 5340
ccgtgggcag ctgcagctgg tggagggaaa cttccgggcat acgagacgc gcaacactgt 5400
gtcccgcgag gagctcatga tggtgctggc cagcctggag cagctgcaga tccgtgccct 5460
cttctcacag atctcctcgg ctgtcttcct gcgcagggtg gcactggagg tggccgacca 5520
agcaggccag ggggccctgg ccagcaatgt ggagctgtgc ctgtgccccg ccagctaccg 5580
gggggactca tgccaggaat gtgccccgg cttctatcgg gacgtcaaag gtctcttcct 5640
gggccgatgt gtcccttgtc agtgccatgg acactcagac cgctgcctcc ctggctctgt 5700
cgtctgtgtg gactgccagc acaacaccga aggggcccac tgtgagcgct gccaggctgg 5760
cttcgtgagc agcaggacg acccaggcgc cccctgctc agtgccttcc aacaactccg 5820
ccgagggctg tgtcctgcga gcggccgcca ccagctgcct 5880
ctgcaaacct ggttatgcag gtgcctcctg cgagcggtgt gcgcccggat ctctgggaa 5940
cccactggtg ctgggcagct cctgccagcc atgcgactgc agcggcaacg gtgacccaa 6000
cttgctcttc agcgactgcg acccctgac gggcgcctgc cgtggctgcc tgcgcacac 6060
cactgggcgc cgctgcgaga tctgtgccc cggcttctac caacctgcgc tgcctggcag 6120
caactgcacc cggtgcgact gtaccccatg tgggacagag gcctgcgacc ccacagcgg 6180
gcactgcctg tgcaaggcgg gcgtgactgg gcggcgctgt gaccgctgcc aggagggaca 6240
ttttggttc gatggctgcg ggggctgccg ccgtgtgct tgtggaccgg ccgccgaggg 6300
ctccgagtgc caccccaga gcggacagtg ccactgccga ccaggaccac tgggacccca 6360
gtgccgcgag tgtgccctg gctactgggg gctccctgag cagggctgca ggcgctgcca 6420
```

```
gtgccctggg ggccgctgtg accctcacac gggccgctgc aactgccccc cggggctcag   6480
cggggagcgc tgcgacacct gcagccagca gcatcaggtg cctgttccag gcgggcctgt   6540
gggccacagc atccactgtg aagtgtgtga ccactgtgtg gtcctgctcc tggatgacct   6600
ggaacgggcc ggcgccctcc tccccgccat tcacgagcaa ctgcgtggca tcaatgccaa   6660
ctccatggcc tgggcccgtc tgcacaggct gaacgctcc atcgctgacc tgcagagcca   6720
gctccggagc cccctgggcc ccgccatga gacggcacag cagctggagg tgctggagca   6780
gcagagcaca agcctcgggc aggacgcacg cggctaggc ggccaggccg tggggacccg   6840
agaccaggcg agccaattgc tggccggcac cgaggccaca ctgggccatg cgaagacgct   6900
gttggcggcc atccgggctg tggaccgcac cctgagcgag ctcatgtccc agacgggcca   6960
cctggggctg gccaatgcct cggctccatc aggtgagcag ctgctccgga cactggccga   7020
ggtgagcgg ctgctctggg agatgcgggc ccgggacctg ggggcccgc aggcagcagc   7080
tgaggctgag ttggctgcag cacagagatt gctggcccgg gtgcaggagc agctgagcag   7140
cctctgggag gagaaccagg cactggccac acaaacccgc gaccggctgg cccagcacga   7200
ggccggcctc atggacctgc gagaggcttt gaaccgggca gtggacgcca cacgggaggc   7260
ccaggagctc aacagccgca accaggagcg cctggaggaa gccctgcaaa ggaagcagga   7320
gctgtcccgg gacaatgcca ccctgcaggc cactctgcat gcggctaggg acaccctggc   7380
cagcgtcttc agattgctgc acagcctgga ccaggctaag gaggagctgg agcgcctcgc   7440
cgccagcctg gatggggctc gaccccact gctgcagagg atgcagacct tctccccggc   7500
gggcagcaag ctgcgtctag tggaggccgc cgaggcccac gcacagcagc tgggccagct   7560
ggcactcaat ctgtccagca tcatcctgga cgtcaaccag gaccgcctca cccagagggc   7620
catcgaggcc tccaacgcct acagccgcat cctgcaggcc gtgcaggctg ccgaggatgc   7680
tgctgccag gccctgcagc aggcggacca cacgtggtgc acggtggtgc ggcaggggct   7740
ggtggaccga gccagcagc tcctggccaa cagcactgca ctagaagagg ccatgctcca   7800
ggaacagcag aggctgggcc ttgtgtgggc tgccctccag ggtgccagga cccagctccg   7860
agatgtccgg gccaagaagg accagctgga ggcgcacatc caggcggcgc aggccatgct   7920
tgccatggac acagacgaga caagcaagaa gatcgcacat gccaaggctg tggctgctga   7980
agcccaggac accgccaccc gtgtgcagtc ccagctgcag gccatgcagg agaatgtgga   8040
gcggtggcag ggccagtacg agggcctgcg gggccaggac ctgggccagg cagtgcttga   8100
cgcaggccac tcagtgtcca ccctggagaa gacgctgccc cagctgctgg ccaagctgag   8160
catcctggac aaccgtgggg tgcacaacgc cagcctggcc ctgtccgcca gcattggccg   8220
cgtgcgagag ctcattgccc aggcccgggg ggctgccagt aaggtcaagg tgcccatgaa   8280
gttcaacggg cgctcagggg tgcagctgcg caccccacgg gatcttgccg accttgctgc   8340
ctacactgcc ctcaagttct acctgcaggg cccagagcct gagcctgggc agggtaccga   8400
ggatcgcttt gtgatgtaca tgggcagccg ccaggccact ggggactaca tggtgtgtc   8460
tctgcgtgac aagaaggtgc actgggtgta tcagctgggt gaggcgggcc ctgcagtcct   8520
aagcatcgat gaggacattg gggagcagtt cgcagctgtc agcctggaca ggactctcca   8580
gtttggccac atgtccgtca cagtggagag acagatgatc caggaaacca agggtgacac   8640
ggtggccct ggggcagagg ggctgctcaa cctgcgccca gacgacttcg tcttctacgt   8700
cggggggtac cccagtacct tcacgccccc tccctgctt cgcttcccg gctaccgggg   8760
ctgcatcgag atggacacgc tgaatgagga ggtggtcagc ctctacaact tcgagaggca   8820
cttccagctg gacacggctg tggacaggcc ttgtgcccgc tccaagtcga ccggggaccc   8880
gtggctcacg gacggctcct acctggacgg caccggcttc gcccgcatca gcttcgacag   8940
tcagatcagc accaccaagc gcttcagca ggagctgggc ctcgtgtcct acagcgggat   9000
gctcttcttc ctgaagcagc agagccagtt cctgtgcttg gccgtgcaag aaggcagcct   9060
cgtgctgttg tatgactttg gggctggcct gaaaaaggcc gtcccactgc agcccccacc   9120
gccccctgacc tcgccagca aggcgatcca ggtgttcctg ctgggggggca gccgcaagcg   9180
tgtgctggtg cgtgtggagc ggccacggt gtacagcgtg gagcaggaca atgatctgga   9240
gctggccgac gcctactacc tggggggcgt gccgcccgac cagctgcccc cgagcctgcg   9300
acggctcttc cccaccggag gctcagtccg tggctgcgtc aaaggcatca aggccctggg   9360
caagtatgtg gacctcaagc ggctgaacac gacaggcgtg agcgccggct gcaccgccga   9420
cctgctggtg gggcgcgcca tgactttcca tggccacgcc ttccttcgcc tggcgctcta   9480
gaacgtggca ccgctcactg gcaacgtcta ctccggcttc ggcttccaca gcgcccagga   9540
cagtgccctg ctctactacc gggcgtcccc ggatgggcta tgccaggtgt ccctgcagca   9600
gggccgtgtg agcctacagc tcctgaggac tgaagtgaaa actcaagcgg gcttcgccga   9660
tggtgccccc cattacgtcg ccttctacag caatgccacg ggagtctgtgc tgtatgtcga   9720
tgaccagctc cagcagatga agcccccacc gggaccaccc cccgagctcc agccgcagcc   9780
tgaggggccc ccgaggctcc tcctgggagg cctgcctgag tctggcacca tttacaactt   9840
cagtggctgc atcagcaacg tcttcgtgca gcggctcctg ggcccacagc gcgtatttga   9900
tctgcagcag aacctgggca gcgtcaatgt gagcaggggc tgtgcacccg ccctgcaagc   9960
ccagacccg ggcctggggc ctagaggact gcaggccacc gcccggaagg cctcccgccg  10020
cagccgtcag cccgccggcc atcctgcctg catgctgccc ccacacctca ggaccacccg  10080
agactcctac cagtttgggg gttccctgtc cagtcacctg gagtttgtgg gcatcctggc  10140
ccgacatagg aactggccca gtctctccat gcacgtcctc ccgcgaagct cccgaggcct  10200
cctcctcttc actgcccgtc tgaggccccgg cagccctcc tcgcgctct tcctgagcaa  10260
tggccacttc gttgcacaga tggaaggcct cgggactcgg ctccgcgccc agagccgcca  10320
gcgctcccgg cctggccgct ggcacaaggt ctccgtgcgc tgggagaaga accggatcct  10380
gctggtgacg gacgggggccc gggcctggag ccaggagggg ccgcaccggc agcaccaggg  10440
ggcagagcac cccagccgc acaccctctt tgtgggcggc ctcccggcca gcagccacag  10500
ctccaaactt ccggtgaccg tcgggttcag cggctgtgtg aagagactga ggctgcacag  10560
gaggcccctg ggggccccca cacgatggc aggggtcaca ccctgcatct tgggcccct  10620
ggaggcgggc ctgttcttcc caggcagcgg gggagttatc actttagacc tcccaggagc  10680
tacactgcct gatgtgggcc tggaactgga ggtgcggccc ctggcagtca ccggactgat  10740
cttccacttg ggcaggccc ggacgccccc ctacttgcag ttgcaggtga ccgagaagca  10800
agtcctggga ggatg acggagcagg ggagttctc acgtcagtga cccgccctc  10860
agtgctgtgt gatggccagt ggcaccggct agcggtgatg aaaagcggga atgtgctccg  10920
gctgaggtg gacgcgcaga gcaaccacac cgtgggccc ttgctggcgg ctgcagctgg  10980
tgccccagcc cctctgtacc tcgggggcct gcctgagccc atggccgtgc agccctggcc  11040
cccgcctac tgcggctgca tgaggaggct ggcggtgaac cggtccccgg tcgccatgac  11100
tcgctctgtg gaggtccacg gggcagtggg ggccagtggc tgcccagccg cctaggacac  11160
```

-continued

```
agccaacccc ggcccctggt caggcccctg cagctgcctc acaccgcccc ttgtgctcgc   11220
ctcataggtg tctatttgga ctctaagctc tacgggtgac agatcttgtt tctgaagatg   11280
gtttaagtta tagcttctta aacgaaagaa taaaatactg caaaatgttt ttatatttgg   11340
cccttccacc cattttaat tgtgagagat ttgtcaccaa tcatcactgg ttcctcctta   11400
aaaattaaaa agtaacttct gtgtaa                                        11426

SEQ ID NO: 6         moltype = DNA   length = 7632
FEATURE              Location/Qualifiers
source               1..7632
                     mol_type = other DNA
                     organism = Homo sapiens
SEQUENCE: 6
atgagaggga gccatcgggc cgcgccggcc ctgcggcccc ggggcggct ctggccgtg      60
ctggccgtgc tggcggcggc cgccgcgcg ggctgtgccc aggcagccat ggacgagtgc    120
acggacgagg gcgggcggcc gcagcgctgc atgcccgagt tcgtcaacgc cgccttcaac   180
gtgactgtgg tggccaccaa cacgtgtggg actccgcccg aggaatactg tgtgcagacc   240
ggggtgaccg ggggtcaccaa gtcctgtcac ctgtgcgacg ccgggcagcc ccacctgcag   300
cacggggcag ccttcctgac cgactacaac aaccaggccg acaccccttg gtggcaaagc   360
cagaccatgc tggccggggt gcagtacccc agctccatca acctcacgct gcacctggga   420
aaagcttttg acatcaccta tgtgcgtctc aagttccaca ccagccgccc ggagagcttt   480
gccatttaca agcgcacacg ggaagacggg ccctggattc cttaccagta ctacagtggt   540
tcctgtgaga acacctactc caaggcaaac cgcggcttca tcaggacagg aggggacgag   600
cagcaggcct tgtgtactga tgaattcagt gacatttctc ccctcactgg gggcaacgtg   660
gccttttcta ccctggaagg aaggcccagc gcctataact ttgacaatag ccctgtgctg   720
caggaatggg taactgccac tgacatcaga gtaactctta atcgcctgaa cacttttgga   780
gatgaagtgt ttaacgatcc caaagttctc aagtcctaat attatgccat ctctgatttt   840
gctgtaggtg gcagatgtaa atgtaatgga cacgcaagcg agtgtatgaa gaacgaattt   900
gataagctgc tgtgtaattg caaacataac acatatggag tagactgtga aaagtgtctt   960
cctttcttca atgaccggcc gtggaggagg gcaactgcgg aaagtgccag tgaatgcctg   1020
ccctgtgatt gcaatggtcg atcccaggaa tgctacttcg accctgaact ctatcgttcc   1080
actggccatg ggggccactg taccaactgc aggataaaca cagatggcgc ccactgtgag   1140
aggtgccgag agaacttctt ccgccttggc aacaatgaag cctgctcttc atgccactgt   1200
agtcctgtgg gctctctaag cacacagtgt gatagttacg gcagatgcag ctgtaagcca   1260
ggagtgatgg gggacaaatg tgaccgttgc cagcctggat tccattctct cactgaagca   1320
ggatgcaggc catgctcttg tgatccctct ggcagcatag atgaatgtaa tattgaaaca   1380
ggaagatgtg tttgcaaaga caatgtcgaa ggcttcaatt gtgaaagatg caaacctgga   1440
ttttttaatc tggaatcatc taatcctcgg ggttgcacac cctgcttctg ctttgggcat   1500
tcttctgtct gtacaaacgc tgttggctac agtgtttatt ctatctcctc taccttcag   1560
attgatgaga atgggtggcg tgcggaacag agagatgcct ctgaagcatc tctcgagtgg   1620
tcctctgaga ggcaagatat cgccgtgatc tcagacagct actttcctcg gtacttcatt   1680
gctcctgcaa agtcttgggg caagcaggtg ttgagttatg gtcagaacct ctccttctcc   1740
tttcgagtgg acaggcgaga tactcgcctc tctgcagaag accttgtgct tgagggagct   1800
ggcttaagag tatctgtacc cttgatcgct cagggcaatt cctatccaag tgagaccaat   1860
gtgaagtatg tcttcaggct ccatgaagca acagattacc cttggaggcc tgctcttacc   1920
ccttttgaat tcagaagctt cctaaacaac ttgacctcta tcaagatacg tgggacatac   1980
agtgagagaa gtgctggata tttggatgat gtcaccctgg caagtgctcg tcctgggcct   2040
ggagtccctg caacttgggt ggagtcctgc acctgtcctg tgggatatgg agggcagttt   2100
tgtgagatgt gcctctcagg ttacagaaga gaaactccta atcttggacc atacagtcca   2160
tgtgtgcttt cgcctgcaa tggacacagc gagacctgtg atcctgagac aggtgtttgt   2220
aactgcagag acaatacggc tggccgcac tgtgagaagt gcagtgatgg gtactatgga   2280
gattcaactg caggcacctc ctccgattgc caaccctgtc cgtgtcctgg aggttcaagt   2340
tgtgctgttg tcccaagac aaaggaggtg tgtgcacca actgtcctac tggcaccact   2400
ggtaagagat gtgagctctg tgatgatggc tactttggag accccctggg tagaaacggc   2460
cctgtgagac tttgccgcct gtgccagtgc agtgacaaca tcgatcccaa tgcagttgga   2520
aattgcaatc gcttgacggg agaatgcctg aagtgcatct ataacactgc tggcttctat   2580
tgtgaccggt gcaaagacgg attttttgga aatcccctgg ctcccaatcc agcagacaaa   2640
tgcaaagcct gcaattgcaa tctgtatggg accatgaagc agcagagcag ctgtaacccc   2700
gtgacggggc agtgtgaatg tttgcctcac gtgactggcc aggactgtgg tgcttgtgac   2760
cctggattct acaatctgca gagtgggcaa ggctgtgaga ggtgtgactg ccatgccttg   2820
ggctccacca atgggcagtg tgacatccgc accggccagt gtgagtgcca gccccggcatc   2880
actggtcagc actgtgagcg ctgtgaggtc aaccactttg ggtttggacc tgaaggctgc   2940
aaaccctgtg actgtcatcc tgagggatct ctttcacttc agtgcaaaga tgatggtcgc   3000
tgtgaatgca gagaaggctt tgtgggaaat cgctgtgacc agtgtgaaga aaactatttc   3060
tacaatgggt cttggccttgg ctgccaggaa tgtccagctt gttaccggct ggtaaaggat   3120
aaggttgctg atcatagagt gaagctccag gaattagaga gtctcatagc aaaccttgga   3180
actgggggatg agatggtgac agatcaagcc ttcgaggata gactaaagga agcagagagg   3240
gaagttatgg acctccttcg tgaggcccag gatgtcaaag atgttgacca gaatttgatg   3300
gatcgcctac agagagtgaa taacactctg tccagccaaa ttagccgttt acagaatatc   3360
cggaatacca ttgaagagac tggaaacttg gctgaacaag cgctgccca tgtagagaac   3420
acagagcggt tgattgaaat cgcatccaga gaacttgaga agcaaaagt cgctgctgcc   3480
aatgtgtcag tcactcagcc agaatctaca gggacccaa acaacatgac tctttttggca   3540
gaagaggctc gaaagcttgc tgaacgtcat aaacaggaag ctgatgacat tgttcgagtg   3600
gcaaagacag ccaatgatac gtcaactgag gcatacaacc tgcttctgag gacactggca   3660
ggagaaaatc aacagcatt tgagattgaa gagcttaata ggaagtatga acaagcgaag   3720
aacatctcac aggatctgga aaacaagct gcccgagtac atgaggaggc caaagggcc   3780
ggtgacaaag ctgtgagat ctatgccagc gtggctcagc tgagcccttt ggactctgag   3840
acactggaga atgaagcaaa taacataaag atggaagctg agaatctgga caactgatt   3900
gaccagaaat taaaagatta tgaggacctc agaagaata tgagggaa ggaacttgaa   3960
gtcaagaacc ttctggagaa aggcaagact gaacagcaga ccgcagacca actcctagcc   4020
```

```
cgagctgatg ctgccaaggc cctcgctgaa gaagctgcaa agaagggacg ggatacctta   4080
caagaagcta atgacattct caacaacctg aaagattttg ataggcgtgt gaacgataac   4140
aagacggccg cagaggaggc actaaggaag attcctgcca tcaaccagac catcactgaa   4200
gccaatgaaa agaccagaga agcccagcag gccctgggag tgctgcggc ggatgccaca    4260
gaggccaaga acaaggccca tgaggcggga aggatcgaca gcgctgtcca aaagaatgcc   4320
accagcacca aggcagaagc tgaaagaact tttgcagaag ttacagatct ggataatgag   4380
gtgaacaata tgttgaagca actgcaggaa gcagaaaaag agctaaagag aaaacaagat   4440
gacgctgacc aggacatgat gatggcaggg atggcttcac aggctgctca agaagccgag   4500
atcaatgcca gaaaagccaa aaactctgtt actagcctcc tcagcattat taatgacctc   4560
ttggagcagc tggggcagct ggatacagtg gacctgaata agctaaacga gattgaaggc   4620
accctaaaca aagccaaaga tgaaatgaag gtcagcgatc ttgataggaa agtgtctgac   4680
ctggagaatg aagccaagaa gcaggaggct gccatcatgg actataaccg agatatcgag   4740
gagatcatga aggacattcg caatctggag gacatcagga agaccttacc atctggctgc   4800
ttcaacaccc cgtccattga aaagccctag tgtctttagg gctggaaggc agcatccctc   4860
tgacagggg gcagttgtga ggccacagag tgccttgaca caaagattac atttttcaga   4920
cccccactcc tctgctgctg tccatgactg tccttttgaa ccaggaaaag tcacagagtt   4980
taaagagaag caaattaaac atcctgaatc gggaacaaag ggttttatct aataaagtgt   5040
ctcttccatt cacgttgcta ccttacccac actttcccct ctgatttgcg tgaggacgtg   5100
gcatcctacg ttactgtaca gtggcataag cacatcgtgt gagcccatgt atgctgggt    5160
agagcaagta gccctcccct gtctcatcga taccagcaga acctcctcag tctcagtact   5220
cttgtttcta tgaaggaaaa gtttggctac taacagtagc attgtgatgg ccagtatatc   5280
cagtccatgg ataaagaaaa tgcatctgca tctcctaccc ctcttcctc taagcaaaag    5340
gaaataaaca tcctgtgcca aaggtattgg tcatttagaa tgtcggtagc catccatcag   5400
tgcttttagt tattatgagt gtaggacact gagccatccg tgggtcagga tgcaattatt   5460
tataaaagtc tccaggtgaa catggctgaa gatttttcta gtatattaat aattgactag   5520
gaagatgaac ttttttttcag atctttgggc agctgataat ttaaatctgg atgggcagct   5580
tgcactcacc aatagaccaa aagacatctt tgatattct tataaatgaa acttacacag    5640
aagaaatagg gatatgataa ccactaaaat tttgttttca aaatcaaact aattcttaca   5700
gcttttttat tagttagtct tggaactagt gttaagtatc tggcagagaa cagttaatcc   5760
ctaaggtctt gacaaaacag aagaaaaaca agcctcctcg tcctagtctt ttctagcaaa   5820
gggataaaac ttagatggca gcttgtactg tcagaatccc gtgtatccat ttgttcttct   5880
gttggagaga tgagacattt gacccttagc tccagttttc ttctgatgtt tccatcttcc   5940
agaatccctc aaaaaacatt gtttgccaaa tcctggtggc aaatacttgc actcagtatt   6000
tcacacagct gccaacgcta tcgagttcct gcacttgtg atttaaatcc actctaaacc    6060
ttccctctaa gtgtagaggg aagaccctta cgtggagttt cctagtgggc ttctcaactt   6120
ttgatcctca gctctgtggt tttaagacca cagtgtgaca gttccctgcc acacacccc    6180
ttcctcctac caacccacct tgagattca tatatagcct ttaacactat gcaactttgt    6240
actttgcgta gcaggggcgg ggtgggggga agaaaactat tatctgacac actggtgcta   6300
ttaattattt caaatttata tttttgtgtg aatgttttgt gttttgttta tcatgattat   6360
agaataagga atttatgtaa atatacttag tcctatttct agaatgacac tctgttcact   6420
ttgctcaatt tttcctcttc actggcacaa tgtatctgaa tacctccttc cctcccttct   6480
agaattcttt ggattgtact ccaaagaatt gtgccttgtg tttgcagcat ctccattctc   6540
taaaattaat ataattgctt tcctccacac ccagccactg taaagaggta acttgggtcc   6600
tcttccattg cagtcctgat gatcctaacc tgcagcacgg tggttttaca atgttccaga   6660
gcaggaacgc caggttgaca agctatggta ggattaggaa agtttgctga agaggatctt   6720
tgacgccaca gtgggactag ccaggaatga gggagaaatg cccttctggc aattgttgg    6780
agctggatag gtaagttta aagggagta catttgact gagcacttag ggcatcagga     6840
acagtgctac ttactgatgg gtagactggg agaggtggtg taacttagtt cttgatgatc   6900
ccacttcctg tttccatctg cttgggatat accagagttt accacaagtg ttttgacgat   6960
atactcctga gctttcactc tgctgcttct cccaggcctc ttctactatg caggagatg    7020
tggcgtgctg ttgcaaagtt ttcacgtcat tgtttcctgg ctagttcatt tcattaagtg   7080
gctacatcct aacatatgca tttggtcaag gttgcagaag aggactgaag attgactgcc   7140
aagctagttt gggtgaagtt cactccagca agtctcaggc cacaatgggg tggtttggtt   7200
tggttttcctt ttaactttct ttttgttatt tgcttttctc ctccacctgt gtggtatatt   7260
ttttaagcag aatttctttt tttaaaataa aaggttcttt acaagatgat accttaatta   7320
cactcccgca acacagccat tatttttattg tctagctcca gttatctgta ttttatgtaa   7380
tgtaattgac aggatggctg ctgcagaatg ctggttgaca cagggattat tatactgcta   7440
ttttttccctg aattttttc ctttgaattc caactgtgga ccttttatat gtgccttcac   7500
tttagctgtt tgccttaatc tctacagcct tgctctccgg ggtggttaat aaaatgcaac   7560
acttggcatt tttatgtttt aagaaaaaca gtatttatt tataataaaa tctgaatatt     7620
tgtaaccctt ta                                                        7632

SEQ ID NO: 7               moltype = DNA   length = 24
FEATURE                    Location/Qualifiers
misc_feature               1..24
                           note = primer
source                     1..24
                           mol_type = other DNA
                           organism = synthetic construct
SEQUENCE: 7
gtggtaccca caggcagagt tgac                                             24

SEQ ID NO: 8               moltype = DNA   length = 26
FEATURE                    Location/Qualifiers
misc_feature               1..26
                           note = primer
source                     1..26
                           mol_type = other DNA
                           organism = synthetic construct
```

-continued

```
SEQUENCE: 8
gctctagagc tcttcagtgc ataggc                                    26
```